US009006232B2

(12) United States Patent
    Nakayama et al.

(10) Patent No.: US 9,006,232 B2
(45) Date of Patent: Apr. 14, 2015

(54) PYRIMIDONE DERIVATIVES

(75) Inventors: Kazuki Nakayama, Tokyo (JP); Daiki Sakai, Kanagawa (JP); Kazutoshi Watanabe, Tokyo (JP); Toshiyuki Kohara, Kanagawa (JP); Keiichi Aritomo, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 357 days.

(21) Appl. No.: 13/389,512

(22) PCT Filed: Aug. 11, 2010

(86) PCT No.: PCT/JP2010/063891
    § 371 (c)(1),
    (2), (4) Date: Apr. 24, 2012

(87) PCT Pub. No.: WO2011/019090
    PCT Pub. Date: Feb. 17, 2011

(65) Prior Publication Data
    US 2012/0208797 A1    Aug. 16, 2012

(30) Foreign Application Priority Data

Aug. 13, 2009  (JP) .................. 2009-204096

(51) Int. Cl.

| A61K 31/5377 | (2006.01) |
|---|---|
| A61K 31/536 | (2006.01) |
| A61K 31/505 | (2006.01) |
| A61K 31/55 | (2006.01) |
| C07D 403/14 | (2006.01) |
| C07D 413/14 | (2006.01) |
| C07D 265/14 | (2006.01) |
| C07D 401/12 | (2006.01) |
| C07D 233/76 | (2006.01) |
| C07D 401/14 | (2006.01) |
| C07D 407/12 | (2006.01) |
| C07D 409/14 | (2006.01) |

(52) U.S. Cl.
    CPC ............ *C07D 401/12* (2013.01); *C07D 233/76* (2013.01); *C07D 401/14* (2013.01); *C07D 407/12* (2013.01); *C07D 409/14* (2013.01); *C07D 413/14* (2013.01)

(58) Field of Classification Search
    CPC .. C07D 403/14; C07D 413/14; C07D 265/14; A61K 31/5377; A61K 31/536; A61K 31/505; A61K 31/55
    USPC ......... 514/217.06, 274, 252.18, 235.8, 230.5; 544/92, 123, 296; 540/601
    See application file for complete search history.

(56) References Cited

U.S. PATENT DOCUMENTS

| 7,256,199 B1 | 8/2007 | Watanabe et al. |
| 7,504,411 B2 | 3/2009 | Watanabe et al. |
| 7,994,315 B2 | 8/2011 | Okuyama et al. |
| 2003/0187004 A1 | 10/2003 | Almario Garcia et al. |
| 2005/0090490 A1 | 4/2005 | Uehara et al. |
| 2005/0130967 A1 | 6/2005 | Uehara et al. |
| 2007/0142409 A1 | 6/2007 | Usui et al. |
| 2009/0124618 A1 | 5/2009 | Watanabe et al. |
| 2009/0233918 A1 | 9/2009 | Fukunaga et al. |
| 2009/0239864 A1 | 9/2009 | Watanabe et al. |
| 2010/0113775 A1 | 5/2010 | Watanabe et al. |

(Continued)

FOREIGN PATENT DOCUMENTS

| EP | 0 616 032 B1 | 11/2003 |
| JP | 2002-525366 | 8/2002 |

(Continued)

OTHER PUBLICATIONS

Japanese Office Action issued with respect to Japanese Patent Application No. 2012-507488, mailed Aug. 27, 2013, along with an English language excerption.
Ferrer et al., "Glycogen synthase kinase-3 is associated with neuronal and glial hyperphosphorylated tau deposits in Alzheimer's disease, Pick's disease, progressive supranuclear palsy and corticobasal degeneration", Acta Neuropathol., vol. 104, pp. 583-591 (2002).
Koh et al., "Role of GSK-3β activity in motor neuronal cell death induced by G93A or A4V mutant hSOD1 gene", European Journal of Neuroscience, vol. 22, pp. 301-309 (2005).
Droucheau et al., "*Plasmodium falciparum* glycogen synthase kinase-3: molecular model, expression, intracellular localisation and selective inhibitors", Biochimica et Biophysica Acta, vol. 1697, pp. 181-196 (2004).

(Continued)

*Primary Examiner* — James O Wilson
*Assistant Examiner* — Ebenezer O Sackey
(74) *Attorney, Agent, or Firm* — Greenblum & Bernstein, P.L.C.

(57) ABSTRACT

A compound represented by the formula (I) or a pharmaceutically acceptable salt thereof:

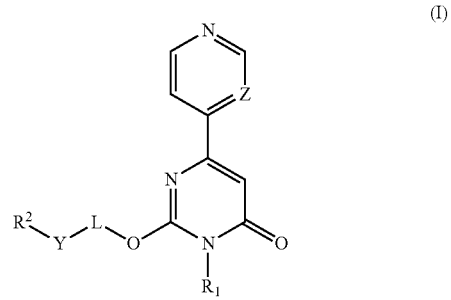

wherein Z represents nitrogen atom or C—X; X represents hydrogen atom or fluorine atom; $R^1$ is hydrogen atom or a $C_1$-$C_3$ alkyl group; L represents single bond or a $C_1$-$C_6$ alkylene group which may be substituted; Y represents single bond, sulfur atom, oxygen atom, NH, or the like; $R^2$ represents hydrogen atom or a cyclic group which may be substituted, which is used for preventive and/or therapeutic treatment of a disease caused by abnormal activity of tau protein kinase 1 such as a neurodegenerative diseases (e.g. Alzheimer disease).

11 Claims, No Drawings

(56) References Cited

U.S. PATENT DOCUMENTS

| | | | |
|---|---|---|---|
| 2011/0021773 A1 | 1/2011 | Fukunaga et al. | |
| 2011/0251385 A1 | 10/2011 | Okuyama et al. | |
| 2011/0257392 A1 | 10/2011 | Okuyama et al. | |
| 2012/0095216 A1 | 4/2012 | Watanabe et al. | |

FOREIGN PATENT DOCUMENTS

| | | |
|---|---|---|
| JP | 2005-510472 | 4/2005 |
| JP | 2006-510684 | 3/2006 |
| JP | 2008-512347 | 4/2008 |
| WO | 00/18758 A1 | 4/2000 |
| WO | 01/70729 A1 | 9/2001 |
| WO | 03/027080 A1 | 4/2003 |
| WO | 03/037888 A1 | 5/2003 |
| WO | 2004/055007 A1 | 7/2004 |
| WO | 2006/028290 A1 | 3/2006 |
| WO | 2006/036015 A2 | 4/2006 |

OTHER PUBLICATIONS

Nielsen et al., "GABA Agonists and Uptake Inhibitors. Synthesis, Absolute Stereochemistry, and Enantioselectivity of (R)-(−)- and (S)-(+)-Homo-β-proline", J. Med. Chem., vol. 33, No. 1, pp. 71-77 (1990).

Frame et al., "GSK3 takes centre stage more than 20 years after its discovery", Biochem. J., vol. 359, pp. 1-16 (2001).

Eldar-Finkelman, "Glycogen synthase kinase 3: an emerging therapeutic target", Trends in Molecular Medicine, vol. 8, No. 3, pp. 126-132 (2002).

Kaytor et al., "The GSK3β signaling cascade and neurodegenerative disease", Current Opinion in Neurobiology, vol. 12, pp. 275-278 (2002).

Neidlien et al., "Synthese von 3.4-sowie 4-substituierten Uracilen and Thiouracilen", Arch. Pharmaz., pp. 596-601 (1972).

Masters et al., "Neuronal origin of a cerebral amyloid: neurofibrillary tangles of Alzheimer's disease contain the same protein as the amyloid of plaque cores and blood vessels", The EMBO Journal, vol. 4, No. 11, pp. 2757-2763 (1985).

Glenner et al., "Alzheimer's Disease: Initial Report of the Purification and Characterization of a Novel Cerebrovascular Amyloid Protein", Biochemical and Biophysical Research Communications, vol. 120, No. 3, pp. 885-890 (1984).

Masters et al., "Amyloid plaque core protein in Alzheimer disease and Down syndrome", Proc. Natl. Acad. Sci. USA, vol. 82, pp. 4245-4249 (1985).

Wischik et al., "Isolation of a fragment of tau derived from the core of the paired helical filament of Alzheimer disease", Proc. Natl. Acad. Sci. USA, vol. 85, pp. 4506-4510 (1988).

Kondo et al., "The Carboxyl Third of Tau is Tightly Bound to Paired Helical Filaments", Neuron, vol. 1, pp. 827-834 (1988).

Sherrington et al., "Cloning of a gene bearing missense mutations in early-onset familial Alzheimer's disease", Nature, vol. 375, pp. 754-760 (1995).

Levy-Lahad et al., "Candidate Gene for the Chromosome 1 Familial Alzheimer's Disease Locus", Science, vol. 269, pp. 973-977 (1995).

Rogaev et al., "Familial Alzheimer's disease in kindreds with missense mutations in gene on chromosome 1 related to the Alzheimer's disease type 3 gene", Nature, vol. 376, pp. 775-778 (1995).

Borchelt et al., "Familial Alzheimer's Disease-Linked Presenilin I Variants Elevate Aβ1-42/1-40 Ratio In Vitro and In Vivo", Neuron, vol. 17, pp. 1005-1013 (1996).

Tomita et al., "The presenilin 2 mutation (N141I) linked to familial Alzheimer disease (Volga German families) increases the secretion of amyloid β protein ending at the 42nd (or 43rd) residue", Proc. Natl. Acad. Sci. USA, vol. 94, pp. 2025-2030 (1997).

Copani et al., "β-Amyloid Protein Potentiates Injury by Glucose Deprivation in Neuronal Cortical Cultures ", Society for Neuroscience Abstracts, vol. 17, pp. 1445 (1991).

Siman et al., "Proteolytic Processing of β-Amyloid Precursor by Calpain I", The Journal of Neuroscience, vol. 10, No. 7, pp. 2400-2411 (1990).

Ihara et al., "Phosphorylated Tau Protein is integrated into Paired Helical Filaments in Alzheimer's Disease", J. Biochem., vol. 99, No. 6, pp. 1807-1810 (1986).

Grundke-Iqbal et al., "Abnormal phosphorylation of the microtubule-associated protein (tau) in Alzheimer cytoskeletal pathology", Proc. Natl. Acad. Sci. USA, vol. 83, pp. 4913-4917 (1986).

Ishiguro et al., "Tau Protein Kinase I Converts Normal Tau Protein into A68-like Component of Paired Helical Filaments", The Journal of Biological Chemistry, vol. 267, No. 16, pp. 10897-10901 (1992).

Ishiguro et al., "Glycogen synthase kinase 3β is identical to tau protein kinase I generating several epitopes of paired helical filaments", FEBS Letters, vol. 325, No. 3, pp. 167-172 (1993).

Yankner et al., "Neurotrophic and Neurotoxic Effects of Amyloid β Protein: Reversal by Tachykinin Neuropeptides", Science, vol. 250, pp. 279-282 (1990).

Takashima et al., "Tau protein kinase I is essential for amyloid β-protein-induced neurotoxicity", Proc. Natl. Acad. Sci. USA, vol. 90, pp. 7789-7793 (1993).

English Translation of International Search Report issued with respect to PCT/JP2010/063891, dated Dec. 14, 2010.

English Translation of International Preliminary Report on Patentability issued with respect to PCT/JP2010/063891, dated Feb. 14, 2012.

U.S. Appl. No. 13/389,504 to Daiki Sakai et al., filed Feb. 8, 2012.

PYRIMIDONE DERIVATIVES

TECHNICAL FIELD

The present invention relates to compounds that are useful as an active ingredient of a medicament for preventive and/or therapeutic treatment of diseases mainly caused by abnormal activity of tau protein kinase 1 (TPK1 also called GSK3beta: glycogen synthase kinase 3 beta), such as neurodegenerative diseases (e.g. Alzheimer disease).

BACKGROUND ART

Alzheimer disease is progressive senile dementia, in which marked cerebral cortical atrophy is observed due to degeneration of nerve cells and decrease of nerve cell number. Pathologically, numerous senile plaques and neurofibrillary tangles are observed in brain. The number of patients has been increased with the increment of aged population, and the disease arises a serious social problem. Although various theories have been proposed, a cause of the disease has not yet been elucidated. Early resolution of the cause has been desired.

It has been known that the degree of appearance of two characteristic pathological changes of Alzheimer disease well correlates to the degree of intellectual dysfunction. Therefore, researches have been conducted from early 1980's to reveal the cause of the disease through molecular level investigations of components of the two pathological changes. Senile plaques accumulate extracellularly, and β amyloid protein has been elucidated as their main component (abbreviated as "Aβ" hereinafter in the specification: Biochem. Biophys. Res. Commun., 120, 885 (1984); EMBO J., 4, 2757 (1985); Proc. Natl. Acad. Sci. USA, 82, 4245 (1985)). In the other pathological change, i.e., the neurofibrillary tangles, a double-helical filamentous substance called paired helical filament (abbreviated as "PHF" hereinafter in the specification) accumulate intracellularly, and tau protein, which is a kind of microtubule-associated protein specific for brain, has been revealed as its main component (Proc. Natl. Acad. Sci. USA, 85, 4506 (1988); Neuron, 1, 827 (1988)).

Furthermore, on the basis of genetic investigations, presenilins 1 and 2 were found as causative genes of familial Alzheimer disease (Nature, 375, 754 (1995); Science, 269, 973 (1995); Nature. 376, 775 (1995)), and it has been revealed that presence of mutants of presenilins 1 and 2 promotes the secretion of Aβ (Neuron, 17, 1005 (1996); Proc. Natl. Acad. Sci. USA, 94, 2025 (1997)). From these results, it is considered that, in Alzheimer disease, Aβ abnormally accumulates and agglomerates due to a certain reason, which engages with the formation of PHF to cause death of nerve cells. It is also expected that extracellular outflow of glutamic acid and activation of glutamate receptor responding to the outflow may possibly be important factors in an early process of the nerve cell death caused by ischemic cerebrovascular accidents.

It has been reported that kainic acid treatment that stimulates the AMPA receptor, one of glutamate receptor, increases mRNA of the amyloid precursor protein (abbreviated as "APP" hereinafter in the specification) as a precursor of Aβ (Society for Neuroscience Abstracts, 17, 1445 (1991)), and also promotes metabolism of APP (The Journal of Neuroscience, 10, 2400 (1990)). Therefore, it has been strongly suggested that the accumulation of Aβ is involved in cellular death due to ischemic cerebrovascular disorders. Other diseases in which abnormal accumulation and agglomeration of Aβ are observed include, for example, Down syndrome, cerebral bleeding due to solitary cerebral amyloid angiopathy, Lewy body disease and the like. Furthermore, as diseases showing neurofibrillary tangles due to the PHF accumulation, examples include progressive supranuclear palsy, subacute sclerosing panencephalitic parkinsonism, postencephalitic parkinsonism, pugilistic encephalitis, Guam parkinsonism-dementia complex, Lewy body disease and the like.

The tau protein is generally composed of a group of related proteins that forms several bands at molecular weights of 48-65 kDa in SDS-polyacrylamide gel electrophoresis, and it promotes the formation of microtubules. It has been verified that tau protein incorporated in the PHF in the brain suffering from Alzheimer disease is abnormally phosphorylated compared with usual tau protein (J. Biochem., 99, 1807 (1986); Proc. Natl. Acad. Sci. USA, 83, 4913 (1986)). An enzyme catalyzing the abnormal phosphorylation has been isolated. The protein was named as tau protein kinase 1 (abbreviated as "TPK1" hereinafter in the specification), and its physicochemical properties have been elucidated (J. Biol. Chem., 267, 10897 (1992)). Moreover, cDNA of rat TPK1 was cloned from a rat cerebral cortex cDNA library based on a partial amino acid sequence of TPK1, and its nucleotide sequence was determined and an amino acid sequence was deduced. As a result, it has been revealed that the primary structure of the rat TPK1 corresponds to that of the enzyme known as rat GSK-3β (glycogen synthase kinase 38, FEBS Lett., 325, 167 (1993)).

It has been reported that Aβ, the main component of senile plaques, is neurotoxic (Science, 250, 279 (1990)). However, various theories have been proposed as for the reason why Aβ causes the cell death, and any authentic theory has not yet been established. Takashima et al. observed that the cell death was caused by Aβ treatment of fetal rat hippocampus primary culture system, and then found that the TPK1 activity was increased by Aβ treatment and the cell death by Aβ was inhibited by antisense of TPK1 (Proc. Natl. Acad. Sci. USA, 90, 7789 (1993); EP616032).

In view of the foregoing, compounds which inhibit the TPK1 activity may possibly suppress the neurotoxicity of Aβ and the formation of PHF and inhibit the nerve cell death in the Alzheimer disease, thereby cease or defer the progress of the disease.

As compounds structurally similar to the compounds of the present invention represented by formula (I) described later, the compounds disclosed in the International Publication Nos. WO01/70729, WO03/037888 and WO03/027080 are known. However, in the above publications, no pyrimidone derivative compounds that is substituted by oxygen atom at 2-position, as the compounds of the present invention, have been studied.

CITATION LIST

Patent Literature

EP616032
WO01/70729
WO03/037888
WO03/027080

Non Patent Literature

Biochem. Biophys. Res. Commun., 120, 885 (1984)
EMBO J., 4, 2757 (1985)
Proc. Natl. Acad. Sci. USA, 82, 4245 (1985)
Proc. Natl. Acad. Sci. USA, 85, 4506 (1988)
Neuron, 1, 827 (1988)
Nature, 375, 754 (1995)

Science, 269, 973 (1995)
Nature. 376, 775 (1995)
Neuron, 17, 1005 (1996)
Proc. Natl. Acad. Sci. USA, 94, 2025 (1997)
Society for Neuroscience Abstracts, 17, 1445 (1991)
The Journal of Neuroscience, 10, 2400 (1990)
J. Biochem., 99, 1807 (1986)
Proc. Natl. Acad. Sci. USA, 83, 4913 (1986)
J. Biol. Chem., 267, 10897 (1992)
FEBS Lett., 325, 167 (1993)
Science, 250, 279 (1990)
Proc. Natl. Acad. Sci. USA, 90, 7789 (1993)

SUMMARY OF INVENTION

Technical Problem

An object of the present invention is to provide compounds useful as an active ingredient of a medicament for preventive and/or therapeutic treatment of diseases such as Alzheimer disease.

More specifically, the object is to provide novel compounds useful as an active ingredient of a medicament that enables radical prevention and/or treatment of the neurodegenerative diseases such as Alzheimer disease by inhibiting the TPK1 activity to suppress the neurotoxicity of Aβ and the formation of the PHF and by inhibiting the death of nerve cells.

Solution to Problem

In order to achieve the foregoing object, the inventors of the present invention conducted screenings of various compounds having inhibitory activity against the phosphorylation of TPK1. As a result, they found that compounds represented by the following formula (I) had the desired activity and were useful as an active ingredient of a medicament for preventive and/or therapeutic treatment of the aforementioned diseases.

The present invention was achieved on the basis of these findings.

The present invention thus provides a compound represented by general formula (I):

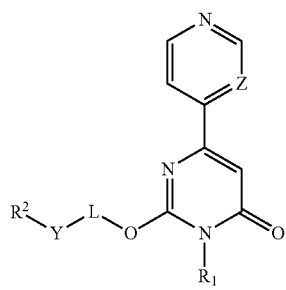

(I)

wherein:
Z represents nitrogen atom or C—X;
X represents hydrogen atom or fluorine atom;
$R^1$ is hydrogen atom or a $C_1$-$C_3$ alkyl group;
L represents single bond or a $C_1$-$C_6$ alkylene group which may be substituted;
Y represents single bond, sulfur atom, oxygen atom, or $NR^{10}$;
$R^{10}$ represents hydrogen atom or a $C_1$-$C_3$ alkyl group;
$R^2$ represents hydrogen atom or a cyclic group which may be substituted;
provided that when Y represents sulfur atom, oxygen atom, or $NR^{10}$, L is not single bond,
and when each of L and Y represents single bond, $R^2$ is not hydrogen atom,
or a pharmaceutically acceptable salt thereof.

Further, the present invention relates to a method for preparation of the compound represented by general formula (I) or a pharmaceutically acceptable salt thereof.

Further, the present invention relates to a pharmaceutical composition containing the compound represented by general formula (I) or a pharmaceutically acceptable salt thereof as an active ingredient.

Further, the present invention relates to a method for treatment or prophylaxis of a disease or condition, which comprises administering an effective amount of the compound represented by general formula (I) or a pharmaceutically acceptable salt thereof to a patient.

Still Further, the present invention relates to a use of the compound represented by general formula (I) or a pharmaceutically acceptable salt thereof for manufacture of a medicament.

Still Further, the present invention relates to a use of the compound represented by general formula (I) or a pharmaceutically acceptable salt thereof for the inhibition of tau protein kinase 1 activity.

The compound of the present invention or a pharmaceutically acceptable salt thereof exhibits an excellent inhibitory activity on TPK1. The pharmaceutical composition containing the compound of the present invention is useful as an active ingredient in a medicament for treatment or prophylaxis of a disease or condition which may be expected to be improved by inhibition of TPK1.

DESCRIPTION OF EMBODIMENTS

Unless otherwise indicated, the following definitions are set forth to illustrate the meaning and scope of the various terms used to describe the invention herein.

The term "a $C_1$-$C_3$ alkyl group" means an alkyl group having 1 to 3 carbon atoms which may be either linear or branched. The examples of the $C_1$-$C_3$ alkyl group include methyl, ethyl, n-propyl, and isopropyl groups.

The term "a $C_1$-$C_6$ alkyl group" means an alkyl group having 1 to 6 carbon atoms which may be either linear or branched. The examples of the $C_1$-$C_6$ alkyl group include methyl, ethyl, n-propyl, isopropyl, n-butyl, isobutyl, sec-butyl, tert-butyl, n-pentyl, isopentyl, neopentyl, 1,1-dimethylpropyl, 1-ethylpropyl, n-hexyl, and isohexyl groups.

The term "a halogen atom" means, for example, a fluorine atom, a chlorine atom, a bromine atom, and iodine atom.

The term "a $C_1$-$C_6$ alkylene group" means an alkylene having 1 to 6 carbon atoms. The examples of the $C_1$-$C_6$ alkylene group include methylene, ethylene, propylene, butylene, pentylene, and hexylene groups.

The term "a $C_6$-$C_{10}$ aryl group" means a group having 6 to 10 carbon atoms derived from, for example, benzene, naphthalene, indane, indene, or tetrahydronaphthalene. As the $C_6$-$C_{10}$ aryl group, phenyl group is preferable.

The term "5- or 6-membered aliphatic mono-heterocyclic group" means a group derived from, for example, a 5- to 6-membered monocyclic aliphatic hetero ring compound having as ring-constituting atoms one or more carbon atoms and one or two hetero atoms selected from the group consisting of oxygen atom, sulfur atom, and nitrogen atom.

The term "5- or 6-membered heteroaryl group" means a group derived from, for example, a 5- to 6-membered monocyclic aromatic hetero ring compound having as ring-constituting atoms one or more carbon atoms and one or two hetero atoms selected from the group consisting of oxygen atom, sulfur atom, and nitrogen atom.

The term "which may be substituted" means a group which may have one or more substituents. The number of substituents as well as their types and substituting positions are not particularly limited, and when two or more substituents are present, they may be the same or different.

The symbol "Z" in the aforementioned formula (I) is preferably nitrogen atom, C—H, or C—F, more preferably nitrogen atom or C—F.

In "the $C_1$-$C_6$ alkylene group which is substituted" represented by L, the $C_1$-$C_6$ alkylene group may have one or more, preferably one to four, substituent(s). When the $C_1$-$C_6$ alkylene group has two or more substituents, the substituents may be the same or different, and the examples of the substituents include a halogen atom, amino group, nitro group, cyano group, oxo group, hydroxyl group, carboxyl group, a $C_1$-$C_6$ alkyl group, and a $C_1$-$C_6$ alkyl-O— group. Among them, oxo group is preferable.

When Y is sulfur atom, oxygen atom, or $NR^{10}$ ($R^{10}$ represents hydrogen atom or a $C_1$-$C_3$ alkyl group), $R^2$ is preferably a phenyl group which is unsubstituted or substituted with one or more, preferably one to three $C_1$-$C_6$ alkyl groups.

The $C_1$-$C_3$ alkyl group represented by $R^1$ is preferably methyl group.

In "the cyclic group which may be substituted" represented by $R^2$, the cyclic group may be either a cyclic hydrocarbon group or a heterocyclic group. The cyclic group may be either saturated or unsaturated, and either aliphatic or aromatic. The cyclic group may be a mono-cyclic or poly-cyclic group, and preferably a mono- or bi-cyclic group. The cyclic group may also have a bridging structure. The numbers of the ring-constituting atoms of the cyclic group is not particularly limited, and generally may be 4 to 10. The cyclic group may preferably be a cyclic group selected from the following (1) and (2):
(1) a 4- to 10-membered mono- or bi-cyclic aliphatic group which may contain one or two hetero atoms selected from nitrogen atom, oxygen atom and sulfur atom, and may contain bridging structure;
(2) a 5- to 10-membered mono- or bi-cyclic aromatic group which may contain one to four hetero atoms selected from nitrogen atom, oxygen atom and sulfur atom. Preferable examples of the cyclic group include piperidyl group, pyrrolidinyl group, perhydroazepinyl group represented by the following formula:

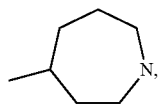

cyclohexyl group, cyclopentyl group, cycloheptyl group, 8-aza-bicyclo[3.2.1]octanyl group, phenyl group, dioxolanyl group, oxanyl group, and pyridyl group.

$R^2$ may preferably be a cyclic group which may have 1 to 3 substituents. The substituents are the same or different and selected from the group consisting of a halogen atom, nitro group, cyano group, a $C_1$-$C_6$ alkyl group which may be substituted, a $C_6$-$C_{10}$ aryl group which may be substituted, a 5- to 10-membered heterocyclic group which may be substituted, a $C_1$-$C_6$ alkyl-CO— group which may be substituted, a $C_1$-$C_6$ alkyl-O— group which may be substituted, a $C_1$-$C_6$ aryl-CO— group which may be substituted, a $C_1$-$C_6$ alkyl-O—CO— group which may be substituted, a $C_6$-$C_{10}$ aryl-O—CO— group which may be substituted, and a $C_6$-$C_{10}$ aryl-SO$_2$ group which may be substituted.

Among them, halogen atom, nitro group, cyano group, a $C_1$-$C_6$ alkyl group which may be substituted, a $C_6$-$C_{10}$ aryl group which may be substituted, a 5- to 10-membered heterocyclic group which may be substituted, a $C_1$-$C_6$ alkyl-CO— group which may be substituted, a $C_6$-$C_{10}$ aryl-CO— group which may be substituted, a $C_1$-$C_6$ alkyl-O—CO— group which may be substituted, a $C_6$-$C_{10}$ aryl-O—CO— group which may be substituted, and a $C_6$-$C_{10}$ aryl-SO$_2$ group which may be substituted are preferable.

An example of "the cyclic group which may be substituted" represented by $R^2$ includes a group represented by the following formula (II).

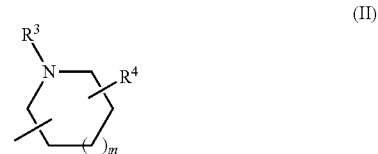

(II)

In formula (II), $R^3$ represents a group selected from the group consisting of the following (1) to (11):
(1) a $C_6$-$C_{10}$ aryl group which may be substituted;
(2) a $C_6$-$C_{10}$ aryl-SO$_2$— group which may be substituted on the aryl moiety;
(3) a $C_6$-$C_{10}$ aryl-$C_1$-$C_6$ alkyl group which may be substituted on the aryl moiety;
(4) a $C_6$-$C_{10}$ aryl-CO— group which may be substituted on the aryl moiety;
(5) a $C_6$-$C_{10}$ aryl-O—CO— group which may be substituted on the aryl moiety;
(6) a $C_6$-$C_{10}$ aryl-$C_1$-$C_6$ alkyl-O—CO— group which may be substituted on the aryl moiety;
(7) hydrogen atom;
(8) a $C_1$-$C_6$ alkyl-O—CO— group;
(9) a 5- to 10-membered heterocyclic group which may be substituted;
(10) a 5- or 6-membered aliphatic monocyclic-heterocyclic group which may be substituted;
(11) a 5- or 6-membered aliphatic monocyclic-heterocyclic-$C_1$-$C_6$ alkyl group which may be substituted on the heterocyclic moiety.

$R^4$ represents a group selected from the group consisting of hydrogen atom, a halogen atom, amino group, nitro group, hydroxy group, cyano group, a $C_1$-$C_6$ alkyl group, and, a $C_1$-$C_6$ alkyl-O— group.

The symbol "m" represents an integer of 0 to 2.

Provided that when L represents single bond, the binding position of Y to the group represented by formula (II) is a carbon atom that is not adjacent to the nitrogen atom.

The $C_6$-$C_{10}$ aryl moiety in each of the above (1) to (6) is preferably phenyl group.

When the aryl moiety in each of the above (1) to (6) is substituted, the aryl moiety is substituted by one or two groups independently selected from the group consisting of the following (i) to (viii):
(i) a 5- or 6-membered aliphatic monocyclic-heterocyclic-$C_1$-$C_6$ alkyl group, wherein the heterocyclic moiety may be substituted by a $C_1$-$C_6$ alkyl group, a $C_1$-$C_6$ alkyl-CO group, a $C_1$-$C_6$ alkyl-O—CO— group or oxo group. As the heterocyclic moiety, preferable examples include pyrrolidinyl group, morpholinyl group, piperidyl group, and piperazinyl group;
(ii) a 5- or 6-membered aliphatic monocyclic-heterocyclic group, which may be substituted by a $C_1$-$C_6$ alkyl group, a $C_1$-$C_6$ alkyl-CO— group or a $C_1$-$C_6$ alkyl-O—CO— group. A preferable example of the heterocyclic moiety includes piperazinyl group;
(iii) a halogen atom;
(iv) cyano group;
(v) a $C_1$-$C_6$ alkyl group which may be substituted by a 5- to 10-membered heterocyclic group.
As the heterocyclic group, a preferable example includes isoindolinyl group;
(vi) a $C_1$-$C_6$ alkyl-O— group;
(vii) a di($C_1$-$C_6$ alkyl)amino-$C_1$-$C_6$ alkyl group;
(viii) a 5- or 6-membered heteroaryl group.

An example of the 5- to 10-membered heterocyclic group in "the 5- to 10-membered heterocyclic group which may be substituted" of the above (9) includes a 5- to 10-membered monocyclic or bicyclic hetero group having as ring-constituting atom one or more carbon atoms and one to four hetero atoms selected from the group consisting of oxygen atom, sulfur atom, and nitrogen atom. As the 5- to 10-membered heterocyclic group, preferable examples include thiophenyl group, pyridyl group, pyrimidinyl group, pyrazinyl group, piperidyl group, isoindolinyl group, and benzoxazinyl group, more preferable examples include thiophenyl group, pyridyl group, pyrazinyl group, piperidyl group, isoindolinyl group, and benzoxazinyl group.

Examples of the substituents in "the 5- to 10-membered heterocyclic group which may be substituted" of the above (9) include the following (i) to (vi):
(i) a $C_1$-$C_6$ alkyl group,
(ii) a $C_1$-$C_6$ alkyl-CO— group,
(iii) a phenyl-$C_1$-$C_6$ alkyl group,
(iv) nitro group,
(v) oxo group, and
(vi) a $C_1$-$C_6$ alkyl-O— group.
Among the above substituents (i) to (vi), (i) a $C_1$-$C_6$ alkyl group, (ii) a $C_1$-$C_6$ alkyl-CO— group, (iii) a phenyl-$C_1$-$C_6$ alkyl group, (iv) nitro group, and (v) oxo group are preferable.

In "the 5- or 6-membered aliphatic mono-heterocyclic group which may be substituted" of the above (10), 4-piperidyl group is, for example, preferred as the 5- or 6-membered aliphatic monocyclic-heterocyclic group, and a $C_1$-$C_6$ alkyl group is, for example, preferred as the substituent.

In "the 5- or 6-membered aliphatic monocyclic-heterocycle-$C_1$-$C_6$ alkyl group which may be substituted on the cyclic moiety" of the above (11), 4-piperidyl group is, for example, preferred as the 5- or 6-membered aliphatic monocyclic-heterocyclic moiety, and a $C_1$-$C_6$ alkyl group or a phenyl-$C_1$-$C_6$ alkyl group is, for example, preferred as the substituent.

$R^4$ is preferably hydrogen atom.
The symbol "m" is preferably 0 to 1, and more preferably 1.
When $R^2$ is a group represented by formula (II), Y is preferably single bond.
When $R^2$ is a group represented by formula (II), L is preferably single bond or unsubstituted methylene group.
When $R^2$ is a group represented by formula (II) and each of L and Y is single bond, the binding position of Y (i.e., the binding position of the oxygen atom adjacent to L in formula (I)) to the group represented by formula (II) is preferably a carbon atom that is not adjacent to the nitrogen atom.

An example of "the cyclic group which may be substituted" represented by $R^2$ includes a group represented by formula (III).

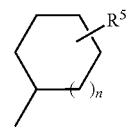

In formula (III), $R^5$ represents a group selected from the group consisting of hydrogen atom, a $C_1$-$C_6$ alkyl group, a $C_1$-$C_6$ alkyl-O— group, and a $C_6$-$C_{10}$ aryl group which may be substituted. Among them, hydrogen atom, a $C_1$-$C_6$ alkyl group, and a $C_6$-$C_{10}$ aryl group which may be substituted are preferable.

The symbol "n" represents an integer of 0 or 1.

In "the $C_6$-$C_{10}$ aryl group which may be substituted" represented by $R^5$, examples of the substituents include a $C_1$-$C_6$ alkyl group which may be substituted by hydroxy group, and a 5- or 6-membered aliphatic monocyclic-heterocyclic-$C_1$-$C_6$ alkyl group which may be substituted by a $C_1$-$C_6$ alkyl group on the heterocyclic moiety. The heterocyclic moiety is preferably piperazinyl group.

When $R^2$ is a group represented by formula (III), Y is preferably single bond.
When $R^2$ is a group represented by formula (III), L is preferably single bond.
When $R^2$ is a pyridyl group or a phenyl group which may have 1 to 3 substituents which are the same or different and selected from the group consisting of a halogen atom, a $C_1$-$C_6$ alkyl group, a $C_1$-$C_6$ alkyl-O— group, a di($C_1$-$C_6$ alkyl) amino-$C_1$-$C_6$ alkyl group, and a 5- or 6-membered aliphatic monocyclic-heterocyclic-$C_1$-$C_6$ alkyl group. Among them, a halogen atom, a $C_1$-$C_6$ alkyl group, a di($C_1$-$C_6$ alkyl)amino-$C_1$-$C_6$ alkyl group, and a 5- or 6-membered aliphatic monocyclic-heterocyclic-$C_1$-$C_6$ alkyl group are preferable.

In the 5- or 6-membered aliphatic monocyclic-heterocyclic-$C_1$-$C_6$ alkyl group, the heterocyclic moiety is preferably piperidyl group.

Preferable examples of the compound of the present invention include:
1-Methyl-2-(1-phenyl-piperidin-3-yloxy)-1H-[4,4']bipyrimidinyl-6-one,
2-[1-(3-Fluoro-phenyl)piperidin-3-yloxy]-1-methyl-1H-[4,4']bipyrimidinyl-6-one,
2-[1-(3-Methoxy-phenyl)piperidin-3-yloxy]-1-methyl-1H-[4,4']bipyrimidinyl-6-one,
1-Methyl-2-(1-pyridin-2-yl-piperidin-3-yloxy)-1H-[4,4']bipyrimidinyl-6-one,
2-[(2S)-1-(4-Fluoro-phenyl)pyrrolidin-2-ylmethoxy]-6-(3-fluoro-pyridin-4-yl)-3-methyl-3H-pyrimidin-4-one,
tert-Butyl 4-{4-[4-(1-methyl-6-oxo-1,6-dihydro-[4,4']bipyrimidinyl-2-yloxy)piperidin-1-yl]benzyl}piperazine-1-carboxylate,
1-Methyl-2-[1-(4-piperazin-1-ylmethyl-phenyl)piperidin-4-yloxy]-1H-[4,4']bipyrimidinyl-6-one,
1-Methyl-2-[1-(4-morpholin-4-ylmethyl-phenyl)piperidin-4-yloxy]-1H-[4,4']bipyrimidinyl-6-one,
1-Methyl-2-{1-[4-(4-methyl-piperazin-1-ylmethyl)phenyl]piperidin-4-yloxy}-1H-[4,4']bipyrimidinyl-6-one,
1-Methyl-2-[1-(4-piperazin-1-yl-phenyl)piperidin-4-yloxy]-1H-[4,4']bipyrimidinyl-6-one,
1-Methyl-2-{1-[4-(4-methyl-piperazin-1-yl)phenyl]piperidin-4-yloxy}-1H-[4,4']bipyrimidinyl-6-one, 1-Methyl-2-[1-(4-piperidin-1-ylmethyl-phenyl)piperidin-4-yloxy]-1H-[4,4']bipyrimidinyl-6-one,
1-Methyl-2-[1-(4-pyrrolidin-1-ylmethyl-phenyl)piperidin-4-yloxy]-1H-[4,4']bipyrimidinyl-6-one,
2-{1-[4-(1,3-Dihydro-isoindol-2-ylmethyl)phenyl]piperidin-4-yloxy}-1-methyl-1H-[4,4]bipyrimidinyl-6-one,
1-Methyl-2-[1-(3-piperidin-1-ylmethyl-phenyl)piperidin-4-yloxy]-1H-[4,4']bipyrimidinyl-6-one,
1-Methyl-2-{1-[2-(4-methyl-piperazin-1-ylmethyl)phenyl]piperidin-4-yloxy}-1H-[4,4']bipyrimidinyl-6-one,
6-(3-Fluoro-pyridin-4-yl)-3-methyl-2-[1-(4-piperidin-1-ylmethyl-phenyl)piperidin-4-ylmethoxy]-3H-pyrimidin-4-one,
6-(3-Fluoro-pyridin-4-yl)-3-methyl-2-[1-(4-piperidin-1-ylmethyl-phenyl)piperidin-4-yloxy]-3H-pyrimidin-4-one,
1-Methyl-2-[1-(4-piperidin-1-ylmethyl-phenyl)pyrrolidin-3-yloxy]-1H-[4,4']bipyrimidinyl-6-one,
1-Methyl-2-{cis-4-[4-(4-methyl-piperazin-1-ylmethyl)phenyl]cyclohexyloxy}-1H-[4,4']bipyrimidinyl-6-one,
1-Methyl-2-{trans-4-[4-(4-methyl-piperazin-1-ylmethyl)phenyl]cyclohexyloxy}-1H-[4,4']bipyrimidinyl-6-one,
2-[1-(2,3-Dihydro-1H-isoindol-5-yl)piperidin-4-yloxy]-1-methyl-1H-[4,4']bipyrimidinyl-6-one, and
2-[1-(2-Benzyl-2,3-dihydro-1H-isoindol-5-yl)piperidin-4-yloxy]-1-methyl-1H-[4,4']bipyrimidinyl-6-one.

A pharmaceutically acceptable salt of any of the above compounds is also preferable.

The pharmaceutically acceptable salt of the compound represented by the aforementioned formula (I) may include the salt with inorganic acid such as hydrochloric acid, hydrobromic acid and the like and the salt with organic acid such as acetic acid, propionic acid, tartaric acid, fumaric acid, maleic acid, malic acid, oxalic acid, succinic acid, citric acid, benzoic acid and the like.

In addition to the compound represented by the aforementioned formula (I), an optically active isomer thereof, or a pharmaceutically acceptable salt thereof, their solvates and hydrates also fall within the scope of the present invention. The compound represented by the formula (I) may have one or more asymmetric carbon atoms. As for the stereochemistry of such asymmetric carbon atoms, they may independently be in either (R) or (S) configuration, and the pyrimidone derivative may exist as stereoisomers such as optical isomers, or diastereoisomers. Any stereoisomers of pure form, any mixtures of stereoisomers, racemates and the like fall within the scope of the present invention Examples of preferred compounds of the present invention are shown in the tables set out below. However, the scope of the present invention is not limited by the following compounds.

TABLE 1

| COMPOUND NO. | STRUCTURE | COMPOUND NAME |
| --- | --- | --- |
| 1.101 | 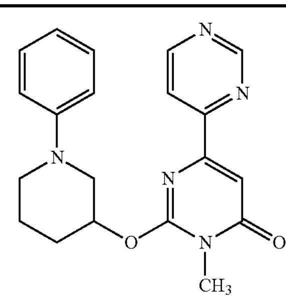 | 1-Methyl-2-(1-phenyl-piperidin-3-yloxy)-1H-[4,4']bipyrimidinyl-6-one |
| 1.102 | 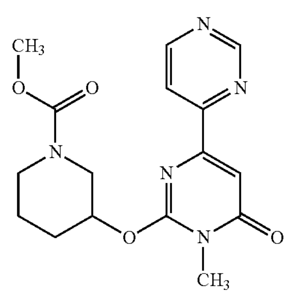 [SMILES: COC(=O)N1CCCC(Oc2nc(-c3ccncn3)cc(=O)n2C)C1] | Methyl 3-(1-methyl-6-oxo-1,6-dihydro-[4,4']bipyrimidinyl-2-yloxy)piperidine-1-carboxylate |
| 1.103 | 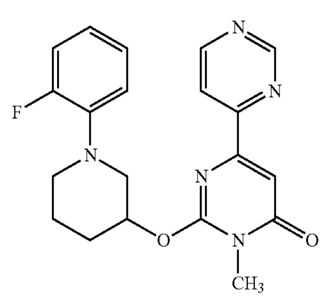 [SMILES: Cn1c(OC2CCCN(c3ccccc3F)C2)nc(-c2ccncn2)cc1=O] | 2-[1-(2-Fluoro-phenyl)piperidin-3-yloxy]-1-methyl-1H-[4,4']bipyrimidinyl-6-one |

TABLE 1-continued

| COMPOUND NO. | STRUCTURE | COMPOUND NAME |
| --- | --- | --- |
| 1.104 | 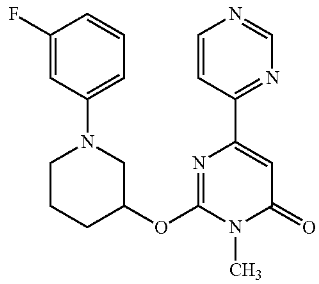 [SMILES: Cn1c(OC2CCCN(c3cccc(F)c3)C2)nc(-c2ccncn2)cc1=O] | 2-[1-(3-Fluoro-phenyl)piperidin-3-yloxy]-1-methyl-1H-[4,4']bipyrimidinyl-6-one |
| 1.105 | 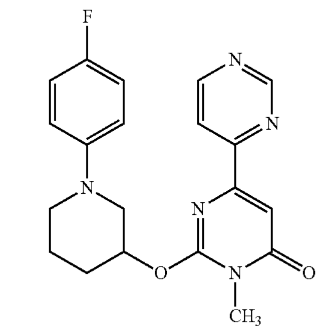 [SMILES: Cn1c(OC2CCCN(c3ccc(F)cc3)C2)nc(-c2ccncn2)cc1=O] | 2-[1-(4-Fluoro-phenyl)piperidin-3-yloxy]-1-methyl-1H-[4,4']bipyrimidinyl-6-one |
| 1.106 | 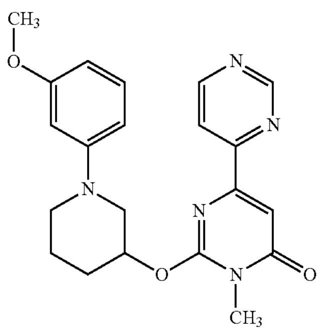 [SMILES: COc1cccc(N2CCCC(Oc3nc(-c4ccncn4)cc(=O)n3C)C2)c1] | 2-[1-(3-Methoxy-phenyl)piperidin-3-yloxy]-1-methyl-1H-[4,4']bipyrimidinyl-6-one |
| 1.107 | 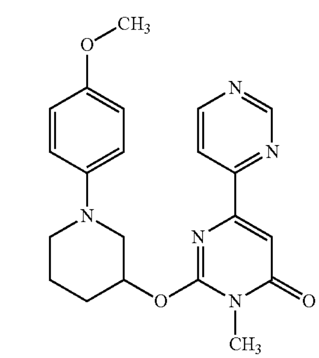 [SMILES: COc1ccc(N2CCCC(Oc3nc(-c4ccncn4)cc(=O)n3C)C2)cc1] | 2-[1-(4-Methoxy-phenyl)piperidin-3-yloxy]-1-methyl-1H-[4,4']bipyrimidinyl-6-one |
| 1.108 | 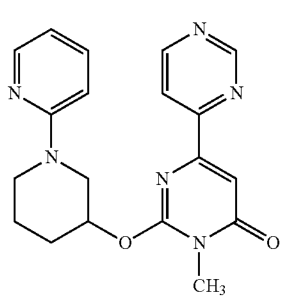 [SMILES: Cn1c(OC2CCCN(c3ccccn3)C2)nc(-c2ccncn2)cc1=O] | 1-Methyl-2-(1-pyridin-2-yl-piperidin-3-yloxy)-1H-[4,4']bipyrimidinyl-6-one |

TABLE 1-continued

| COMPOUND NO. | STRUCTURE | COMPOUND NAME |
|---|---|---|
| 1.109 | 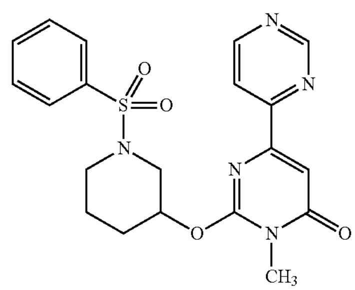 [SMILES: Cn1c(OC2CCCN(S(=O)(=O)c3ccccc3)C2)nc(-c2ccncn2)cc1=O] | 2-(1-Benzenesulfonyl-piperidin-3-yloxy)-1-methyl-1H-[4,4']bipyrimidinyl-6-one |
| 1.110 | 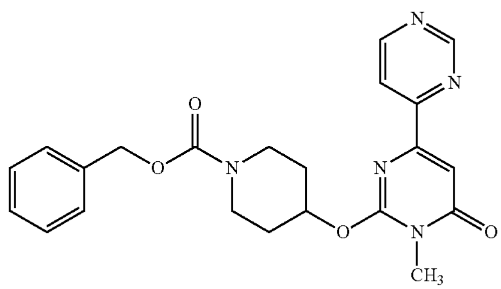 [SMILES: Cn1c(OC2CCN(C(=O)OCc3ccccc3)CC2)nc(-c2ccncn2)cc1=O] | Benzyl 4-(1-methyl-6-oxo-1,6-dihydro-[4,4']bipyrimidinyl-2-yloxy)piperidine-1-carboxylate |
| 1.111 | 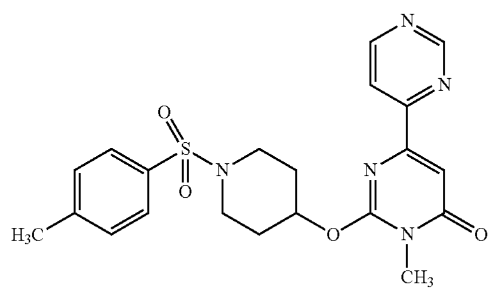 [SMILES: Cc1ccc(S(=O)(=O)N2CCC(Oc3nc(-c4ccncn4)cc(=O)n3C)CC2)cc1] | 1-Methyl-2-[1-(toluene-4-sulfonyl)piperidin-4-yloxy]-1H-[4,4']bipyrimidinyl-6-one |
| 1.112 | 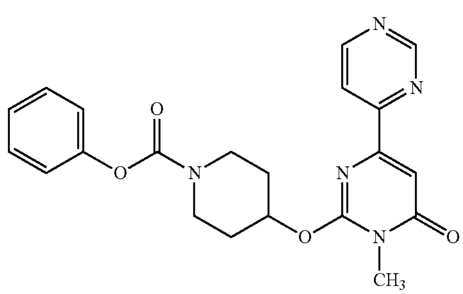 [SMILES: Cn1c(OC2CCN(C(=O)Oc3ccccc3)CC2)nc(-c2ccncn2)cc1=O] | Phenyl 4-(1-methyl-6-oxo-1,6-dihydro-[4,4']bipyrimidinyl-2-yloxy)piperidine-1-carboxylate |
| 1.201 | 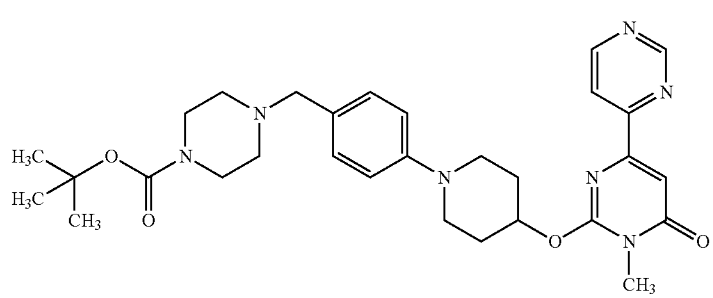 [SMILES: Cn1c(OC2CCN(c3ccc(CN4CCN(C(=O)OC(C)(C)C)CC4)cc3)CC2)nc(-c2ccncn2)cc1=O] | tert-Butyl 4-{4-[4-(1-methyl-6-oxo-1,6-dihydro-[4,4']bipyrimidinyl-2-yloxy)piperidin-1-yl]benzyl}piperazine-1-carboxylate |

TABLE 1-continued

| COMPOUND NO. | STRUCTURE | COMPOUND NAME |
| --- | --- | --- |
| 1.202 | 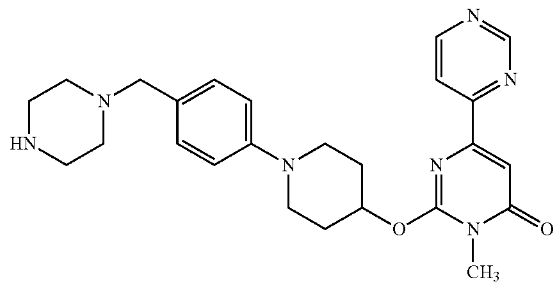 [SMILES: Cn1c(OC2CCN(c3ccc(CN4CCNCC4)cc3)CC2)nc(-c2ccncn2)cc1=O] | 1-Methyl-2-[1-(4-piperazin-1-yl methyl-phenyl)piperidin-4-yloxy]-1H-[4,4']bipyrimidinyl-6-one |
| 1.203 | 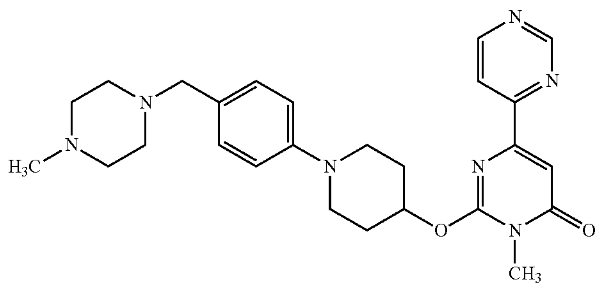 [SMILES: CN1CCN(Cc2ccc(N3CCC(Oc4nc(-c5ccncn5)cc(=O)n4C)CC3)cc2)CC1] | 1-Methyl-2-{1-[4-(4-methyl-piperazin-1-ylmethyl)phenyl]piperidin-4-yloxy}-1H-[4,4']bipyrimidinyl-6-one |
| 1.204 | 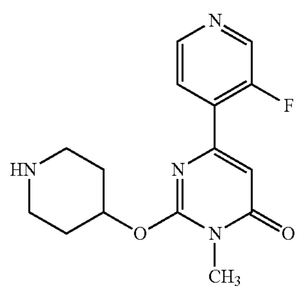 [SMILES: Cn1c(OC2CCNCC2)nc(-c2ccncc2F)cc1=O] | 6-(3-Fluoro-pyridin-4-yl)-3-methyl-2-(piperidin-4-yloxy)-3H-pyrimidin-4-one |
| 1.205 | 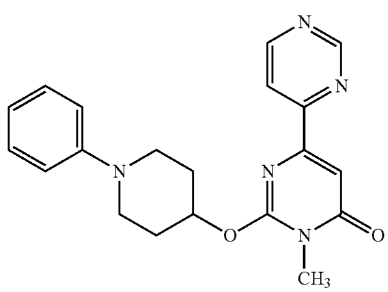 [SMILES: Cn1c(OC2CCN(c3ccccc3)CC2)nc(-c2ccncn2)cc1=O] | 1-Methyl-2-(1-phenyl-piperidin-4-yloxy)-1H-[4,4']bipyrimidinyl-6-one |
| 1.206 | 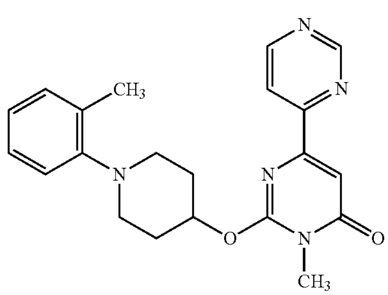 [SMILES: Cc1ccccc1N1CCC(Oc2nc(-c3ccncn3)cc(=O)n2C)CC1] | 1-Methyl-2-(1-o-tolyl-piperidin-4-yloxy)-1H-[4,4']bipyrimidinyl-6-one |

TABLE 1-continued

| COMPOUND NO. | STRUCTURE | COMPOUND NAME |
| --- | --- | --- |
| 1.207 | 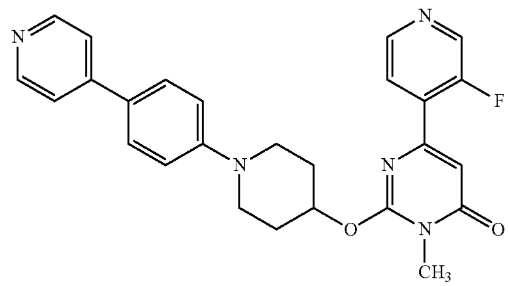 [SMILES: Cn1c(OC2CCN(c3ccc(-c4ccncc4)cc3)CC2)nc(-c2ccncc2F)cc1=O] | 6-(3-Fluoro-pyridin-4-yl)-3-methyl-2-[1-(4-pyridin-4-yl-phenyl)piperidin-4-yloxy]-3H-pyrimidin-4-one |
| 1.208 | 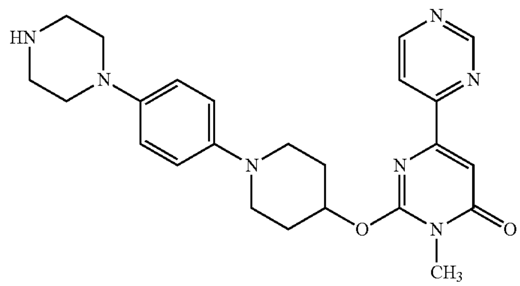 [SMILES: Cn1c(OC2CCN(c3ccc(N4CCNCC4)cc3)CC2)nc(-c2ccncn2)cc1=O] | 1-Methyl-2-[1-(4-piperazin-1-yl-phenyl)-piperidin-4-yloxy]-1H-[4,4']bipyrimidinyl-6-one |
| 1.209 | 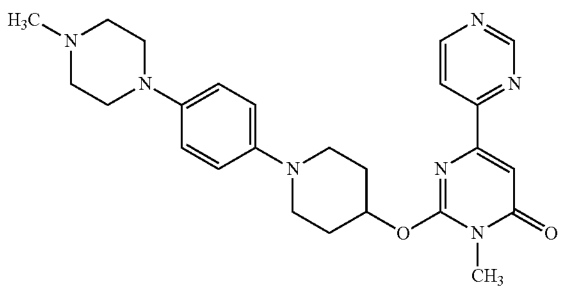 [SMILES: CN1CCN(c2ccc(N3CCC(Oc4nc(-c5ccncn5)cc(=O)n4C)CC3)cc2)CC1] | 1-Methyl-2-{1-[4-(4-methyl-piperazin-1-yl)phenyl]piperidin-4-yloxy}-1H-[4,4']bipyrimidinyl-6-one |
| 1.210 | 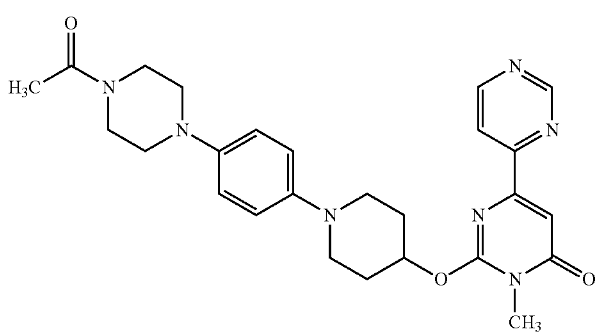 [SMILES: CC(=O)N1CCN(c2ccc(N3CCC(Oc4nc(-c5ccncn5)cc(=O)n4C)CC3)cc2)CC1] | 2-{1-[4-(4-Acetyl-piperazin-1-yl)phenyl]piperidin-4-yloxy}-1-methyl-1H-[4,4']bipyrimidinyl-6-one |
| 1.211 | 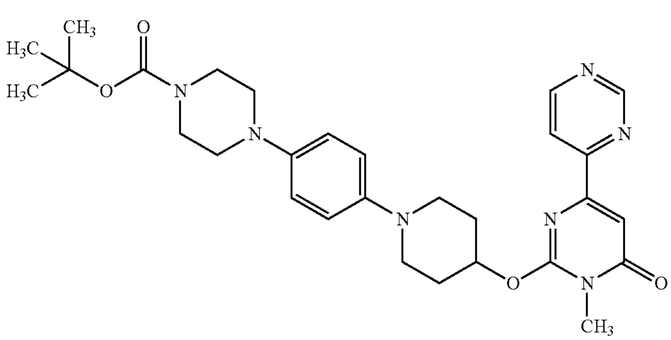 [SMILES: Cn1c(OC2CCN(c3ccc(N4CCN(C(=O)OC(C)(C)C)CC4)cc3)CC2)nc(-c2ccncn2)cc1=O] | tert-Butyl 4-{4-[4-(1-methyl-6-oxo-1,6-dihydro-[4,4']bipyrimidinyl-2-yloxy)piperidin-1-yl]phenyl}piperazine-1-carboxylate |

TABLE 1-continued

| COMPOUND NO. | STRUCTURE | COMPOUND NAME |
|---|---|---|
| 1.212 | 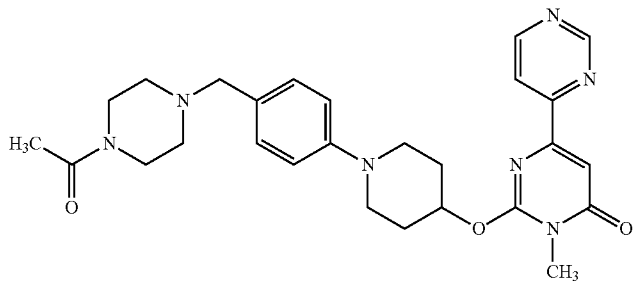 [SMILES: CC(=O)N1CCN(Cc2ccc(N3CCC(Oc4nc(-c5ccncn5)cc(=O)n4C)CC3)cc2)CC1] | 2-{1-[4-(4-Acetyl-piperazin-1-yl methyl)phenyl]piperidn-4-yloxy}-1-methyl-1H-[4,4']bipyrimidinyl-6-one |
| 1.213 | 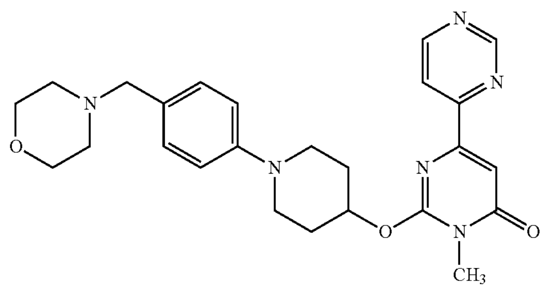 [SMILES: Cn1c(OC2CCN(c3ccc(CN4CCOCC4)cc3)CC2)nc(-c2ccncn2)cc1=O] | 1-Methyl-2-[1-(4-morpholin-4-yl methyl-phenyl)piperidin-4-yloxy]-1H-[4,4']bipyrimidinyl-6-one |
| 1.214 | 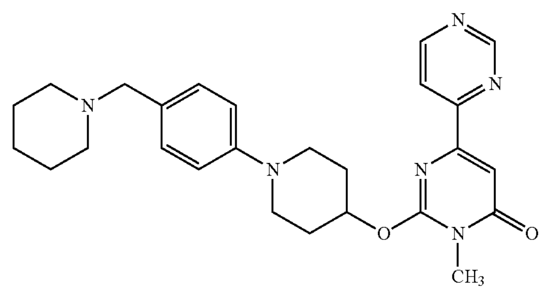 | 1-Methyl-2-[1-(4-piperidin-1-ylmethyl-phenyl)piperidin-4-yloxy]-1H-[4,4']bipyrimidinyl-6-one |
| 1.215 | 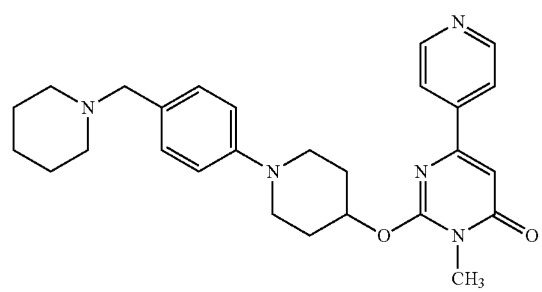 | 3-Methyl-2-[1-(4-piperidin-1-ylmethyl-phenyl)piperidin-4-yloxy]-6-pyridin-4-yl-3H-pyrimidin-4-one |
| 1.216 | 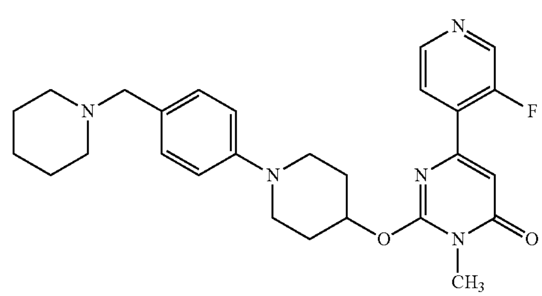 [SMILES: Cn1c(OC2CCN(c3ccc(CN4CCCCC4)cc3)CC2)nc(-c2ccncc2F)cc1=O] | 6-(3-Fluoro-pyridin-4-yl)-3-methyl-2-[1-(4-piperidin-1-ylmethyl-phenyl)piperidin-4-yloxy]-3H-pyrimidin-4-one |

TABLE 1-continued

| COMPOUND NO. | STRUCTURE | COMPOUND NAME |
|---|---|---|
| 1.217 | 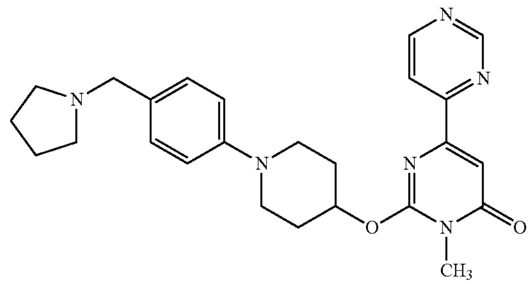 [SMILES: Cn1c(OC2CCN(c3ccc(CN4CCCC4)cc3)CC2)nc(-c2ccncn2)cc1=O] | 1-Methyl-2-[1-(4-pyrrolidin-1-yl methyl-phenyl)piperidin-4-yloxy]-1H-[4,4']bipyrimidinyl-6-one |
| 1.218 | 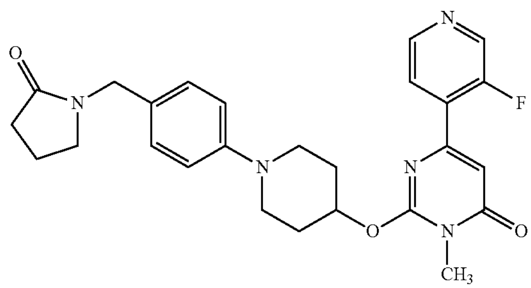 [SMILES: Cn1c(OC2CCN(c3ccc(CN4CCCC4=O)cc3)CC2)nc(-c2ccncc2F)cc1=O] | 6-(3-Fluoro-pyridin-4-yl)-3-methyl-2-{1-[4-(2-oxo-pyrrolidin-1-yl methyl)phenyl]piperidin-4-yloxy}-3H-pyrimidin-4-one |
| 1.219 | 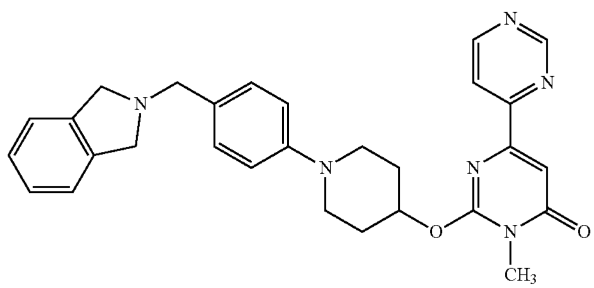 [SMILES: Cn1c(OC2CCN(c3ccc(CN4Cc5ccccc5C4)cc3)CC2)nc(-c2ccncn2)cc1=O] | 2-{1-[4-(1,3-Dihydro-isoindol-2-ylmethyl)phenyl]piperidin-4-yloxy}-1-methyl-1H-[4,4']bipyrimidinyl-6-one |
| 1.220 | 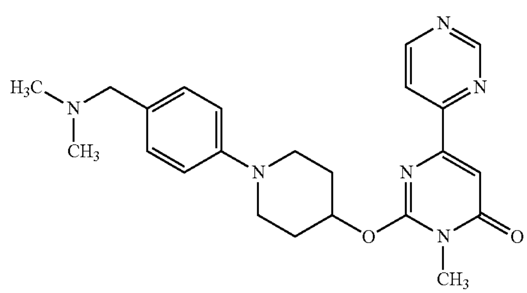 [SMILES: CN(C)Cc1ccc(N2CCC(Oc3nc(-c4ccncn4)cc(=O)n3C)CC2)cc1] | 2-[1-(4-Dimethylaminomethyl-phenyl)piperidin-4-yloxy]-1-methyl-1H-[4,4']bipyrimidinyl-6-one |
| 1.221 | 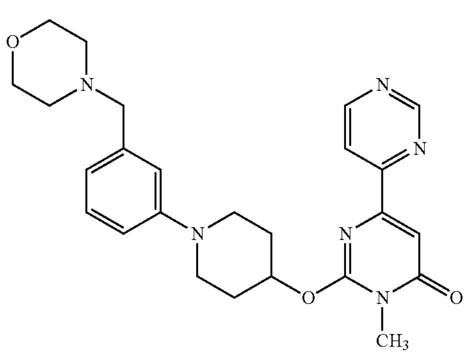 [SMILES: Cn1c(OC2CCN(c3cccc(CN4CCOCC4)c3)CC2)nc(-c2ccncn2)cc1=O] | 1-Methyl-2-[1-(3-morpholin-4-yl methyl-phenyl)piperidin-4-yloxy]-1H-[4,4']bipyrimidinyl-6-one |

TABLE 1-continued

| COMPOUND NO. | STRUCTURE | COMPOUND NAME |
| --- | --- | --- |
| 1.222 | 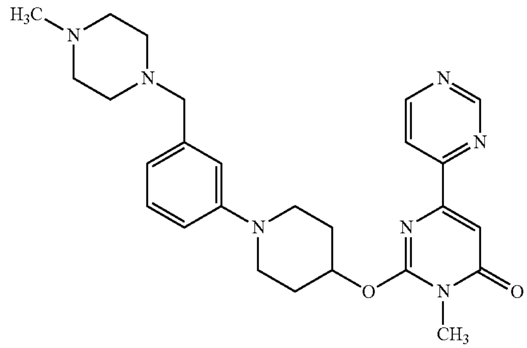 [SMILES: CN1CCN(Cc2cccc(N3CCC(Oc4nc(-c5ccncn5)cc(=O)n4C)CC3)c2)CC1] | 1-Methyl-2-{1-[3-(4-methyl-piperazin-1-ylmethyl)phenyl]piperidin-4-yloxy}-1H-[4,4']bipyrimidinyl-6-one |
| 1.223 | 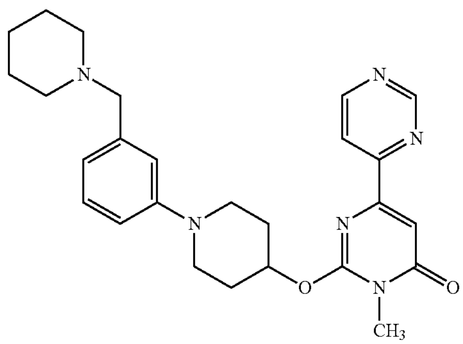 [SMILES: Cn1c(OC2CCN(c3cccc(CN4CCCCC4)c3)CC2)nc(-c2ccncn2)cc1=O] | 1-Methyl-2-[1-(3-piperidin-1-ylmethyl-phenyl)piperidin-4-yloxy]-1H-[4,4']bipyrimidinyl-6-one |
| 1.224 | 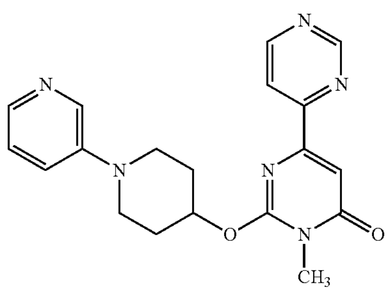 | 1-Methyl-2-(1-pyridin-3-yl-piperidin-4-yloxy)-1H-[4,4']bipyrimidinyl-6-one |
| 1.225 | 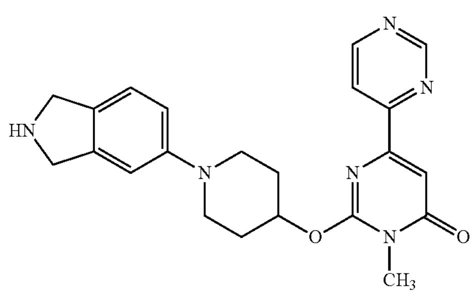 [SMILES: Cn1c(OC2CCN(c3ccc4c(c3)CNC4)CC2)nc(-c2ccncn2)cc1=O] | 2-[1-(2,3-Dihydro-1H-isoindol-5-yl)piperidin-4-yloxy]-1-methyl-1H-[4,4']bipyrimidinyl-6-one |
| 1.226 | 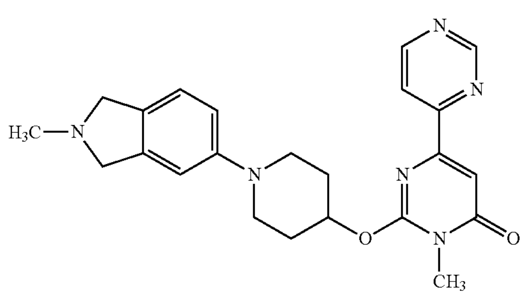 [SMILES: CN1Cc2ccc(N3CCC(Oc4nc(-c5ccncn5)cc(=O)n4C)CC3)cc2C1] | 1-Methyl-2-[1-(2-methyl-2,3-dihydro-1H-isoindol-5-yl)piperidin-4-yloxy]-1H-[4,4']bipyrimidinyl-6-one |

TABLE 1-continued

| COMPOUND NO. | STRUCTURE | COMPOUND NAME |
|---|---|---|
| 1.227 | 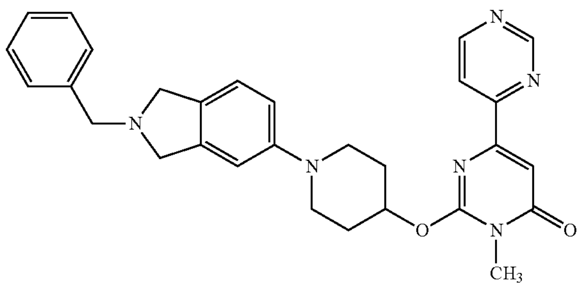 [SMILES: Cn1c(OC2CCN(c3ccc4c(c3)CN(Cc3ccccc3)C4)CC2)nc(-c2ccncn2)cc1=O] | 2-[1-(2-Benzyl-2,3-dihydro-1H-isoindol-5-yl)piperidin-4-yloxy]-1-methyl-1H-[4,4']bipyrimidinyl-6-one |
| 1.228 | 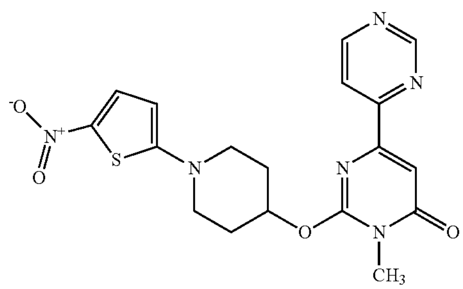 | 1-Methyl-2-[1-(5-nitro-thiophen-2-yl)piperidin-4-yloxy]-1H-[4,4']bipyrimidinyl-6-one |
| 1.229 | 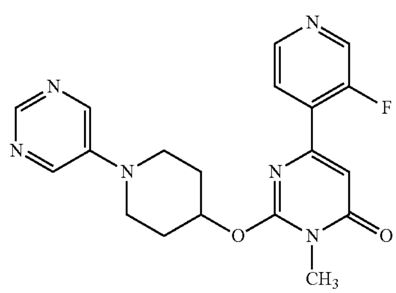 [SMILES: Cn1c(OC2CCN(c3cncnc3)CC2)nc(-c2ccncc2F)cc1=O] | 6-(3-Fluoro-pyridin-4-yl)-3-methyl-2-(1-pyrimidin-5-yl-piperidin-4-yloxy)-3H-pyrimidin-4-one |
| 1.230 | 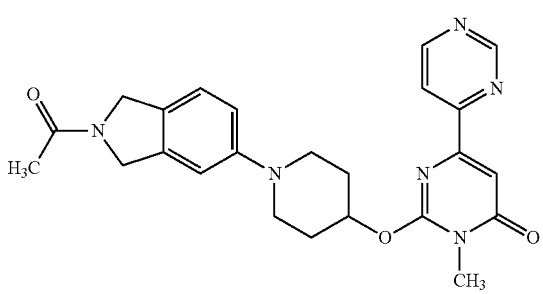 [SMILES: CC(=O)N1Cc2ccc(N3CCC(Oc4nc(-c5ccncn5)cc(=O)n4C)CC3)cc2C1] | 2-[1-(2-Acetyl-2,3-dihydro-1H-isoindol-5-yl)piperidin-4-yloxy]-1-methyl-1H-[4,4']bipyrimidinyl-6-one |
| 1.231 | 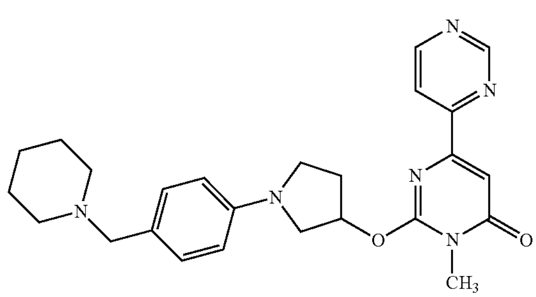 [SMILES: Cn1c(OC2CCN(c3ccc(CN4CCCCC4)cc3)C2)nc(-c2ccncn2)cc1=O] | 1-Methyl-2-[1-(4-piperidin-1-ylmethyl-phenyl)pyrrolidin-3-yloxy]-1H-[4,4']bipyrimidinyl-6-one |

TABLE 1-continued

| COMPOUND NO. | STRUCTURE | COMPOUND NAME |
| --- | --- | --- |
| 1.232 | 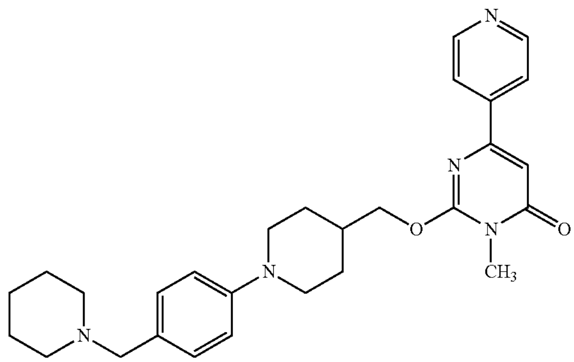 [SMILES: Cn1c(OCC2CCN(c3ccc(CN4CCCCC4)cc3)CC2)nc(-c2ccncc2)cc1=O] | 3-Methyl-2-[1-(4-piperidin-1-ylmethyl-phenyl)piperidin-4-ylmethoxy]-6-pyridin-4-yl-3H-pyrimidin-4-one |
| 1.233 | 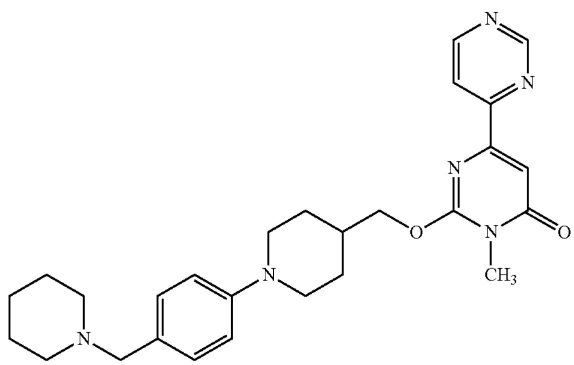 [SMILES: Cn1c(OCC2CCN(c3ccc(CN4CCCCC4)cc3)CC2)nc(-c2ccncn2)cc1=O] | 1-Methyl-2-[1-(4-piperidin-1-ylmethyl-phenyl)piperidin-4-ylmethoxy]-1H-[4,4']bipyrimidinyl-6-one |
| 1.234 | 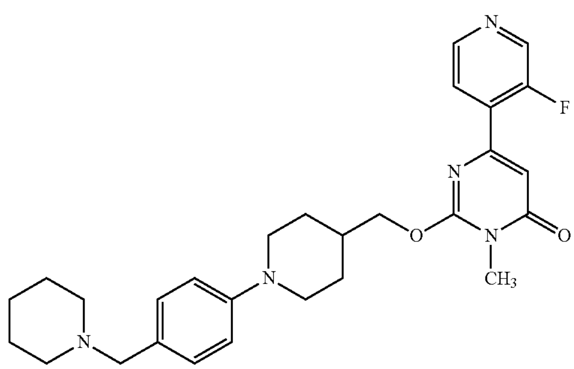 [SMILES: Cn1c(OCC2CCN(c3ccc(CN4CCCCC4)cc3)CC2)nc(-c2ccncc2F)cc1=O] | 6-(3-Fluoro-pyridin-4-yl)-3-methyl-2-[1-(4-piperidin-1-ylmethyl-phenyl)piperidin-4-ylmethoxy]-3H-pyrimidin-4-one |
| 1.301 | 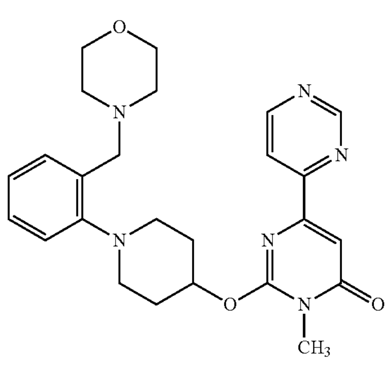 [SMILES: Cn1c(OC2CCN(c3ccccc3CN3CCOCC3)CC2)nc(-c2ccncn2)cc1=O] | 1-Methyl-2-[1-(2-morpholin-4-yl methyl-phenyl)piperidin-4-yloxy]-1H-[4,4']bipyrimidinyl-6-one |

TABLE 1-continued

| COMPOUND NO. | STRUCTURE | COMPOUND NAME |
| --- | --- | --- |
| 1.302 | 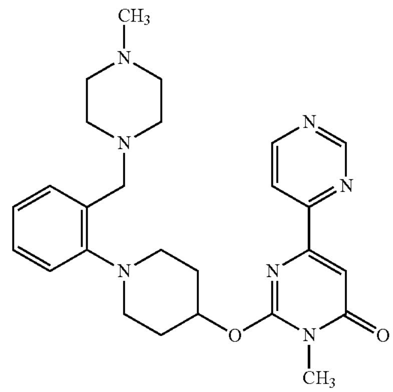 [SMILES: CN1CCN(Cc2ccccc2N2CCC(Oc3nc(-c4ccncn4)cc(=O)n3C)CC2)CC1] | 1-Methyl-2-{1-[2-(4-methyl-piperazin-1-ylmethyl)phenyl]piperidin-4-yloxy}-1H-[4,4']bipyrimidinyl-6-one |
| 1.303 | 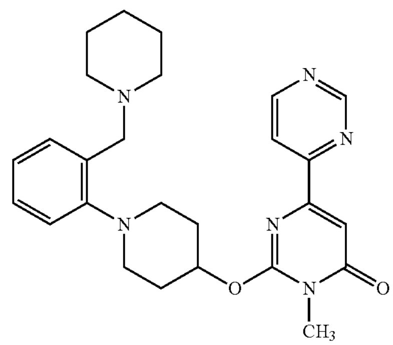 [SMILES: Cn1c(OC2CCN(c3ccccc3CN3CCCCC3)CC2)nc(-c2ccncn2)cc1=O] | 1-Methyl-2-[1-(2-piperidin-1-ylmethyl-phenyl)piperidin-4-yloxy]-1H-[4,4']bipyrimidinyl-6-one |
| 1.304 | 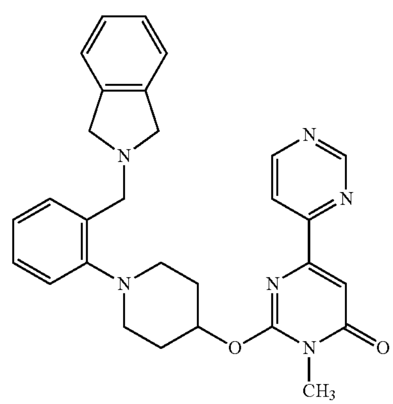 [SMILES: Cn1c(OC2CCN(c3ccccc3CN3Cc4ccccc4C3)CC2)nc(-c2ccncn2)cc1=O] | 2-{1-[2-(1,3-Dihydro-isoindol-2-ylmethyl)phenyl]piperidin-4-yloxy}-1-methyl-1H-[4,4']bipyrimidinyl-6-one |
| 1.305 | 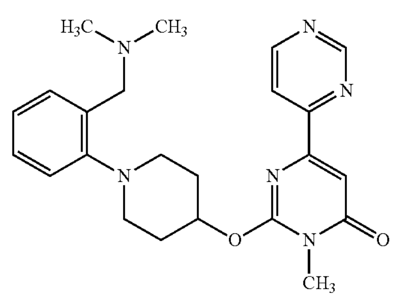 [SMILES: CN(C)Cc1ccccc1N1CCC(Oc2nc(-c3ccncn3)cc(=O)n2C)CC1] | 2-[1-(2-Dimethylaminomethyl-phenyl)piperidin-4-yloxy]-1-methyl-1H-[4,4']bipyrimidinyl-6-one |

TABLE 1-continued

| COMPOUND NO. | STRUCTURE | COMPOUND NAME |
| --- | --- | --- |
| 1.401 | 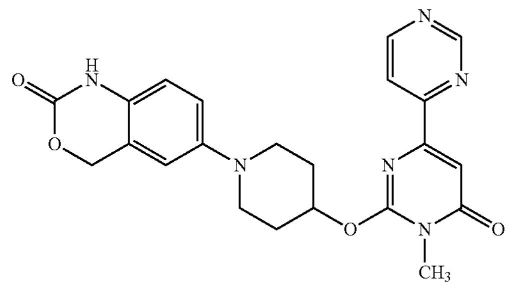 [SMILES: Cn1c(OC2CCN(c3ccc4c(c3)COC(=O)N4)CC2)nc(-c2ccncn2)cc1=O] | 1-Methyl-2-{[1-(2-oxo-1,4-dhydro-2H-3,1-benzoxazin-6-yl)piperidin-4-yl]oxy}-1H-[4,4']bipyrimidinyl-6-one |
| 1.501 | 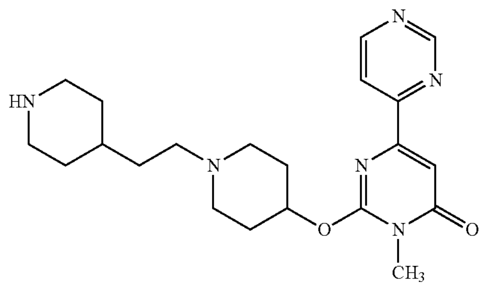 [SMILES: Cn1c(OC2CCN(CCC3CCNCC3)CC2)nc(-c2ccncn2)cc1=O] | 1-Methyl-2-[1-(2-piperidin-4-yl-ethyl)piperidin-4-yloxy]-1H-[4,4']bipyrimidinyl-6-one |
| 1.502 | 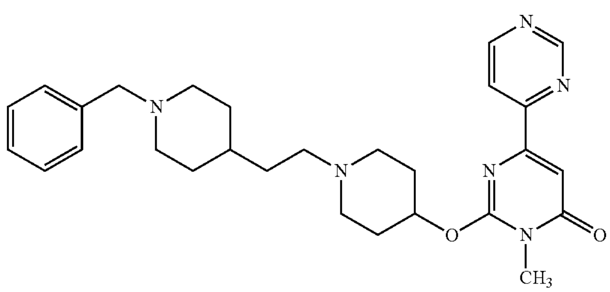 [SMILES: Cn1c(OC2CCN(CCC3CCN(Cc4ccccc4)CC3)CC2)nc(-c2ccncn2)cc1=O] | 2-{1-[2-(1-Benzyl-piperidin-4-yl)ethyl]piperidin-4-yloxy}-1-methyl-1H-[4,4']bipyrimidinyl-6-one |
| 1.503 | 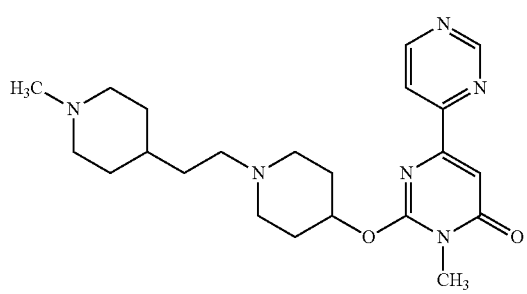 [SMILES: CN1CCC(CCN2CCC(Oc3nc(-c4ccncn4)cc(=O)n3C)CC2)CC1] | 1-Methyl-2-{1-[2-(1-methyl-piperidin-4-yl)ethyl]piperidin-4-yloxy)-1H-[4,4']bipyrimidinyl-6-one |
| 1.504 | 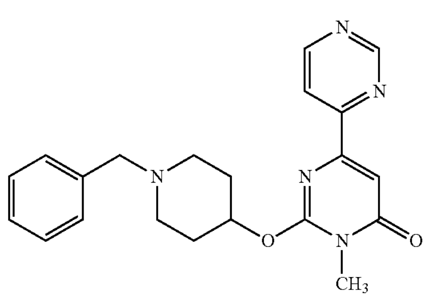 [SMILES: Cn1c(OC2CCN(Cc3ccccc3)CC2)nc(-c2ccncn2)cc1=O] | 2-(1-Benzyl-piperidin-4-yloxy)-1-methyl-1H-[4,4']bipyrimidinyl-6-one |

TABLE 1-continued

| COMPOUND NO. | STRUCTURE | COMPOUND NAME |
| --- | --- | --- |
| 1.505 | 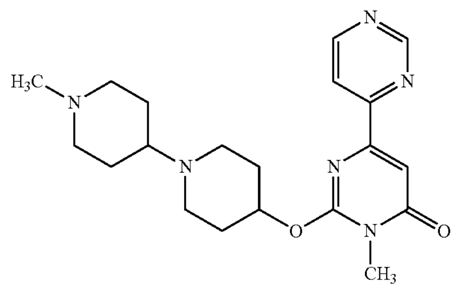 [SMILES: CN1CCC(N2CCC(Oc3nc(-c4ccncn4)cc(=O)n3C)CC2)CC1] | 1-Methyl-2-(1'-methyl-[1,4'] bipiperidinyl-4-yloxy)-1H-[4,4'] bipyrimidinyl-6-one |
| 1.601 | 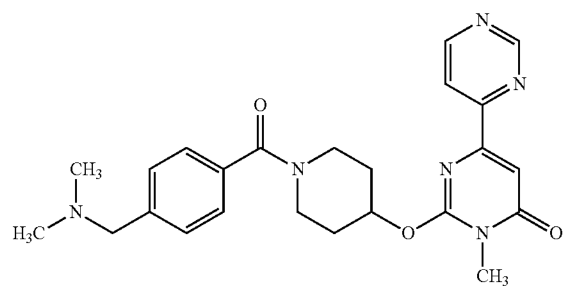 [SMILES: CN(C)Cc1ccc(C(=O)N2CCC(Oc3nc(-c4ccncn4)cc(=O)n3C)CC2)cc1] | 2-[1-(4-Dimethylaminomethyl-benzoyl)piperidin-4-yloxy]-1-methyl-1H-[4,4']bipyrimidinyl-6-one |
| 1.701 | 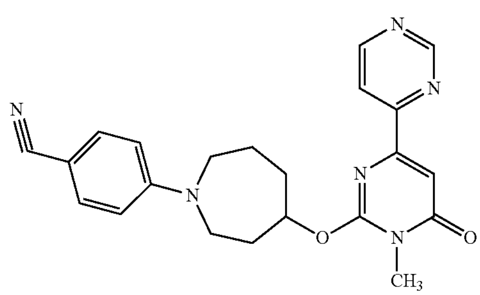 [SMILES: Cn1c(OC2CCCN(c3ccc(C#N)cc3)CC2)nc(-c2ccncn2)cc1=O] | 4-[4-(1-Methyl-6-oxo-1,6-dihydro-[4,4']bipyrimidinyl-2-yloxy)azepan-1-yl]benzonitrile |
| 1.801 | 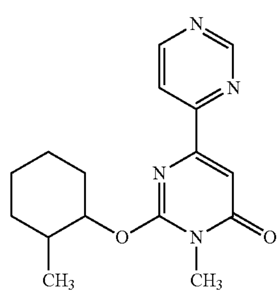 [SMILES: CC1CCCCC1Oc1nc(-c2ccncn2)cc(=O)n1C] | 1-Methyl-2-(2-methyl-cyclohexyloxy)-1H-[4,4'] bipyrimidinyl-6-one |
| 1.802 | 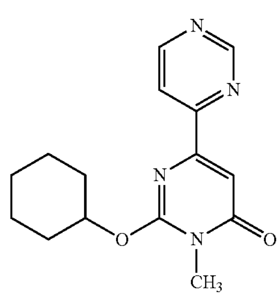 [SMILES: Cn1c(OC2CCCCC2)nc(-c2ccncn2)cc1=O] | 2-Cyclohexyloxy-1-methyl-1H-[4,4']bipyrimidinyl-6-one |

TABLE 1-continued

| COMPOUND NO. | STRUCTURE | COMPOUND NAME |
| --- | --- | --- |
| 1.803 | 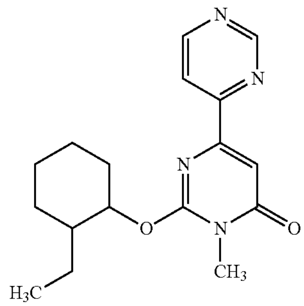 [SMILES: CCC1CCCCC1Oc1nc(-c2ccncn2)cc(=O)n1C] | 2-(2-Ethyl-cyclohexyloxy)-1-methyl-1H-[4,4']bipyrimidinyl-6-one |
| 1.804 | 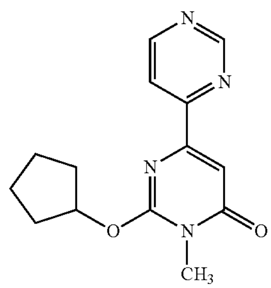 [SMILES: Cn1c(OC2CCCC2)nc(-c2ccncn2)cc1=O] | 2-Cyclopentyloxy-1-methyl-1H-[4,4']bipyrimidinyl-6-one |
| 1.805 | 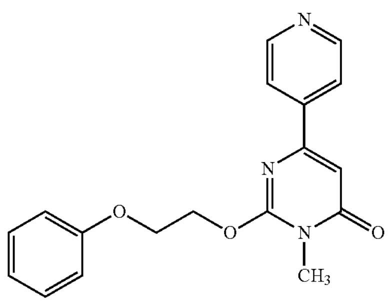 | 3-Methyl-2-(2-phenoxy-ethoxy)-6-pyridin-4-yl-3H-pyrimidin-4-one |
| 1.806 | 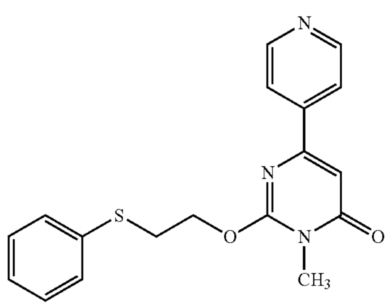 [SMILES: Cn1c(OCCSc2ccccc2)nc(-c2ccncc2)cc1=O] | 3-Methyl-2-(2-phenylsulfanyl-ethoxy)-6-pyridin-4-yl-3H-pyrimidin-4-one |
| 1.807 | 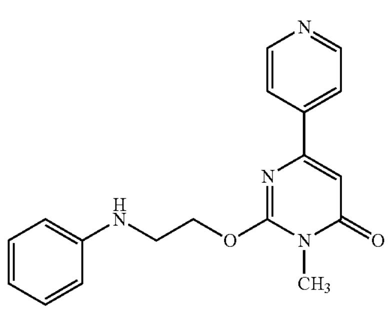 [SMILES: Cn1c(OCCNc2ccccc2)nc(-c2ccncc2)cc1=O] | 3-Methyl-2-(2-phenylamino-ethoxy)-6-pyridin-4-yl-3H-pyrimidin-4-one |

TABLE 1-continued

| COMPOUND NO. | STRUCTURE | COMPOUND NAME |
|---|---|---|
| 1.808 | 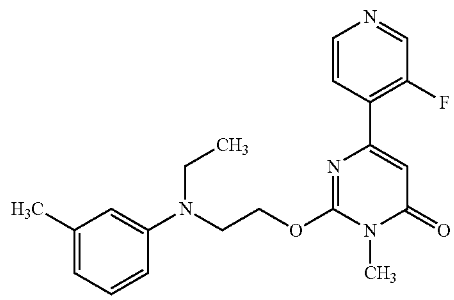 [SMILES: CCN(CCOc1nc(-c2ccncc2F)cc(=O)n1C)c1cccc(C)c1] | 2-[2-(Ethyl-m-tolyl-amino)-ethoxy]-6-(3-fluoro-pyridin-4-yl)-3-methyl-3H-pyrimidin-4-one |
| 1.809 | 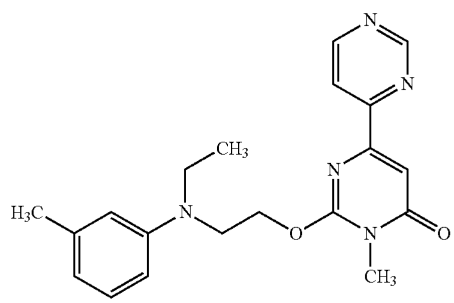 [SMILES: CCN(CCOc1nc(-c2ccncn2)cc(=O)n1C)c1cccc(C)c1] | 2-[2-(Ethyl-m-tolyl-amino)-ethoxy]-1-methyl-1H-[4,4']bipyrimidinyl-6-one |
| 1.810 | 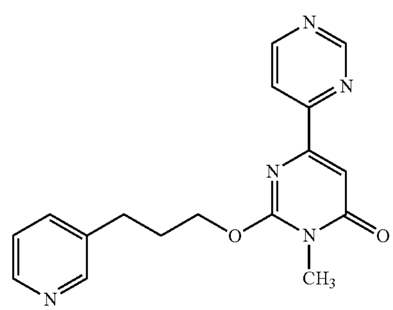 [SMILES: Cn1c(OCCCc2cccnc2)nc(-c2ccncn2)cc1=O] | 1-Methyl-2-(3-pyridin-3-yl-propoxy)-1H-[4,4']bipyrimidinyl-6-one |
| 1.901 | 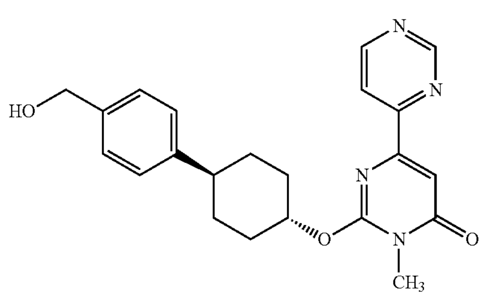 [SMILES: Cn1c(O[C@H]2CC[C@H](c3ccc(CO)cc3)CC2)nc(-c2ccncn2)cc1=O] | 2-[trans-4-(4-Hydroxymethyl-phenyl)cyclohexyloxy]-1-methyl-1H-[4,4']bipyrimidinyl-6-one |
| 1.902 | 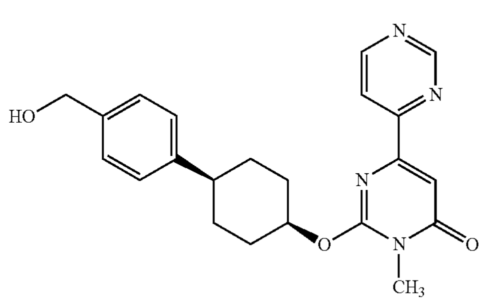 [SMILES: Cn1c(O[C@H]2CC[C@@H](c3ccc(CO)cc3)CC2)nc(-c2ccncn2)cc1=O] | 2-[cis-4-(4-Hydroxymethyl-phenyl)cyclohexyloxy]-1-methyl-1H-[4,4']bipyrimidinyl-6-one |

TABLE 1-continued

| COMPOUND NO. | STRUCTURE | COMPOUND NAME |
|---|---|---|
| 1.903 | 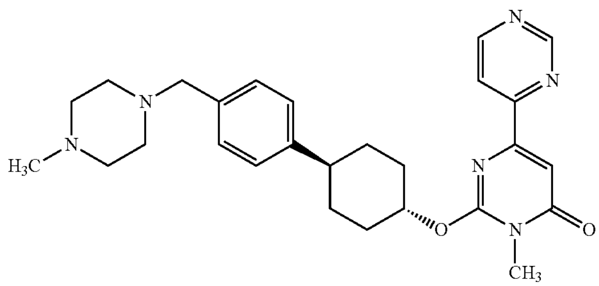 [SMILES: CN1CCN(Cc2ccc([C@H]3CC[C@H](Oc4nc(-c5ccncn5)cc(=O)n4C)CC3)cc2)CC1] | 1-Methyl-2-{trans-4-[4-(4-methyl-piperazin-1-ylmethyl)phenyl]cyclohexyloxy}-1H-[4,4']bipyrimidinyl-6-one |
| 1.904 | 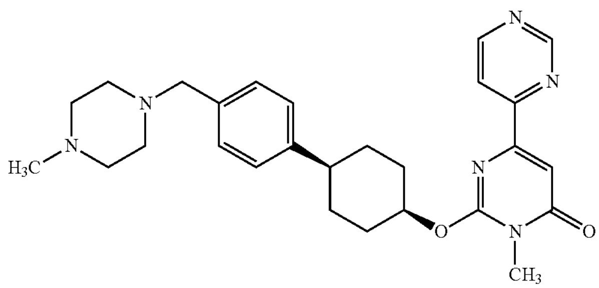 | 1-Methyl-2-{cis-4-[4-(4-methyl-piperazin-1-ylmethyl)phenyl]cyclohexyloxy}-1H-[4,4']bipyrimidinyl-6-one |
| 2.001 | 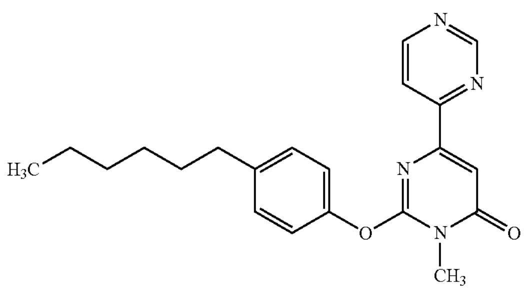 [SMILES: CCCCCCc1ccc(Oc2nc(-c3ccncn3)cc(=O)n2C)cc1] | 2-(4-Hexylphenoxy)-1-methyl-1H[4,4']bipyrimidinyl-6one |
| 2.002 | 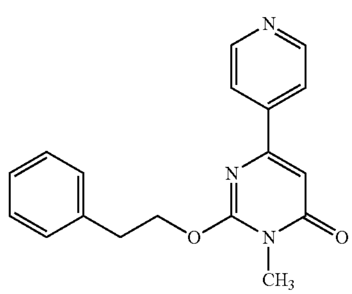 [SMILES: Cn1c(OCCc2ccccc2)nc(-c2ccncc2)cc1=O] | 3-Methyl-2-phenethyloxy-6-pyridin-4-yl-3H-pyrimidin-4-one |
| 2.003 | 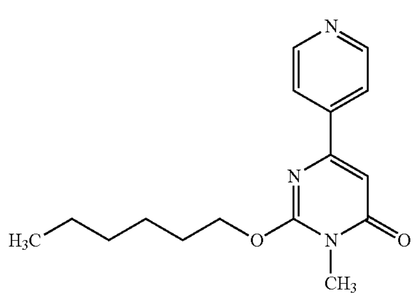 [SMILES: CCCCCCOc1nc(-c2ccncc2)cc(=O)n1C] | 2-Hexyloxy-3-methyl-6-pyridin-4-yl-3H-pyrimidin-4-one |

TABLE 1-continued

| COMPOUND NO. | STRUCTURE | COMPOUND NAME |
|---|---|---|
| 2.101 | 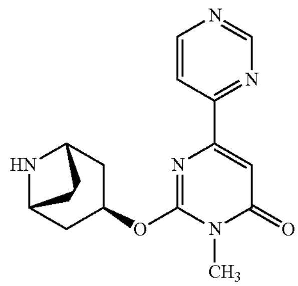 [SMILES: Cn1c(O[C@H]2C[C@H]3CC[C@@H](C2)N3)nc(-c2ccncn2)cc1=O] | endo-2-(8-Aza-bicyclo[3.2.1]oct-3-yloxy)-1-methyl-1H-[4,4']bipyrimidinyl-6-one |
| 2.102 | 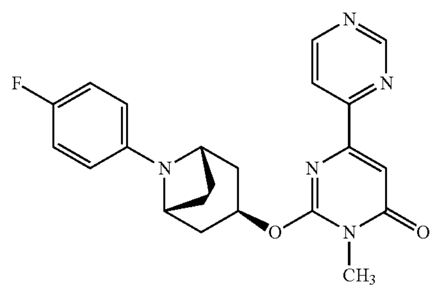 [SMILES: Cn1c(O[C@H]2C[C@H]3CC[C@@H](C2)N3c2ccc(F)cc2)nc(-c2ccncn2)cc1=O] | endo-2-[8-(4-Fluoro-phenyl)-8-aza-bicyclo[3.2.1]oct-3-yloxy]-1-methyl-1H-[4,4']bipyrimidinyl-6-one |
| 2.201 | 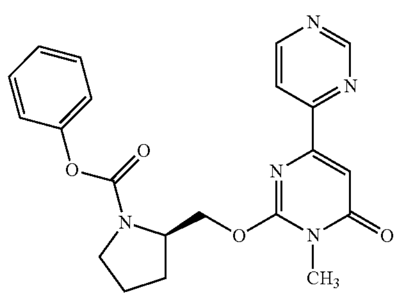 [SMILES: Cn1c(OC[C@H]2CCCN2C(=O)Oc2ccccc2)nc(-c2ccncn2)cc1=O] | Phenyl (2R)-2-(1-methyl-6-oxo-1,6-dihydro-[4,4']bipyrimidinyl-2-yloxy methyl)pyrrolidine-1-carboxylate |
| 2.202 | 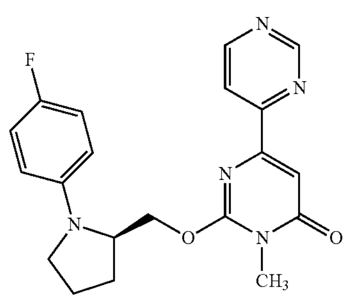 [SMILES: Cn1c(OC[C@H]2CCCN2c2ccc(F)cc2)nc(-c2ccncn2)cc1=O] | 2-[(2R)-1-(4-Fluoro-phenyl)pyrrolidin-2-ylmethoxy]-1-methyl-1H-[4,4']bipyrimidinyl-6-one |
| 2.203 | 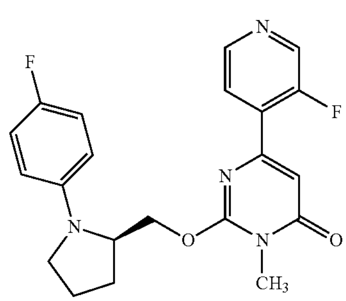 [SMILES: Cn1c(OC[C@H]2CCCN2c2ccc(F)cc2)nc(-c2ccncc2F)cc1=O] | 2-[(2R)-1-(4-Fluoro-phenyl)pyrrolidin-2-ylmethoxy]-6-(3-fluoro-pyridin-4-yl)-3-methyl-3H-pyrimidin-4-one |

TABLE 1-continued

| COMPOUND NO. | STRUCTURE | COMPOUND NAME |
|---|---|---|
| 2.204 | 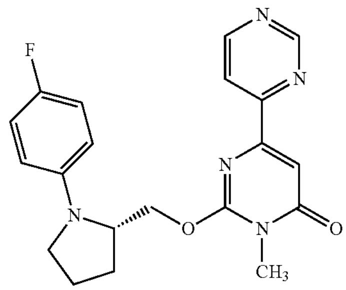 [SMILES: Cn1c(OC[C@@H]2CCCN2c2ccc(F)cc2)nc(-c2ccncn2)cc1=O] | 2-[(2S)-1-(4-Fluoro-phenyl)pyrrolidin-2-ylmethoxy]-1-methyl-1H-[4,4']bipyrimidinyl-6-one |
| 2.205 | 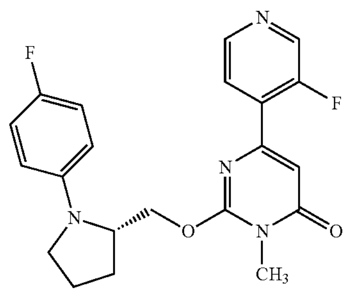 [SMILES: Cn1c(OC[C@@H]2CCCN2c2ccc(F)cc2)nc(-c2ccncc2F)cc1=O] | 2-[(2S)-1-(4-Fluoro-phenyl)pyrrolidin-2-ylmethoxy]-6-(3-fluoro-pyridin-4-yl)-3-methyl-3H-pyrimidin-4-one |
| 2.206 | 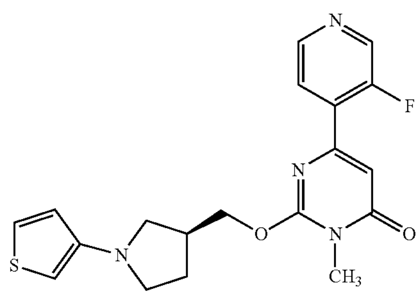 [SMILES: Cn1c(OC[C@H]2CCN(c3ccsc3)C2)nc(-c2ccncc2F)cc1=O] | 6-(3-Fluoro-pyridin-4-yl)-3-methyl-2-[(3S)-1-(thiophen-3-yl)pyrrolidin-3-ylmethoxy]-3H-pyrimidin-4-one |
| 2.207 | 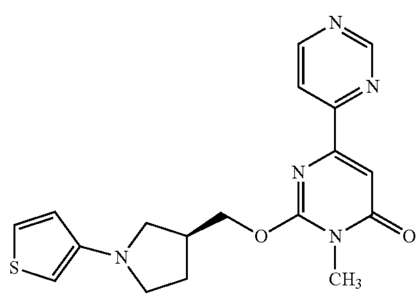 [SMILES: Cn1c(OC[C@H]2CCN(c3ccsc3)C2)nc(-c2ccncn2)cc1=O] | 1-Methyl-2-[(3S)-1-(thiophen-3-yl)pyrrolidin-3-ylmethoxy]-1H-[4,4']bipyrimidinyl-6-one |
| 2.208 | 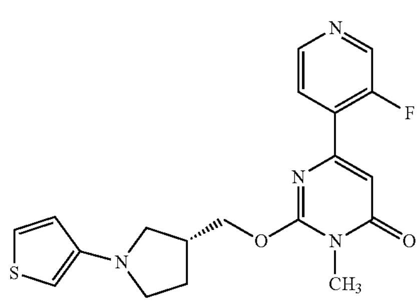 [SMILES: Cn1c(OC[C@@H]2CCN(c3ccsc3)C2)nc(-c2ccncc2F)cc1=O] | 6-(3-Fluoro-pyridin-4-yl)-3-methyl-2-[(3R)-1-(thiophen-3-yl)pyrrolidin-3-ylmethoxy]-3H-pyrimidin-4-one |

TABLE 1-continued

| COMPOUND NO. | STRUCTURE | COMPOUND NAME |
|---|---|---|
| 2.209 | 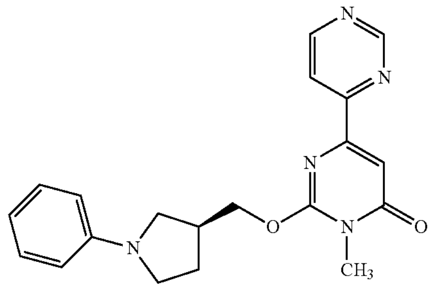 [SMILES: Cn1c(OC[C@H]2CCN(c3ccccc3)C2)nc(-c2ccncn2)cc1=O] | 1-Methyl-2-[(3S)-1-phenyl-pyrrolidin-3-ylmethoxy]-1H-[4,4']bipyrimidinyl-6-one |
| 2.210 | 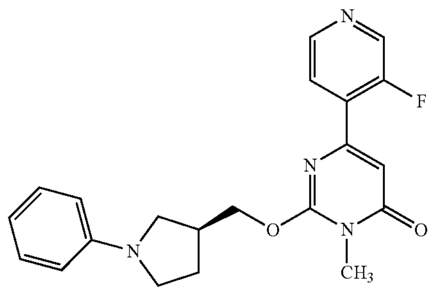 [SMILES: Cn1c(OC[C@H]2CCN(c3ccccc3)C2)nc(-c2ccncc2F)cc1=O] | 6-(3-Fluoro-pyridin-4-yl)-3-methyl-2-[(3S)-1-phenyl-pyrrolidin-3-ylmethoxy]-3H-pyrimidin-4-one |
| 2.211 | 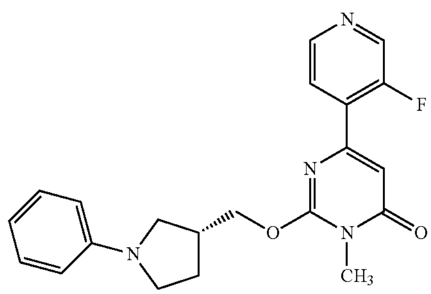 [SMILES: Cn1c(OC[C@@H]2CCN(c3ccccc3)C2)nc(-c2ccncc2F)cc1=O] | 6-(3-Fluoro-pyridin-4-yl)-3-methyl-2-[(3R)-1-phenyl-pyrrolidin-3-ylmethoxy]-3H-pyrimidin-4-one |
| 2.301 | 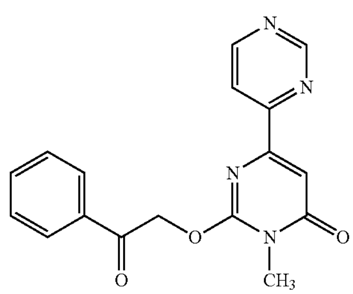 [SMILES: Cn1c(OCC(=O)c2ccccc2)nc(-c2ccncn2)cc1=O] | 1-Methyl-2-(2-oxo-2-phenyl-ethoxy)-1H-[4,4']bipyrimidinyl-6-one |
| 2.302 | 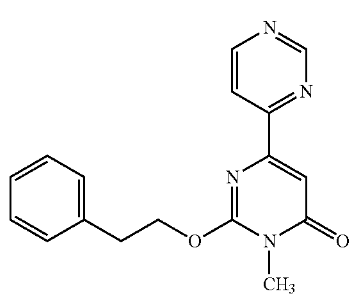 [SMILES: Cn1c(OCCc2ccccc2)nc(-c2ccncn2)cc1=O] | 1-Methyl-2-phenethyloxy-1H-[4,4']bipyrimidinyl-6-one |

TABLE 1-continued

| COMPOUND NO. | STRUCTURE | COMPOUND NAME |
|---|---|---|
| 2.303 | 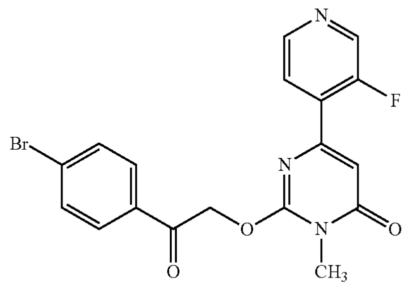 [SMILES: Cn1c(OCC(=O)c2ccc(Br)cc2)nc(-c2ccncc2F)cc1=O] | 2-[2-(4-Bromo-phenyl)-2-oxo-ethoxy]-6-(3-fluoro-pyridin-4-yl)-3-methyl-3H-pyrimidin-4-one |
| 2.304 | 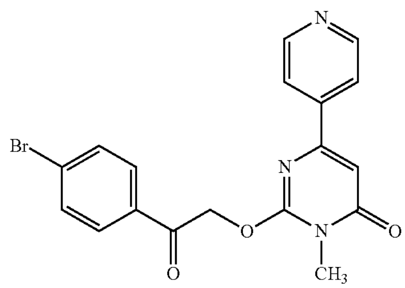 [SMILES: Cn1c(OCC(=O)c2ccc(Br)cc2)nc(-c2ccncc2)cc1=O] | 2-[2-(4-Bromo-phenyl)-2-oxo-ethoxy]-3-methyl-6-pyridin-4-yl-3H-pyrimidin-4-one |
| 2.305 | 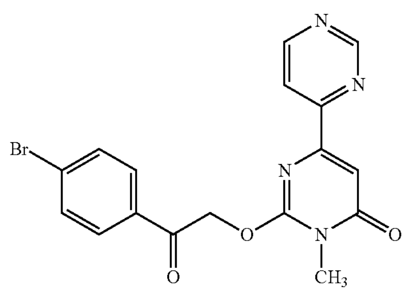 [SMILES: Cn1c(OCC(=O)c2ccc(Br)cc2)nc(-c2ccncn2)cc1=O] | 2-[2-(4-Bromo-phenyl)-2-oxo-ethoxy]-1-methyl-1H-[4,4'] bipyrimidinyl-6-one |
| 2.401 | 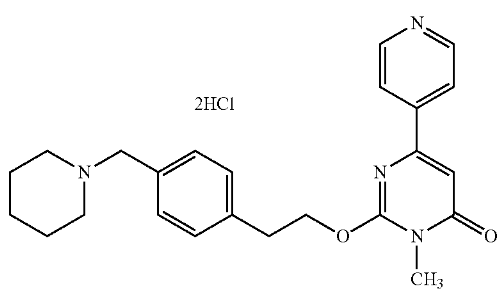 [SMILES: Cn1c(OCCc2ccc(CN3CCCCC3)cc2)nc(-c2ccncc2)cc1=O] | 3-Methyl-2-[2-(4-piperidin-1-ylmethyl-phenyl)ethoxy]-6-pyridin-4-yl-3H-pyrimidin-4-one dihydrochloride |
| 2.402 | 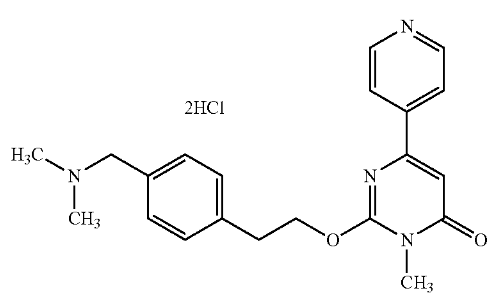 [SMILES: CN(C)Cc1ccc(CCOc2nc(-c3ccncc3)cc(=O)n2C)cc1] | 2-[2-(4-Dimethylaminomethyl-phenyl)ethoxy]-3-methyl-6-pyridin-4-yl-3H-pyrimidin-4-one dihydrochloride |

TABLE 1-continued

| COMPOUND NO. | STRUCTURE | COMPOUND NAME |
|---|---|---|
| 2.501 | 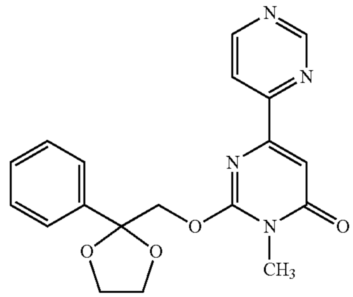 [SMILES: Cn1c(OCC2(c3ccccc3)OCCO2)nc(-c2ccncn2)cc1=O] | 1-Methyl-2-(2-phenyl-[1,3]dioxolan-2-ylmethoxy)-1H-[4,4']bipyrimidinyl-6-one |
| 2.502 | 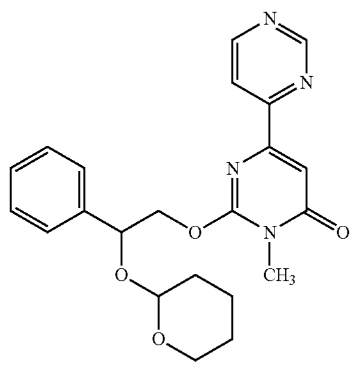 [SMILES: Cn1c(OCC(OC2CCCCO2)c2ccccc2)nc(-c2ccncn2)cc1=O] | 1-Methyl-2-[2-phenyl-2-(tetrahydro-pyran-2-yloxy)ethoxy]-1H-[4,4']bipyrimidinyl-6-one |

The compounds represented by the aforementioned formula (I) can be prepared, for example, by the method shown in Scheme 1.

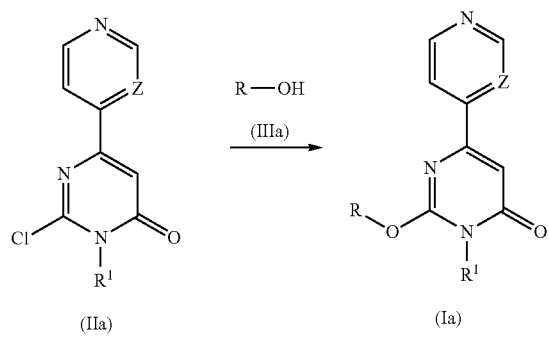

(Scheme 1)

(In the above scheme, definition of $R^1$ is the same as those already described. R is $R^2$—Y-L-, wherein definition of $R^2$, Y, and L are the same respectively as those already described.)

The 2-chloropyrimidone represented by the above formula (IIa) is prepared easily by the method described in the specification of WO2003/027080 and WO2003/037888.

Chloride derivative (IIa) is allowed to react with the compound (IIIa) or salts thereof in the presence of a base such as sodium hydroxide, potassium hydroxide, sodium methoxide, sodium ethoxide, sodium carbonate, sodium hydrogencarbonate, potassium carbonate, sodium hydride, potassium hydride, n-butyllithium, lithium diisopropylamide triethylamine, diisopropylethylamine, and 1,8-diazabicyclo[5,4,0]undec-7-en for 1 to 100 hours at a suitable temperature ranging from 0° C. to 200° C. under nitrogen or argon atmosphere or under ordinary air to afford the desired compound (Ia).

Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether cyclopentyl methyl ether, 1,2-dimethoxyethane; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

The compounds represented by the aforementioned formula (I) can also be prepared, by the method shown in Scheme 2 below.

(Scheme 2)

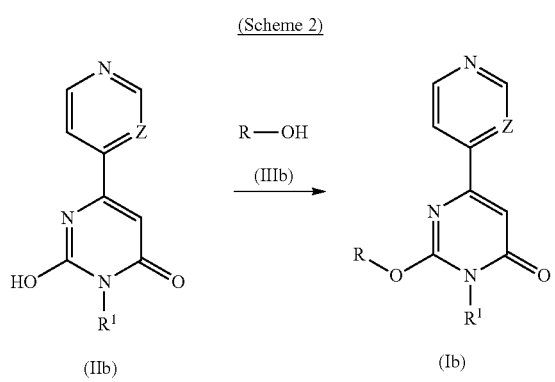

(In the above scheme, definition of $R^1$ is the same as those already described. R is $R^2$—Y-L-, wherein definition of $R^2$, Y, and L are the same respectively as those already described.)

The hydroxy-pyrimidone represented by the above formula (IIb) can be prepared via a reaction of 2-chloropyrimidone represented by the above formula (IIa) and an alkaline metal hydroxide such as sodium hydroxide as shown in Reference Example 1 shown below.

The compound represented by formula (Ib) can be prepared via Mitsunobu reaction of the hydroxy-pyrimidone represented by formula (IIb) and the compound represented by formula (IIIb) or salts thereof. Specifically, the hydroxy-pyrimidone represented by formula (IIb) and the compound represented by formula (IIIb) or salts thereof may be reacted in the presence of an azodicarboxylate or an azodicarboxamide such as diethylazodicarboxylate, diisopropylazodicarboxylate, di-tert-butylazodicarboxylate, 1,1'-(azodicarbonyl)dipyperidine, or N,N,N',N'-tetramethyl azodicarboxamide, and in the presence of triphenylphosphine, polymer-bound triphenylphosphine, diphenyl(2-pridyl)phosphine, or (4-dimethylaminophenyl)diphenylphosphine for 1 to 100 hours at a suitable temperature ranging from 0° C. to 100° C. under nitrogen or argon atmosphere or under ordinary air to afford the desired compound (Ib).

Examples of a solvent for the reactions include etheric solvents such as diethyl ether, tert-butyl methyl ether, tetrahydrofuran, isopropyl ether, cyclopentyl methyl ether, 1,2-dimethoxyethane; hydrocarbonic solvents such as benzene, toluene, xylene; halogenated hydrocarbonic solvents such as dichloromethane, chloroform, dichloroethane; and the like. Generally, a single solvent or a mixture of two or more solvents may be used.

TPK1 inhibitor may lead to the effective drug for the treatment of Alzheimer's disease and many structurally diverse classes of compounds with in vitro TPK1 inhibitory activity have been already disclosed. However, design of novel structures for the TPK1 inhibitor is expected to lead to clinically more efficient compounds through several improvements in in vitro and in vivo activities, kinase selectivity, ADME, PK/PD profiles and physical properties.

The compounds may also be possibly used as a medicament for therapeutic treatment of ischemic cerebrovascular accidents (Biochem J. 359, 1 (2001)), traumatic head injury (Trends in Molecular Medicine 8, 126 (2002)), Down syndrome, cerebral amyloid angiopathy, cerebral bleeding due to Lewy body disease and the like by suppressing the cytotoxicity of Aβ. Furthermore, the compounds may possibly be used as a medicament for therapeutic treatment of neurodegenerative diseases (Current Opinion in Neurobiology 12, 275 (2002)) such as progressive supranuclear palsy (Acta Neuropathol. 104, 583 (2002)), subacute sclerosing panencephalitic parkinsonism, postencephalitic parkinsonism, pugilistic encephalitis, Guam parkinsonism-dementia complex, Lewy body disease, Pick's disease (Acta Neuropathol. 104, 583 (2002)), corticobasal degeneration (Acta Neuropathol. 104, 583 (2002) frontotemporal dementia (Acta Neuropathol. 104, 583 (2002)), vascular dementia, traumatic injuries, brain and spinal cord trauma, peripheral neuropathies, retinopathies and glaucoma and amyotrophic lateral sclerosis (European Journal of Neuroscience, Vol. 22, pp. 301-309, 2005) as well as other diseases such as non-insulin dependent diabetes (Biochem J. 359, 1 (2001)), obesity, manic depressive illness and schizophrenia, alopecia.

In addition, inhibition of TPK1 could be useful in treating cancers, such as breast cancer, non-small lung carcinoma, thyroid cancer, T or B-cell leukaemia and several virus-induced tumors. For example, the active form of TPK1 has been shown to be elevated in the tumors of colorectral cancer patients and inhibition of TPK1 in colorectal cancer cells activates p53-dependent apoptosis and antagonises tumor growth.

Inhibitors of human TPK1 may also inhibit pfGSK3, an ortholog of this enzyme found in *Plasmodium falciparum*, as a consequence they could be used for the treatment of malaria (Biochimica et Biophysica Acta 1697, 181-196, 2004).

According to recent data, TPK1 inhibitors might be used in the treatment or prevention of *Pemphigus vulgaris*.

Accordingly, the compounds of the present invention are useful as an active ingredient of a medicament which radically enables preventive and/or therapeutic treatment of Alzheimer disease. In addition, the compounds of the present invention are also useful as an active ingredient of a medicament for preventive and/or therapeutic treatment of ischemic cerebrovascular accidents, Down syndrome, cerebral bleeding due to solitary cerebral amyloid angiopathy, progressive supranuclear palsy, subacute sclerosing panencephalitic parkinsonism, postencephalitic parkinsonism, pugilistic encephalosis, Guam parkinsonism-dementia complex, Lewy body disease, Pick's disease, corticobasal degeneration frontotemporal dementia, vascular dementia, traumatic injuries, brain and spinal cord trauma, peripheral neuropathies, retinopathies and glaucoma, non-insulin dependent diabetes, obesity, manic depressive illness, schizophrenia, alopecia, breast cancer, non-small cell lung carcinoma, thyroid cancer, T or B-cell leukemia, several virus-induced tumors, amyotrophic lateral sclerosis, malaria, pemphigus vulgaris and neutropenia induced by cancer chemotherapy.

Among the above exemplified diseases, the compounds of the present invention are particularly useful as an active ingredient of a medicament for preventive and/or therapeutic treatment of non-insulin dependent diabetes, Alzheimer's disease, ischemic cerebrovascular accidents, progressive supranuclear palsy, Pick's disease, corticobasal degeneration, frontotemporal dementia, traumatic injuries and brain and spinal cord trauma, amyotrophic lateral sclerosis and malaria. Among these diseases, Alzheimer's disease is more preferable.

As the compound of the present invention has good safety and good pharmacokinetics, the compound has preferable characteristics as a medicament.

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more of pharmaceutical additives. As the active ingredient of the medicament of the present invention, two or more of the aforementioned substance may be used in combination.

A type of the pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content rations of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administrations, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

Dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 3000 mg (the weight of an active ingredient) to an adult.

EXAMPLES

The present invention will be explained more specifically with reference to examples. However, the scope of the present invention is not limited to the following examples. The compound number in the examples corresponds to that in the table above.

Reference Example 1

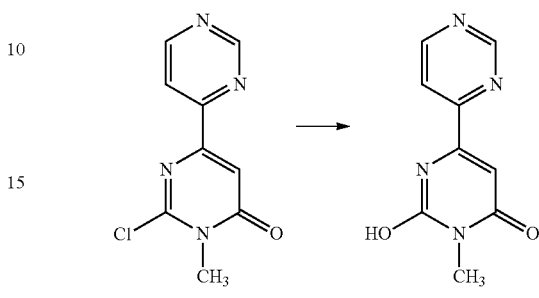

To a mixture of 2-chloro-1-methyl-1H-[4,4']bipyrimidinyl-6-one (20 g, 90 mmol) in 1,4-dioxane (200 ml) was added 5N aqueous solution of sodium hydroxide (100 ml) at room temperature. The resulting mixture was heated to 85° C. and stirred for 18 hours. After cooling to room temperature, the reaction mixture was neutralized by the addition of 1N aqueous hydrochloric acid. The resulting solid was collected by filtration and washed by ethyl acetate. 2-Hydroxy-1-methyl-1H-[4,4']bipyrimidinyl-6-one was then isolated as a white solid (14.5 g, 71 mmol, 79%).

Reference Example 2

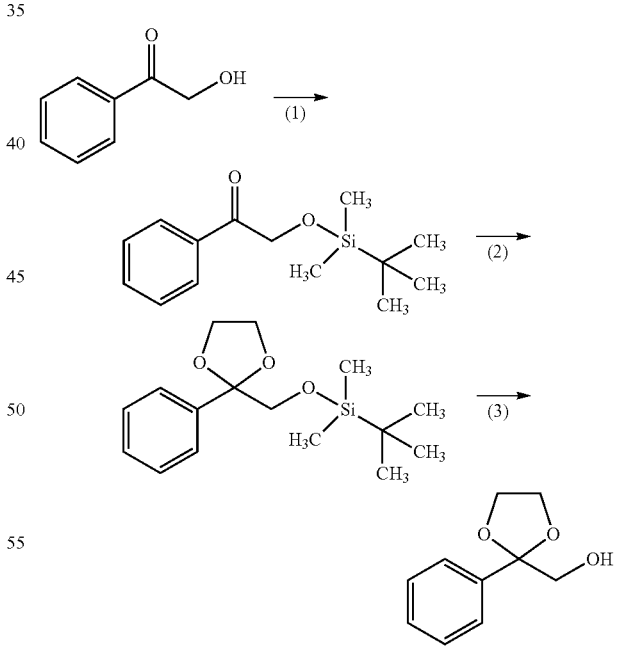

(1) To a solution of 2-hydroxyacetophenone (10 g, 74.5 mmol) and imidazole (15 g, 220 mmol) in N,N-dimethylformamide (50 ml) was added tert-butyldimethylchlorosilane (22 g, 146 mmol) at room temperature for 6 hours. The mixture was poured into water (200 ml) and extracted twice with 200 ml of ethyl acetate. The organic layer was washed with brine, dried over sodium sulfate, and the solvent was evaporated under reduced pressure. The crude product was purified by silica gel column chromatography (eluent; hexane/ethyl acetate=1/1) to give 2-(tert-butyldimethylsilanyloxy)-1-phenylethanone (8.0 g, 31.9 mmol, 43%) as a yellow oil.

(2) 2-(tert-Butyldimethylsilanyloxy)-1-phenylethanone (8.0 g, 32 mmol), ethylene glycol (1.99 g, 32 mmol), and p-toluenesulfonic acid (50 mg) was suspended in benzene (50 ml). The mixture was stirred under reflux for 5 hours. The solvent was evaporated under reduced pressure. The residue was treated with water and ethyl acetate. The organic layer was dried over sodium sulfate and the solvent was evaporated under reduced pressure. The crude was purified by silica gel column chromatography (eluent; hexane/ethyl acetate=1/1) to give tert-butyldimethyl-(2-phenyl-[1,3]dioxolan-2-yl-methoxy)silane (5.5 g, 18.7 mmol, 58%) as a yellow oil.

(3) To a solution of tert-butyldimethyl-(2-phenyl-[1,3]dioxolan-2-yl-methoxy)silane (5.5 g, 18.7 mmol) in tetrahydrofuran (50 ml) was added tetrabutylammonium fluoride (1M in tetrahydrofuran, 56 ml) at room temperature. The mixture was stirred at room temperature for 12 hours. The solvent was evaporated under reduced pressure. The residue was purified by silica gel column chromatography (eluent; hexane/ethyl acetate=3/1) to give (2-phenyl-[1,3]dioxolan-2-yl)methanol (1.54 g, 8.5 mmol, 45%) as a yellow oil.

Reference Example 3

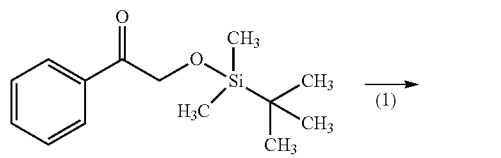

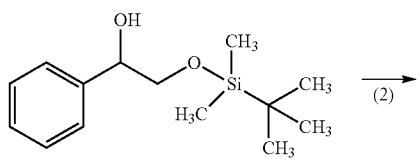

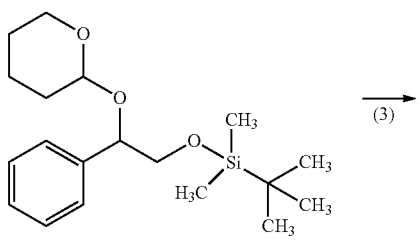

(1) To a solution of 2-(tert-butyldimethylsilanyloxy)-1-phenylethanone (2.5 g, 10 mmol, Example 4) in methanol (30 ml) added with sodium borohydride (378 mg, 10 mmol) at room temperature. The mixture was stirred at room temperature for 5.5 hours and the solvent was evaporated under reduced pressure. The residue was purified by silica gel column chromatography (eluent; hexane/ethyl acetate=3/1) to give 2-(tert-butyldimethylsilanyloxy)-1-phenylethanol (0.73 g, 2.9 mmol, 29%) as a colorless oil.

(2) To a solution of 2-(tert-butyldimethylsilanyloxy)-1-phenylethanol (0.73 g, 2.9 mmol) and 3,4-dihydro-2H pyran (486 mg, 5.78 mmol) in dichloromethane (30 ml) was added p-toluenesulfonic acid monohydrate (50 mg). The mixture was stirred at room temperature for 12 hours and the solvent was evaporated under reduced pressure. The residue was purified by silica gel column chromatography (eluent; hexane/ethyl acetate=3/1) to give tert-butyldimethyl[2-phenyl-2-(tetrahydropyran-2-yl-oxy)ethoxy]silane (0.86 g, 2.9 mmol, >99%) as a colorless oil.

(3) 2-Phenyl-2-(tetrahydropyran-2-yl-oxy)ethanol was obtained as a colorless oil from tert-butyldimethyl[2-phenyl-2-(tetrahydropyran-2-yl-oxy)ethoxy]silane and tetrabutylammonium fluoride in the same manner as that of step (3) of Reference Example 2.

Reference Example 4

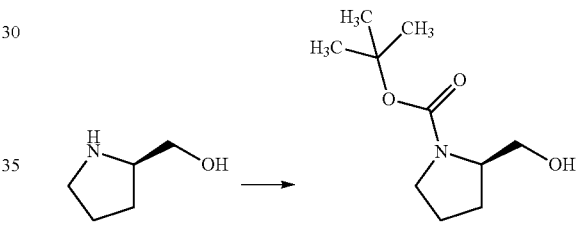

To a solution of (R)-pyrrolidine-2-yl-methanol (purchased from Sigma-Aldrich Corporation, 5 g, 49 mmol) and 1N aqueous solution of sodium hydroxide (100 ml) in tetrahydrofuran (100 ml) at 0° C. was added di-tert-butyl dicarbonate (10.9 g, 50 mmol). The resulting mixture was warmed to room temperature and stirred for 3 hours. The reaction mixture was diluted with water and extracted with ethyl acetate. The organic layer was washed with brine and dried over anhydrous sodium sulfate. After evaporation of the solvent, the residue was purified by silica gel column chromatography (eluent; hexane/ethyl acetate=1/1 to 1/2) to afford (R)-tert-butyl 2-(hydroxymethyl)pyrrolidine-1-carboxylate as a white solid (5.7 g, 28 mmol, 57%).

Reference Example 5

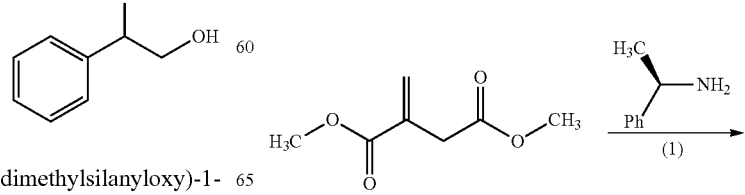

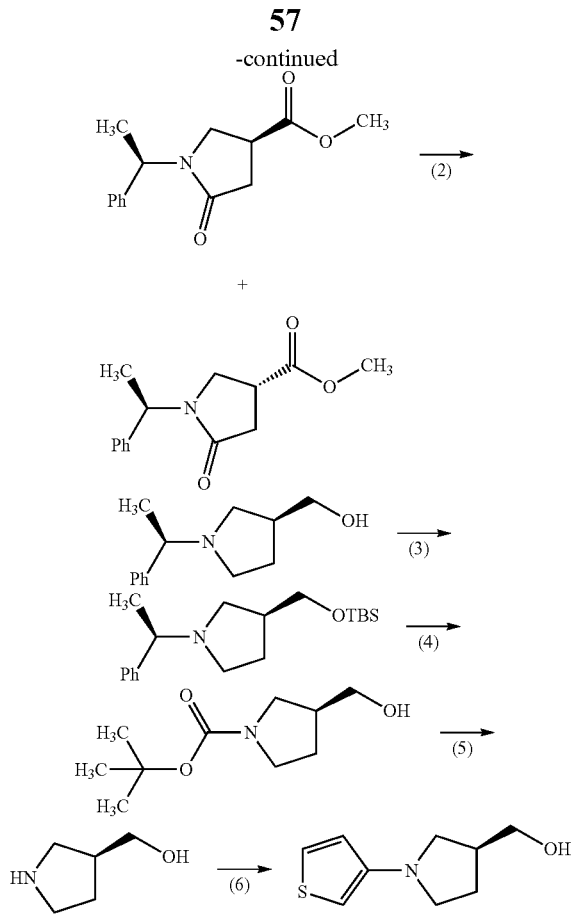

(1) To a solution of dimethyl itaconate (25 g, 158 mmol) in methanol (150 ml) was added (R)-1-phenylethylamine (20 ml, 158 mmol) at room temperature. The resulting mixture was stirred for 18 hours and concentrated. The residue was dissolved in toluene (100 ml) and p-toluenesulfonic acid (3.0 g, 16 mmol) was added at room temperature. The mixture was refluxed for 16 hours and concentrated. The residue was purified by silica gel column chromatography (eluent; hexane/ethyl acetate=1/1 to 1/3) to afford methyl (3S)-5-oxo-1-[(1R)-1-phenylethyl]pyrrolidine-3-carboxylate as a white solid (14.0 g, 56.5 mmol, 36%) and methyl (3R)-5-oxo-1-[(1R)-1-phenylethyl]pyrrolidine-3-carboxylate as a yellow oil (18.7 g, 75.5 mmol, 48%). Each stereochemistry was determined by the data based on the literature (J. Med. Chem. 1990, 33, 71-77).

Methyl (3S)-5-oxo-1-[(1R)-1-phenylethyl]pyrrolidine-3-carboxylate $^1$H-NMR (400 MHz, CDCl$_3$) δ: 1.54 (3H, d, J=7.2 Hz), 2.65-2.77 (2H, m), 3.14-3.23 (2H, m), 3.50-3.57 (1H, m), 3.65 (3H, s), 5.50 (1H, q, J=7.2 Hz), 7.26-7.36 (5H, m)

Methyl (3R)-5-oxo-1-[(1R)-1-phenylethyl]pyrrolidine-3-carboxylate $^1$H-NMR (400 MHz, CDCl$_3$) δ: 1.54 (3H, d, J=7.1 Hz), 2.65-2.79 (2H, m), 3.06-3.14 (1H, m), 3.19 (1H, dd, J=8.6, 9.8 Hz), 3.54 (1H, dd, J=6.4, 9.7 Hz), 3.72 (3H, s), 5.50 (1H, q, J=7.1 Hz), 7.27-7.37 (5H, m)

(2) To a slurry of lithium aluminum hydride (4.55 g, 120 mmol) in cyclopentyl methyl ether (100 ml) at 0° C. under nitrogen atmosphere was added methyl (3S)-5-oxo-1-[(1R)-1-phenylethyl]pyrrolidine-3-carboxylate (14.0 g, 56.5 mmol) dropwise. The resulting mixture was stirred for 15 minutes and gradually warmed to room temperature. After one hour, the reaction was quenched by the addition saturated sodium sulfate aqueous solution at 0° C. and the resulting solid materials were removed by filtration. Concentration of the filtrate afforded {(3S)-1-[(1R)-1-phenylethyl]pyrrolidin-3-yl}methanol (6.62 g, 32 mmol, 57%). This compound was used for the next reaction without further purification.

(3) To a solution of {(3S)-1-[(1R)-1-phenylethyl]pyrrolidin-3-yl}methanol (6.62 g, 32 mmol) and imidazole (4.77 g, 70 mmol) in N,N-dimethylformamide (90 ml) was added tert-butyldimethylchlorosilane (5.28 g, 35 mmol) at 0° C. and the resulting mixture was warmed to room temperature. The reaction mixture was stirred overnight and poured into water. Extraction with ethyl acetate was performed. The organic layer was washed with brine and dried over anhydrous sodium sulfate. The solution was concentrated and the residue was purified by silica gel column chromatography (eluent; hexane/ethyl acetate=90/10 to 75/25) to afford (3S)-3-({[tert-butyl(dimethyl)silyl]oxy}methyl)-1-[(1R)-1-phenylethyl]pyrrolidine (8.81 g, 27.6 mmol, 86%) as a colorless oil.

(4) To a solution of (3S)-3-({[tert-butyl(dimethyl)silyl]oxy}methyl)-1-[(1R)-1-phenylethyl]pyrrolidine (8.81 g, 27.6 mmol) in 1,2-dichloroethane (75 ml) was added 1-chloroethyl chloroformate (8.1 ml, 75 mmol) at room temperature. The resulting mixture was refluxed for 5 hours and cooled to room temperature. To the brown solution was added diisopropylethylamine (2.3 ml, 13 mmol). The mixture was refluxed for additional 3 hours and concentrated. The residue was diluted with ethyl acetate and washed with 1N aqueous hydrochloric acid. The organic layer was dried over anhydrous sodium sulfate and concentrated in vacuo. The residue was dissolved in methanol (75 ml) and refluxed for one hour. After concentration under reduced pressure, 1N aqueous hydrochloric acid was added. The aqueous solution was washed with ethyl acetate and basified by solid potassium carbonate. The basic solution was cooled to 0° C. and a solution of di-tert-butyl dicarbonate (6.3 g, 29 mmol) in tetrahydrofuran (75 ml) was added. The resulting mixture was stirred for 3 hours. The organic materials were extracted with ethyl acetate and dried over anhydrous sodium sulfate. The solvent was removed under reduced pressure and the residue was purified by silica gel column chromatography (eluent; hexane/ethyl acetate=3/1 to 1/2) to afford (S)-tert-butyl 3-(hydroxymethyl)pyrrolidine-1-carboxylate (2.96 g, 14.7 mmol, 53%) as a colorless oil.

(5) (S)-tert-Butyl 3-(hydroxymethyl)pyrrolidine-1-carboxylate (2.96 g, 14.7 mmol) in a round bottom flask was mixed with 4N hydrogen chloride in ethyl acetate (30 ml) at room temperature. The mixture was stirred for 2 hours and concentrated in vacuo. The residue was diluted with ethanol (10 ml) and solid potassium carbonate was added. To the resulting slurry was added small amount of water until bubbles were generated. After 2 hours, filtration was performed to remove solid materials and the filtrate was concentrated to yield (S)-pyrrolidin-3-yl-methanol (1.49 g, 14.7 mmol, >99%) as an orange oil.

(6) A dried round bottom flask was charged with copper(I) iodide (0.10 g, 0.53 mmol), cesium carbonate (3.58 g, 11 mmol). The flask was evacuated and backfilled with nitrogen. Under the flow of nitrogen, (S)-pyrrolidin-3-yl-methanol (0.80 g, 7.9 mmol), 3-iodothiophene (0.54 ml, 5.3 mmol), 2-(2-methyl-1-oxopropyl)cyclohexanone (0.35 ml, 2.1 mmol), and N,N-dimethylformamide (5 ml) were added. The mixture was allowed to stir under nitrogen at ambient temperature for 12 hours. The mixture was diluted with ethyl acetate, passed through a glass filter to remove the inorganic salts and the solvent was removed under reduced pressure. The residue was purified by silica gel column chromatography (eluent; hexane/ethyl acetate=9/1 to 1/1) to afford (S)-[1-(thiophen-3-yl)pyrrolidin-3-yl]methanol (0.41 g, 2.2 mmol, 42%) as a brown oil. In the manner as above (2)-(6), with the use of methyl (3R)-5-oxo-1-[(1R)-1-phenylethyl]pyrrolidine-3-carboxylate instead of methyl (3S)-5-oxo-1-[(1R)-1-phenylethyl]pyrrolidine-3-carboxylate, (R)-[1-(thiophen-3-yl)pyrrolidin-3-yl]methanol was obtained (0.19 g, 1.0 mmol).

Reference Example 6

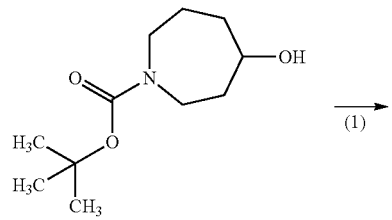

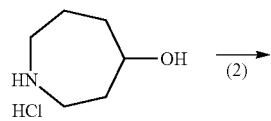

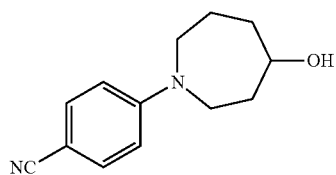

(1) To a solution of tert-butyl 4-hydroxyazepane-1-carboxylate (1.00 g, 4.65 mmol) in ethyl acetate (23 ml) was added 4N hydrogen chloride in ethyl acetate (23 ml, 92.0 mmol). The mixture was stirred at room temperature for 5 hours. The mixture was concentrated in vacuo to afford azepan-4-ol hydrochloride as a pale yellow oil (710 mg, 4.65 mmol, >99%). This compound was used for the next reaction without further purification.

(2) To a mixture of azepan-4-ol hydrochloride (300 mg, 1.98 mmol) and 4-fluorobenzonitrile (311 mg, 2.57 mmol) in dimethyl sulfoxide (3.00 ml) was added potassium carbonate (821 mg, 5.94 mmol). The mixture was stirred at 120° C. for 6 hours. The mixture was partitioned between water and ethyl acetate. The organic layer was washed with water (three times), dried over sodium sulfate, and concentrated in vacuo. The residue was purified by silica gel column chromatography (eluent; hexane/ethyl acetate=1/4) to afford 4-(4-hydroxyazepan-1-yl)benzonitrile as a yellow solid (306 mg, 1.41 mmol, 71%).

Reference Example 7

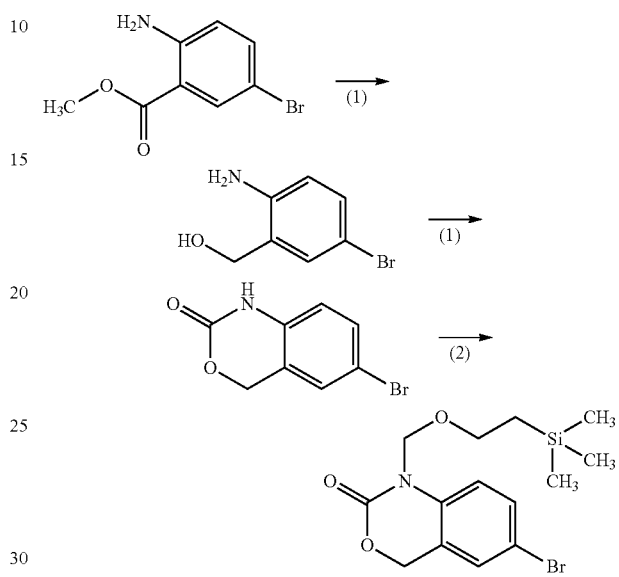

(1) To a mixture of lithium aluminum hydride (2.6 g, 69 mmol) in diethyl ether (54 ml) was added dropwise 5-bromoanthranillic acid methyl ester (6.3 g, 27 mmol) in diethyl ether (54 ml) at 0° C. The mixture was stirred at 0° C. for 3 hours. Then water (2.6 ml), 15 wt % aqueous solution of sodium hydroxide (2.6 ml) and water (7.8 ml) was added sequentially at 0° C. The mixture was filtrated through a pad of Celite, and concentrated in vacuo. The residue was dissolved into tetrahydrofuran (160 ml), and triethylamine (15 g, 150 mmol) was added. The mixture was cooled to 0° C., and trichloromethyl chloroformate (2.9 g, 15 mmol) was added. The mixture was stirred at room temperature for 4 hours. The mixture was partitioned between water and ethyl acetate. The organic layer was washed with brine, dried over sodium sulfate, and concentrated in vacuo to afford crude product. This crude product was washed with diethyl ether to afford 6-bromo-1,4-dihydro-2H-3,1-benzoxazin-2-one as a colorless solid (4.7 g, 21 mmol, 77%).

(2) To a solution of sodium hydride (55 wt % in mineral oil, 1.36 g, 31.2 mmol) in N,N-dimethylformamide (37 ml) was added 6-bromo-1,4-dihydro-2H-3,1-benzoxazin-2-one (5.93 g, 26.0 mmol) in N,N-dimethylformamide (37 ml) at 0° C. The mixture was stirred at room temperature for one hour, then 2-(chloromethoxy)ethyltrimethylsilane (4.77 g, 28.6 mmol) was added at 0° C. The mixture was stirred at room temperature overnight. The mixture was partitioned between water and ethyl acetate. The organic layer was washed with water (four times), dried over sodium sulfate, and concentrated in vacuo. The residue was purified by silica gel column chromatography (eluent; hexane/ethyl acetate=90/10 to 60/40) to afford 6-bromo-1-{[2-(trimethylsilyl)ethoxy]methyl}-1,4-dihydro-2H-3,1-benzoxazin-2-one as a pale yellow solid (7.96 g, 22.2 mmol, 85%).

Reference Example 8

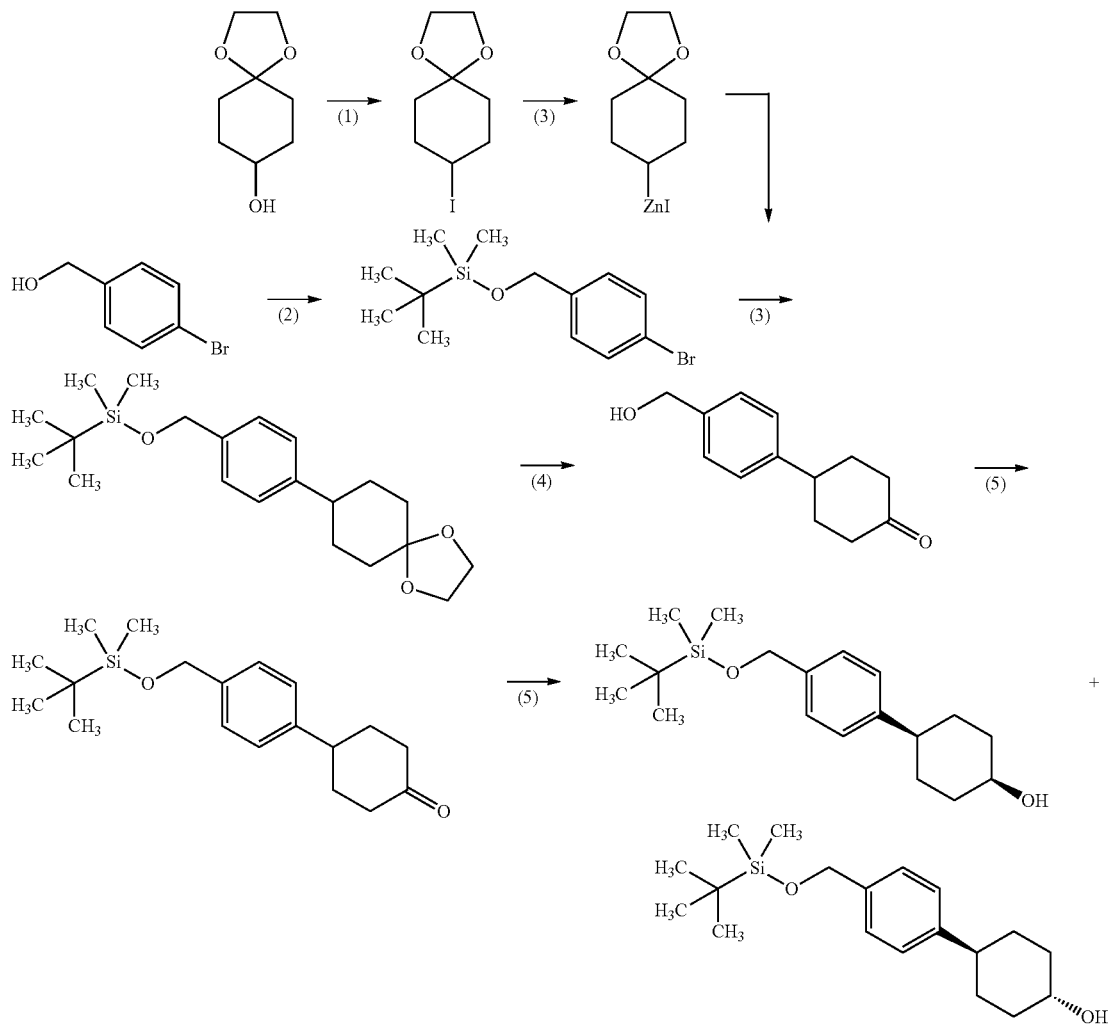

(1) To a mixture of 1,4-dioxa-spiro[4.5]decan-8-ol (18.0 g, 114 mmol), imidazole (10.1 g, 148 mmol) and triphenylphosphine (34.3 g, 131 mmol) in tetrahydrofuran (57 ml) was added iodine (33.2 g, 131 mmol) in tetrahydrofuran (57 ml) at 0° C. The mixture was warmed to room temperature, and stirred for 6 hours. The mixture was poured into 10 wt % aqueous sodium hydrogen sulfite, and the organic compound was extracted with hexane (three times). The organic layer was washed with water, dried over sodium sulfate, and concentrated in vacuo. The residue was dissolved into hexane again, and filtrated to remove triphenylphosphine oxide. The filtrate was concentrated in vacuo to afford 8-iodo-1,4-dioxa-spiro[4.5]decane as a colorless oil (18.1 g, 67.6 mmol, 59%).

(2) To a mixture of 4-bromobenzyl alcohol (18.0 g, 96.2 mmol) and imidazole (7.86 g, 115 mmol) in N,N-dimethylformamide (200 ml) was added tert-butyl dimethylchlorosilane (17.4 g, 115 mmol) at room temperature. The mixture was stirred for 5 hours. The mixture was poured into water, and extracted with ethyl acetate. The organic layer was washed with water (three times), dried over sodium sulfate, and concentrated in vacuo. The residue was purified by silica gel column chromatography (eluent; hexane/ethyl acetate=95/5) to afford (4-bromobenzyloxy)(tert-butyl)dimethylsilane as a colorless oil (27.7 g, 91.8 mmol, 92%).

(3) To a mixture of zinc powder (5.52 g, 84.5 mmol) and Celite (1.1 g) in N,N-dimethylacetamide (14 ml) was added dropwise chlorotrimethylsilane (0.930 ml, 7.33 mmol) in 1,2-dibromoethane (0.665 ml, 7.54 mmol) at 0° C. under nitrogen atmosphere. The mixture was warmed to room temperature, and stirred for 20 minutes. 8-Iodo-1,4-dioxa-spiro[4.5]decane (18.1 g, 67.6 mmol) in N,N-dimethylacetamide (34 ml) was then added dropwise at 0° C. The mixture was stirred for 30 minutes at room temperature, and the supernatant solution was added dropwise to the mixture of (4-bromobenzyloxy)(tert-butyl)dimethylsilane (15.7 g, 52.0 mmol), copper iodide (I) (792 mg, 4.16 mmol) and [1,1'-bis(diphenylphosphino)ferrocene]dichloropalladium(II)dichloromethane complex (1.70 g, 2.08 mmol) in N,N-dimethylacetamide (74 ml) at room temperature under nitrogen atmosphere. The mixture was stirred at 80° C. for 5 hours. The mixture was poured into the cold water, and extracted with ethyl acetate. The organic layer was washed with water (three times), dried over sodium sulfate, and concentrated in vacuo. The residue was purified by silica gel column chromatography (eluent; hexane/ethyl acetate=92/8) to afford tert-butyl-[4-(1,4-dioxa-spiro[4.5]dec-8-yl)benzyloxy]dimethylsilane as a pale yellow oil (14.0 g, 38.6 mmol, 74%).

(4) To a solution of tert-butyl-[4-(1,4-dioxa-spiro[4.5]dec-8-yl)benzyloxy]dimethylsilane (12.1 g, 33.3 mmol) in acetone (12 ml) and water (1.2 ml) was added pyridinium p-toluenesulfonate (2.51 g, 9.99 mmol) at room temperature. The mixture was refluxed for 3 hours. The mixture was partitioned between water and ethyl acetate. The organic layer was washed with saturated aqueous sodium hydrogen carbonate, dried over sodium sulfate, and concentrated in vacuo. The residue was purified by silica gel column chromatography (eluent; hexane/ethyl acetate=60/40) to afford 4-(4-hydroxymethylphenyl)cyclohexanone as a colorless solid (4.21 g, 20.6 mmol, 62%).

(5) To a mixture of 4-(4-hydroxymethylphenyl)cyclohexanone (4.55 g, 22.3 mmol) and imidazole (3.04 g, 44.6 mmol) in N,N-dimethylformamide (74 ml) was added tert-butyl dimethylchlorosilane (3.70 g, 24.5 mmol) at room temperature. The mixture was stirred overnight. The mixture was poured into water, and extracted with ethyl acetate. The organic layer was washed with water (three times), dried over sodium sulfate, and concentrated in vacuo. The residue was dissolved into methanol (111 ml) and cooled to 0° C., then sodium borohydride (2.53 g, 66.9 mmol) was added. The mixture was stirred at 0° C. for one hour. The mixture was partitioned between water and ethyl acetate. The organic layer was washed with brine, dried over sodium sulfate, and concentrated in vacuo. The residue was purified by silica gel column chromatography (eluent; hexane/ethyl acetate=80/20) to afford cis-4-[4-(tert-butyl-dimethyl-silanyloxymethyl)phenyl]cyclohexanol as a colorless solid (1.23 g, 3.84 mmol, 17%); Rf value=0.50 (eluent; hexane/ethyl acetate=75/25) and trans-4-[4-(tert-butyl-dimethyl-silanyloxymethyl)phenyl]cyclohexanol as a colorless solid (5.33 g, 16.6 mmol, 75%); Rf value=0.32 (eluent; hexane/ethyl acetate=75/25). 4-[4-(tert-Butyl-dimethyl-silanyloxymethyl)-phenyl]-cyclohexanol. The configuration of each stereoisomer was determined by $^1$H-NMR spectra and NOE experiments.

cis-4-[4-(tert-Butyl-dimethyl-silanyloxymethyl)phenyl]cyclohexanol $^1$H-NMR (400 MHz, CDCl$_3$) δ: 0.10 (6H, s), 0.94 (9H, s), 1.35-1.40 (1H, brs), 1.65-1.72 (4H, m), 1.84-1.93 (4H, m), 2.49-2.57 (1H, m), 4.11-4.14 (1H, m), 4.71 (2H, s), 7.20 (2H, d, J=8.2 Hz), 7.24-7.27 (2H, m)

trans-4-[4-(tert-Butyl-dimethyl-silanyloxymethyl)phenyl]cyclohexanol $^1$H-NMR (400 MHz, CDCl$_3$) δ: 0.09 (6H, s), 0.94 (9H, s), 1.37-1.58 (5H, m), 1.89-1.93 (2H, m), 2.07-2.10 (2H, m), 2.49 (1H, tt, J=3.9, 11.8 Hz), 3.65-3.72 (1H, m), 4.71 (2H, s), 7.16 (2H, d, J=7.8 Hz), 7.23-7.26 (2H, m)

Reference Example 9

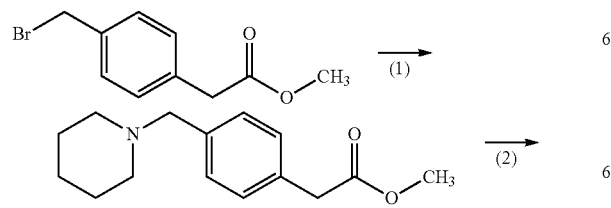

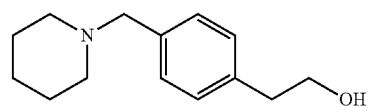

(1) To a solution of methyl (4-bromomethyl-phenyl)acetate (6.00 g, 24.7 mmol) in methanol (60 ml) was added piperidine (6.30 g, 74.0 mmol) at 0° C. The mixture was stirred at room temperature for 3 hours. The solvent was then evaporated under reduced pressure. The residue was poured into water, and extracted with ethyl acetate. The organic layer was washed with water, dried over sodium sulfate, and concentrated in vacuo to afford methyl (4-piperidin-1-yl-methyl-phenyl)acetate as a pale red oil (5.98 g, 24.2 mmol, 98%).

(2) To a mixture of lithium aluminum hydride (2.53 g, 66.7 mmol) in tetrahydrofuran (100 ml) was added dropwise methyl (4-piperidin-1-yl-methyl-phenyl)acetate (5.50 g, 22.2 mmol) at 0° C. under nitrogen atmosphere. The mixture was stirred at 0° C. for 2 hours. Water (2.5 ml), 15 wt % aqueous solution of sodium hydroxide (2.5 ml) and water (7.5 ml) was added to the mixture sequentially at 0° C. The mixture was filtrated through a pad of Celite, and concentrated in vacuo. The residue was purified by silica gel column chromatography (eluent; ethyl acetate/methanol=90/10 to 80/20) to afford 2-(4-piperidin-1-yl-methyl-phenyl)ethanol as a colorless oil (4.27 g, 19.5 mmol, 88%).

Example 1

Preparation of Compound No. 1.101

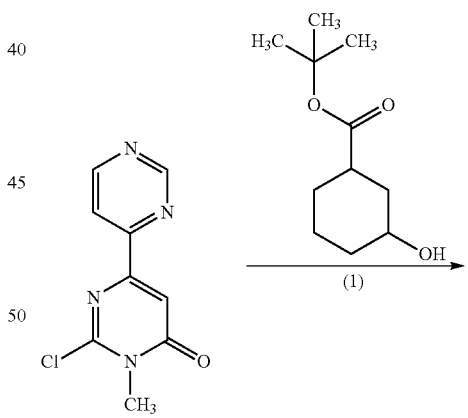

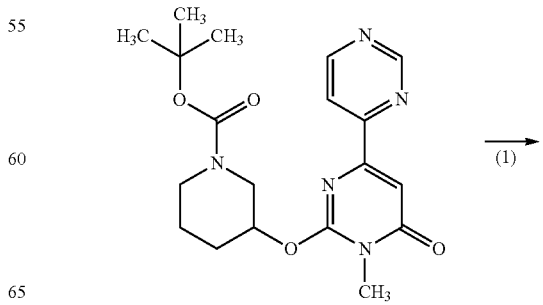

-continued

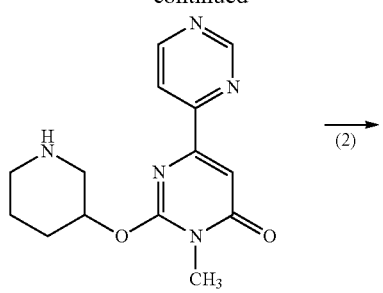

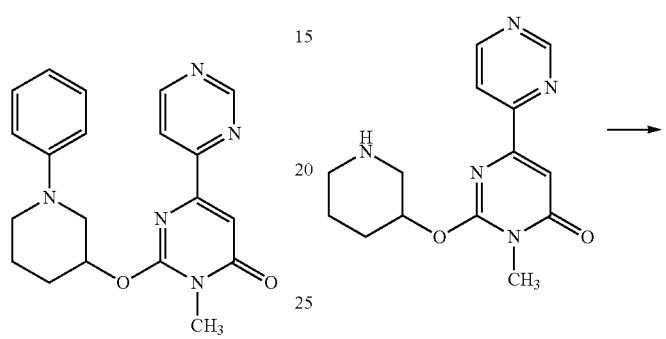

(1) To a mixture of sodium hydride (60 wt % in mineral oil, 0.24 g, 6.0 mmol) in N,N-dimethylformamide (15 ml) at room temperature under nitrogen atmosphere was added a solution of tert-butyl 3-hydroxypiperidine-1-carboxylate (1.0 g, 5.0 mmol) in N,N-dimethylformamide (5 ml) dropwise. After the mixture was stirred for one hour, 2-chloro-1-methyl-1H-[4,4']bipyrimidinyl-6-one (1.1 g, 5.0 mmol) was added to the mixture. The resulting mixture was stirred overnight and poured into water. Extractive workup was performed with ethyl acetate. The organic layer was dried over anhydrous sodium sulfate and concentrated in vacuo. To the residue was added 4N hydrogen chloride in ethyl acetate (10 ml) and the resulting slurry was stirred at room temperature for 2 hours. After concentration under reduced pressure, the residue was dissolved in water. The aqueous solution was washed with ethyl acetate and basified with potassium carbonate. Extraction with chloroform was performed three times and the organic layer was dried over anhydrous sodium sulfate. After concentration, analytically pure 1-methyl-2-(piperidine-3-yloxy)-1H-[4,4']bipyrimidinyl-6-one was isolated as a white solid (0.66 g, 2.3 mmol, 46%). This compound was used for the next reaction without further purification.

(2) To a round bottom flask, a mixture of 1-methyl-2-(piperidine-3-yloxy)-1H-[4,4']bipyrimidinyl-6-one (0.2 g, 0.70 mmol), bromobenzene (105 μl, 1.0 mmol), tris(dibenzylideneacetone)dipalladium(0) (46 mg, 0.05 mmol), 2-dicyclohexylphosphino-2',6'-dimethoxybiphenyl (82 mg, 0.2 mmol) and potassium phosphate tribasic (0.43 g, 2.0 mmol) in dimethoxyethane (3 ml) was added at room temperature under nitrogen atmosphere and heated to 100° C. After stirring for 5 hours, the resulting mixture was cooled to room temperature. The resulting mixture was poured into water and extracted with chloroform. The organic layer was dried over anhydrous sodium sulfate and concentrated in vacuo. The residue was purified by silica gel column chromatography (eluent; hexane/ethyl acetate=50/50) to afford 1-methyl-2-(1-phenyl-piperidin-3-yloxy)-1H-[4,4']bipyrimidinyl-6-one as a yellow solid (67 mg, 0.18 mmol, 26%).

Example 2

Preparation of Compound No. 1.102

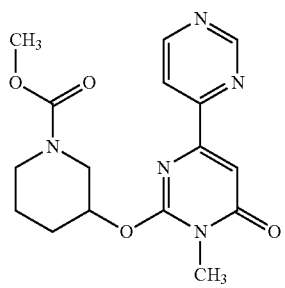

To a solution of 1-methyl-2-(piperidine-3-yloxy)-1H-[4,4']bipyrimidinyl-6-one (0.10 g, 0.35 mmol) and triethylamine (70 μl, 0.5 mmol) in dichloromethane (5 ml) was added methyl chloroformate (40 μl, 0.5 mmol) at 0° C. The resulting mixture was stirred for 2 hours and poured into 1N aqueous hydrochloric acid. The partitioned organic layer was dried over anhydrous sodium sulfate and concentrated in vacuo. The residue was purified by silica gel chromatography (eluent; chloroform/methanol=100/0 to 90/10) to afford methyl 3-(1-methyl-6-oxo-1,6-dihydro-[4,4']bipyrimidinyl-2-yloxy)piperidine-1-carboxylate as a white solid (52 mg, 0.15 mmol, 43%).

Examples 3-12

Preparation of Compounds Nos. 1.103-1.112

In the same manner as that of the above Example 1 or 2, compounds Nos. 1.103-1.112 listed in Table 1 were obtained.

Example 13

Preparation of Compound No. 1.201

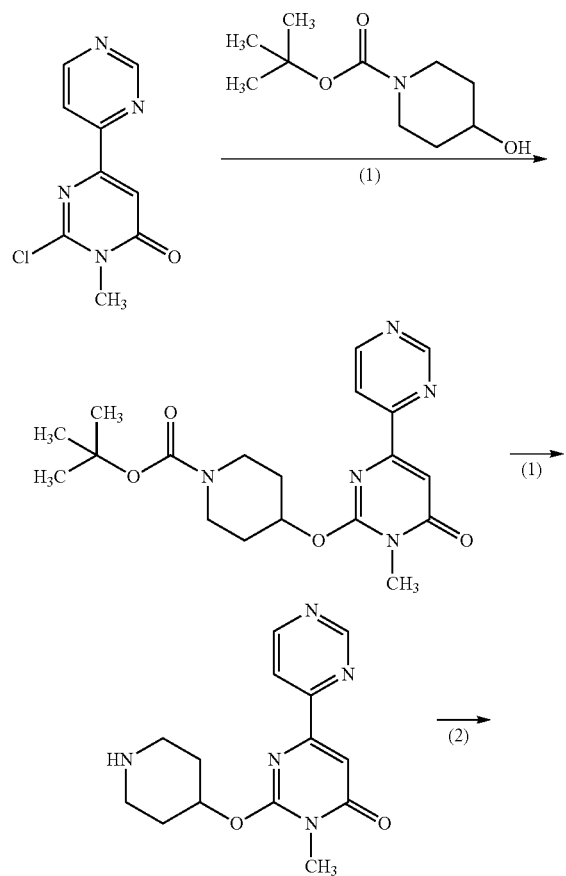

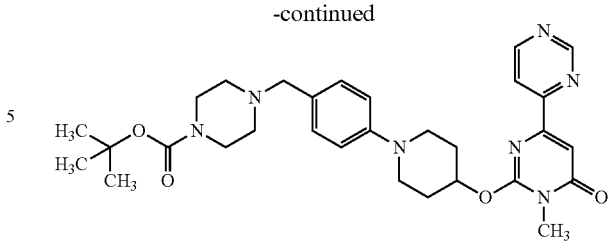

(1) To a solution of sodium hydride (60 wt % in mineral oil, 0.772 g, 19.3 mmol) in tetrahydrofuran (92 ml) was added tert-butyl 4-hydroxy-piperidine-1-carboxylate (3.70 g, 18.4 mmol) at 0° C. The mixture was stirred at room temperature for one hour, then 2-chloro-1-methyl-1H-[4,4']bipyrimidinyl-6-one (4.09 g, 18.4 mmol) was added. The mixture was stirred overnight. The mixture was partitioned between water and ethyl acetate. The organic layer was washed with brine, dried over sodium sulfate, and concentrated in vacuo. The residue was dissolved into dichloromethane (37 ml), and trifluoroacetic acid (41.9 g, 368 mmol) was added to the solution. The mixture was stirred at room temperature for 5 hours. After concentration under reduced pressure, the residue was dissolved into water. The aqueous solution was washed with ethyl acetate and basified with potassium carbonate. Extraction with chloroform was performed three times. The organic layer was dried over sodium sulfate and concentrated in vacuo to afford 1-methyl-2-(piperidin-4-yloxy)-1H-[4,4']bipyrimidinyl-6-one as a pale yellow solid (2.48 g, 8.63 mmol, 47%). This compound was used for the next reaction without further purification.

(2) To a mixture of tert-butyl 4-(4-bromo-benzyl)piperazine-1-carboxylate (371 mg, 1.04 mmol), 1-methyl-2-(piperidin-4-yloxy)-1H-[4,4']bipyrimidinyl-6-one (300 mg, 1.04 mmol), tris(dibenzylideneacetone)dipalladium(0)-chloroform adduct (43.2 mg, 41.8 µmol) and 2-dicyclohexylphosphino-2',4',6'-triisopropylbiphenyl (79.6 mg, 0.167 mmol) in toluene (2.09 ml) was added sodium tert-butoxide (151 mg, 1.57 mmol) under nitrogen atmosphere. The mixture was stirred at 150° C. for 30 minutes in Biotage Microwave reactor. The mixture was filtered through a pad of Celite, and concentrated in vacuo. The residue was purified by NH-silica gel column chromatography (eluent; hexane/ethyl acetate=1/1) to afford tert-butyl 4-{4-[4-(1-methyl-6-oxo-1,6-dihydro-[4,4']bipyrimidinyl-2-yloxy)piperidin-1-yl]benzyl}piperazine-1-carboxylate as a pale yellow solid (236 mg, 0.420 mmol, 40%).

Example 14

Preparation of Compound No. 1.202

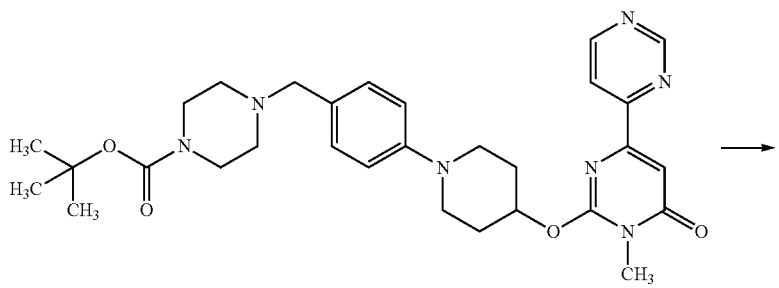

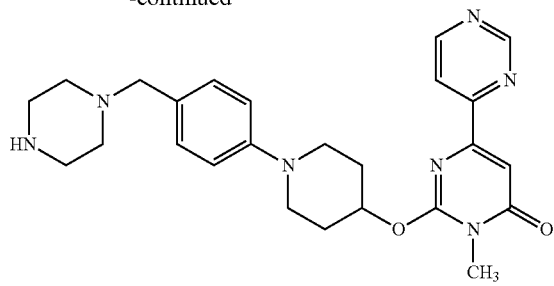

To a solution of tert-butyl 4-{4-[4-(1-methyl-6-oxo-1,6-dihydro-[4,4']bipyrimidinyl-2-yloxy)piperidin-1-yl]benzyl}piperazine-1-carboxylate (470 mg, 0.83 mmol) in dichloromethane (4.2 ml) was added trifluoroacetic acid (3.9 g, 34 mmol) at room temperature. The mixture was stirred overnight. After concentration under reduced pressure, the residue was dissolved into water. The aqueous solution was washed with ethyl acetate and basified with potassium carbonate. Extraction with chloroform was performed three times and the organic layer was dried over sodium sulfate, concentrated in vacuo to afford 1-methyl-2-[1-(4-piperazin-1-ylmethyl-phenyl)piperidin-4-yloxy]-1H-[4,4']bipyrimidinyl-6-one as a pale yellow solid (260 mg, 0.56 mmol, 67%).

Example 15

Preparation of Compound No. 1.203

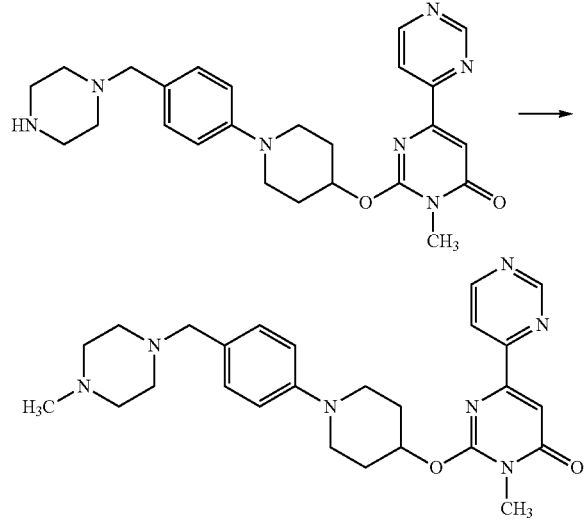

To a mixture of 1-methyl-2-[1-(4-piperazin-1-ylmethyl-phenyl)piperidin-4-yloxy]-1H-[4,4']bipyrimidinyl-6-one (80 mg, 0.17 mmol), formaldehyde solution (37% in water, 55 mg, 0.68 mmol) and acetic acid (one drop) in 1,2-dichloroethane (0.85 ml) was added sodium triacetoxyborohydride (130 mg, 0.61 mmol). The mixture was stirred at room temperature for 2 hours. The mixture was partitioned between water and chloroform. The organic layer was dried over sodium sulfate, and concentrated in vacuo. The residue was purified by silica gel column chromatography (eluent; chloroform/methanol=95/5) to afford 1-methyl-2-{1-[4-(4-methyl-piperazin-1-ylmethyl)phenyl]piperidin-4-yloxy}-1H-[4,4']bipyrimidinyl-6-one as a colorless solid (49 mg, 0.10 mmol, 59%)

Examples 16-46

Preparation of Compounds Nos. 1.204-1.234

In the same manner as that of the above Example 13, 14, or 15, compounds Nos. 1.204-1.234 listed in Table 1 were obtained.

Example 47

Preparation of the Compound No. 1.301

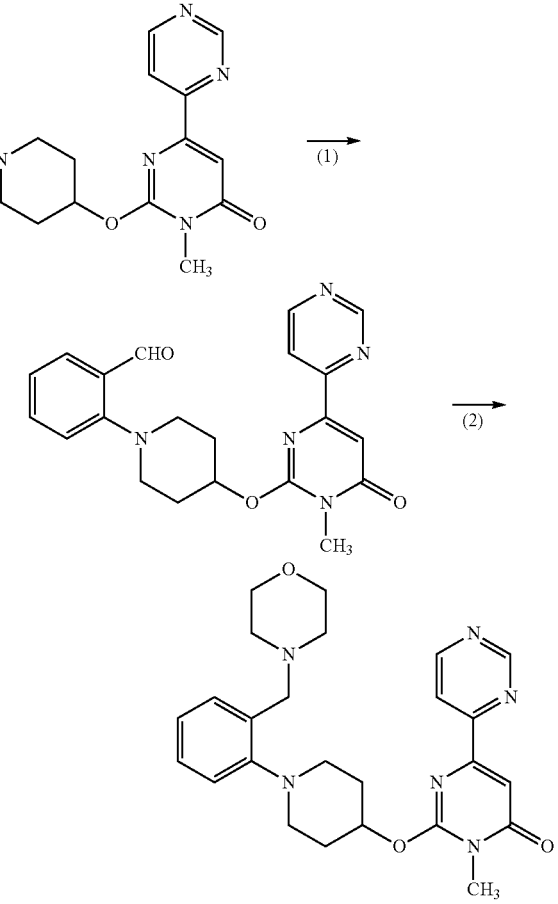

(1) To a mixture of 1-methyl-2-(piperidin-4-yloxy)-1H-[4,4']bipyrimidinyl-6-one (1.00 g, 3.48 mmol) and 2-fluorobenzaldehyde (475 mg, 3.83 mmol) in dimethyl sulfoxide (3.50 ml) was added potassium carbonate (1.44 g, 10.4 mmol). The mixture was stirred at 120° C. for 4 hours. The mixture was partitioned between water and chloroform. The organic layer was washed with water (three times), dried over sodium sulfate, and concentrated in vacuo. The residue was purified by silica gel column chromatography (eluent; ethyl acetate) to afford 2-[4-(1-methyl-6-oxo-1,6-dihydro-[4,4']bipyrimidinyl-2-yloxy)piperidin-1-yl]benzaldehyde as a yellow solid (711 mg, 1.82 mmol, 52%).

(2) To a mixture of 2-[4-(1-methyl-6-oxo-1,6-dihydro-[4,4']bipyrimidinyl-2-yloxy)piperidin-1-yl]benzaldehyde (80 mg, 0.20 mmol), morpholine (27 mg 0.31 mmol) and acetic acid (one drop) in 1,2-dichloroethane (1.0 ml) was added sodium triacetoxyborohydride (110 mg, 0.52 mmol). The mixture was stirred at room temperature for 2 hours. The mixture was partitioned between water and chloroform. The organic layer was washed with saturated aqueous sodium hydrogen carbonate, dried over sodium sulfate, and concentrated in vacuo. The residue was purified by silica gel column chromatography (eluent; chloroform/methanol=95/5) to afford 1-methyl-2-[1-(2-morpholin-4-ylmethyl-phenyl)piperidin-4-yloxy]-1H-[4,4']bipyrimidinyl-6-one as a colorless solid (63 mg, 0.14 mmol, 67%).

Examples 48-51

Preparation of Compounds Nos. 1.302-1.305

In the same manner as that of Example 47, compounds Nos. 1.302-1.305 listed in Table 1 were obtained.

Example 52

Preparation of the Compound No. 1.401

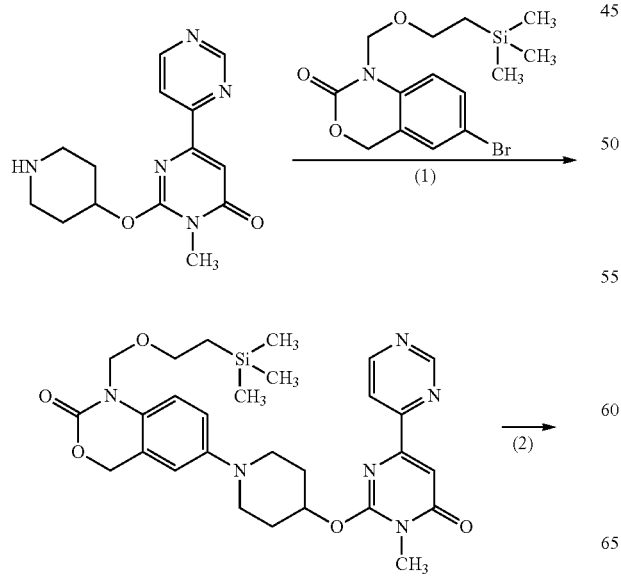

-continued

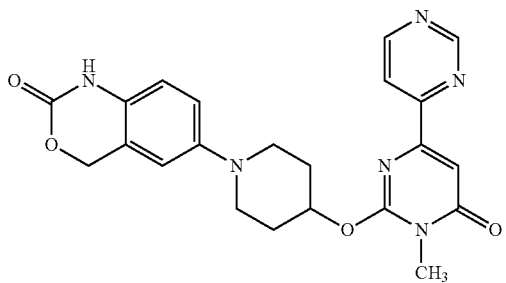

(1) To a mixture of 6-bromo-1-{[2-(trimethylsilyl)ethoxy]methyl}-1,4-dihydro-2H-3,1-benzoxazin-2-one (620 mg, 1.7 mmol), 1-methyl-2-(piperidin-4-yloxy)-1H-[4,4']bipyrimidinyl-6-one (500 mg, 1.7 mmol), tris(dibenzylideneacetone)dipalladium(0)-chloroform adduct (72 mg, 70 μmol), and 2-dicyclohexylphosphino-2',4',6'-triisopropylbiphenyl (130 mg, 0.28 mmol) in toluene (3.5 ml) was added sodium tert-butoxide (250 mg, 2.6 mmol) under nitrogen atmosphere. The mixture was stirred at 150° C. for 30 minutes utilizing Biotage microwave reactor. The mixture was filtered through a pad of Celite and concentrated in vacuo. The residue was purified by silica gel column chromatography (eluent; ethyl acetate) to afford 1-methyl-2-{[1-(2-oxo-1{[2-(trimethylsilyl)ethoxy]methyl}-1,4-dihydro-2H-3,1-benzoxazin-6-yl)piperidin-4-yl]oxy}-1H-[4,4']bipyrimidinyl-6-one as a pale yellow solid (110 mg, 0.19 mmol, 11%).

(2) To a solution of 1-methyl-2-{[1-(2-oxo-1{[2-(trimethylsilyl)ethoxy]methyl}-1,4-dihydro-2H-3,1-benzoxazin-6-yl)piperidin-4-yl]oxy}-1H-[4,4']bipyrimidinyl-6-one (78 mg, 0.14 mmol) in tetrahydrofuran (1.4 ml) was added 6N aqueous hydrochloric acid (1.4 ml, 8.4 mmol). The mixture was stirred at 70° C. for 3 hours. The mixture was poured into water. The aqueous solution was neutralized with sodium hydrogen carbonate. Extraction with dichloromethane was performed three times. The organic layer was dried over sodium sulfate and concentrated in vacuo. The residue was purified by silica gel column chromatography (eluent; chloroform/methanol=98/2) to afford 1-methyl-2-{[1-(2-oxo-1,4-dihydro-2H-3,1-benzoxazin-6-yl)piperidin-4-yl]oxy}-1H-[4,4']bipyrimidinyl-6-one as a pale yellow solid (22 mg, 0.051 mmol, 38%).

Example 53

Preparation of Compound No. 1.501

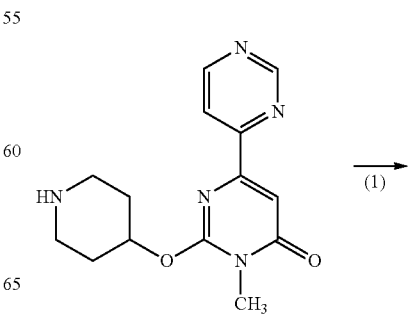

-continued

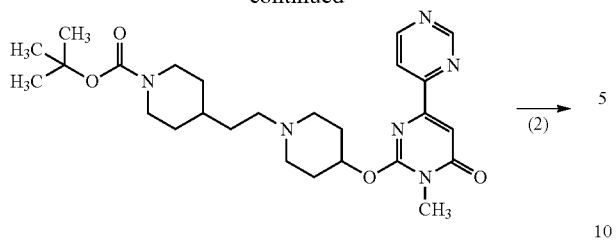

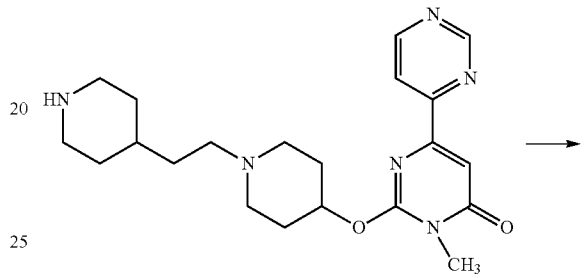

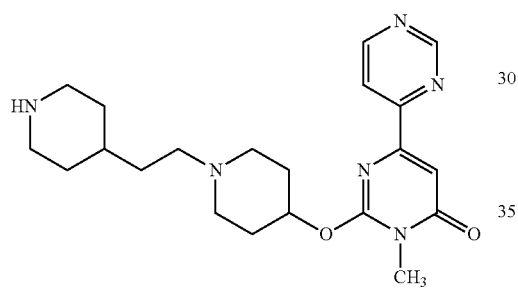

(1) To a mixture of 1-methyl-2-(piperidin-4-yloxy)-1H-[4,4']bipyrimidinyl-6-one (290 mg, 1.0 mmol), tert-butyl 4-(2-oxo-ethyl)piperidine-1-carboxylate (300 mg 1.3 mmol) and acetic acid (one drop) in 1,2-dichloroethane (5.0 ml) was added sodium triacetoxyborohydride (530 mg, 2.5 mmol). The mixture was stirred at room temperature overnight. The mixture was partitioned between water and dichloromethane. The organic layer was washed with brine, dried over sodium sulfate, and concentrated in vacuo. The residue was purified by NH-silica gel column chromatography (eluent; hexane/ethyl acetate=30/70) to afford tert-butyl 4-{2-[4-(1-methyl-6-oxo-1,6-dihydro-[4,4']bipyrimidinyl-2-yloxy)piperidin-1-yl]ethyl}piperidine-1-carboxylate as a colorless solid (340 mg, 0.67 mmol, 67%).

(2) To a solution of tert-butyl 4-{2-[4-(1-methyl-6-oxo-1,6-dihydro-[4,4]bipyrimidinyl-2-yloxy)piperidin-1-yl]ethyl}piperidine-1-carboxylate (326 mg, 0.654 mmol) in ethanol (6.54 ml) was added 2N hydrogen chloride in ethanol (9.81 ml, 19.6 mmol) at room temperature. The mixture was stirred at room temperature for 3 hours. After concentration under reduced pressure, the residue was dissolved into water. The aqueous solution was washed with ethyl acetate and basified with potassium carbonate. Extraction with chloroform was performed three times. The organic layer was dried over sodium sulfate and concentrated in vacuo to afford 1-methyl-2-[1-(2-piperidin-4-yl-ethyl)piperidin-4-yloxy]-1H-[4,4']bipyrimidinyl-6-one as pale yellow solid (207 mg, 0.519 mmol, 79%).

Example 54

Preparation of Compound No. 1.502

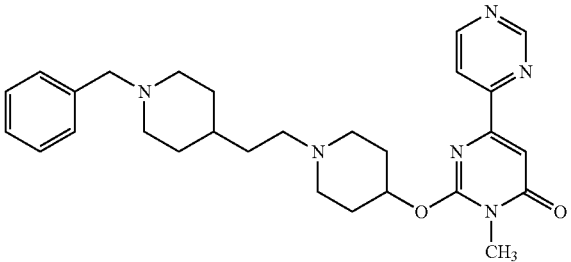

To a mixture of 1-methyl-2-[1-(2-piperidin-4-yl-ethyl)piperidin-4-yloxy]-1H-[4,4']bipyrimidinyl-6-one (40 mg, 0.10 mmol), benzaldehyde (16 mg, 0.15 mmol) and acetic acid (one drop) in 1,2-dichloroethane (0.5 ml) was added sodium triacetoxyborohydride (53 mg, 0.25 mmol). The mixture was stirred at room temperature overnight. The mixture was partitioned between water and dichloromethane. The organic layer was washed with brine, dried over sodium sulfate, and concentrated in vacuo. The residue was purified by NH-silica gel column chromatography (eluent; hexane/ethyl acetate=20/80) to afford 2-{1-[2-(1-benzyl-piperidin-4-yl)

ethyl]piperidin-4-yloxy}-1-methyl-1H-[4,4']bipyrimidinyl-6-one as a colorless solid (35 mg, 0.71 mmol, 71%).

Examples 55-57

Preparation of Compounds Nos. 1.503-1.505

In the same manner as that of the above Example 53 or 54, compounds Nos. 1.503-1.505 listed in Table 1 were obtained.

Example 58

Preparation of Compound No. 1.601

To a mixture of 1-methyl-2-(piperidin-4-yloxy)-1H-[4,4']bipyrimidinyl-6-one (290 mg, 1.0 mmol), 4-dimethylaminomethyl benzoic acid (180 mg, 1.0 mmol), N-(3-dimethylaminopropyl)-N'-ethylcarbodiimide hydrochloride (380 mg, 2.0 mmol) and 1-hydroxybenzotriazole monohydrate (310 mg, 2.0 mmol) in N,N-dimethylformamide (10 ml) was added N,N-diisopropylethylamine (130 mg, 1.0 mmol) at room temperature. The mixture was stirred at room temperature for 3 hours. The mixture was partitioned between water and dichloromethane. The organic layer was washed with water (three times), dried over sodium sulfate, and concentrated in vacuo. The residue was purified by NH-silica gel column chromatography (eluent; hexane/ethyl acetate=15/85) to afford 2-[1-(4-dimethylaminomethyl-benzoyl)piperidin-4-yloxy]-1-methyl-1H-[4,4']bipyrimidinyl-6-one as a colorless solid (66 mg, 0.15 mmol, 15%).

Example 59

Preparation of Compound No. 1.701

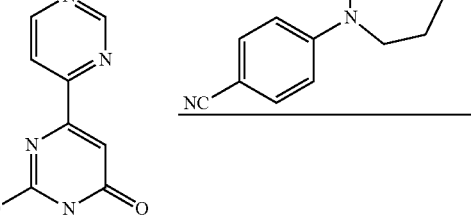

To a mixture of 4-(4-hydroxy-azepan-1-yl)benzonitrile (300 mg, 1.39 mmol), 2-hydroxy-1-methyl-1H-[4,4']bipyrimidinyl-6-one (312 mg, 1.53 mmol), triphenylphosphine (400 mg, 1.53 mmol) in tetrahydrofuran (4.6 ml) was added diisopropyl azodicarboxylate (40 wt % in toluene, 771 mg, 1.53 mmol) under nitrogen atmosphere. The mixture was stirred at room temperature overnight. Then the precipitate was collected, and purified by silica gel column chromatography (eluent; ethyl acetate) to afford 4-[4-(1-methyl-6-oxo-1,6-dihydro-[4,4']bipyrimidinyl-2-yloxy)azepan-1-yl]benzonitrile as a colorless solid (360 mg, 0.89 mmol, 64%).

Example 60

Preparation of Compound No. 1.801

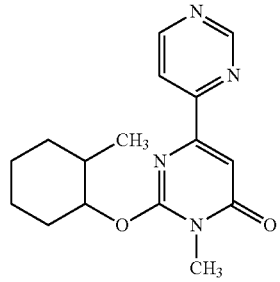

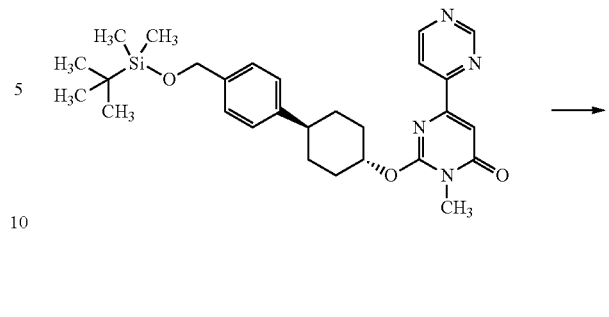

To a solution of sodium hydride (60 wt % in mineral oil, 326 mg, 8.15 mmol) in tetrahydrofuran (14.0 ml) was added 1-methyl cyclohexanol (racemate; cis/trans mixture, 930 mg, 8.15 mmol) at room temperature. The mixture was stirred at 40° C. for one hour. The mixture was cooled to room temperature, and 2-chloro-1-methyl-1H-[4,4']bipyrimidinyl-6-one (1.51 g, 6.78 mmol) was added to the mixture. The mixture was stirred at 60° C. for 8 hours. The mixture was partitioned between water and ethyl acetate. The organic layer was washed with brine, dried over sodium sulfate, and concentrated in vacuo. The residue was purified by silica gel column chromatography (eluent; ethyl acetate) to afford 1-methyl-2-(2-methyl-cyclohexyloxy)-1H-[4,4']bipyrimidinyl-6-one (cis/trans-mixture) as a colorless solid (752 mg, 2.50 mmol, 37%)

Examples 61-69

Preparation of Compounds Nos. 1.802-1.810

In the same manner as that of the above Example 60, compounds Nos. 1.802-1.810 listed in Table 1 were obtained.

Example 70

Preparation of the Compound No. 1.901

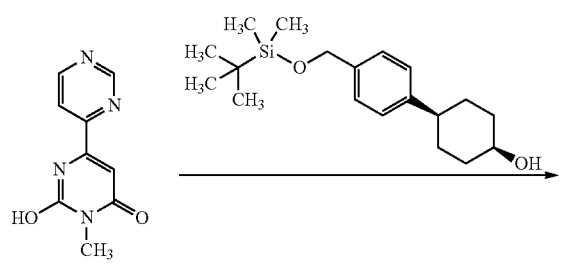

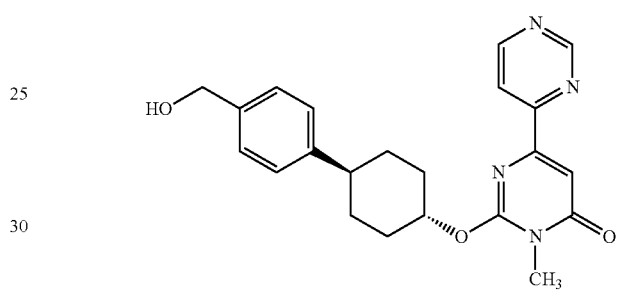

To a mixture of cis-4-[4-(tert-butyl-dimethyl-silanyloxymethyl)phenyl]cyclohexanol (600 mg, 1.87 mmol), 2-hydroxy-1-methyl-1H-[4,4']bipyrimidinyl-6-one (382 mg, 1.87 mmol), triphenylphosphine (540 mg, 2.06 mmol) in tetrahydrofuran (6.2 ml) was added diisopropyl azodicarboxylate (40 wt % in toluene, 1.04 g, 2.06 mmol) under nitrogen atmosphere. The mixture was stirred at room temperature overnight. The solvent was evaporated under reduced pressure, and the residue was purified by silica gel column chromatography (eluent; hexane/ethyl acetate=60/40 to 50/50) to afford a colorless solid. This compound was dissolved into tetrahydrofuran (7.5 ml) and cooled to 0° C. Tetrabutylammonium fluoride (1.0M in tetrahydrofuran, 3.0 ml, 3.0 mmol) was added to the solution. The mixture was warmed to room temperature and stirred for one hour. The mixture was poured into saturated aqueous ammonium chloride solution, and extracted with dichloromethane. The organic layer was dried over sodium sulfate and concentrated in vacuo. The residue was purified by silica gel column chromatography (eluent; ethyl acetate) to afford 2-[trans-4-(4-hydroxymethyl-phenyl)cyclohexyloxy]-1-methyl-1H-[4,4']bipyrimidinyl-6-one as a colorless solid (243 mg, 0.619 mmol, 33%).

Example 71

Preparation of Compound No. 1.902

In the same manner as that of the above Example 70 with the use of trans-4-[4-(tert-butyl-dimethyl-silanyloxymethyl)phenyl]cyclohexanol (600 mg, 1.87 mmol) instead of cis-4-

[4-(tert-butyl-dimethyl-silanyloxymethyl)phenyl]cyclohexanol, compound No. 1.902 listed in Table 1 was obtained (377 mg, 0.961 mmol, 51%).

Example 72

Preparation of Compound No. 1.903

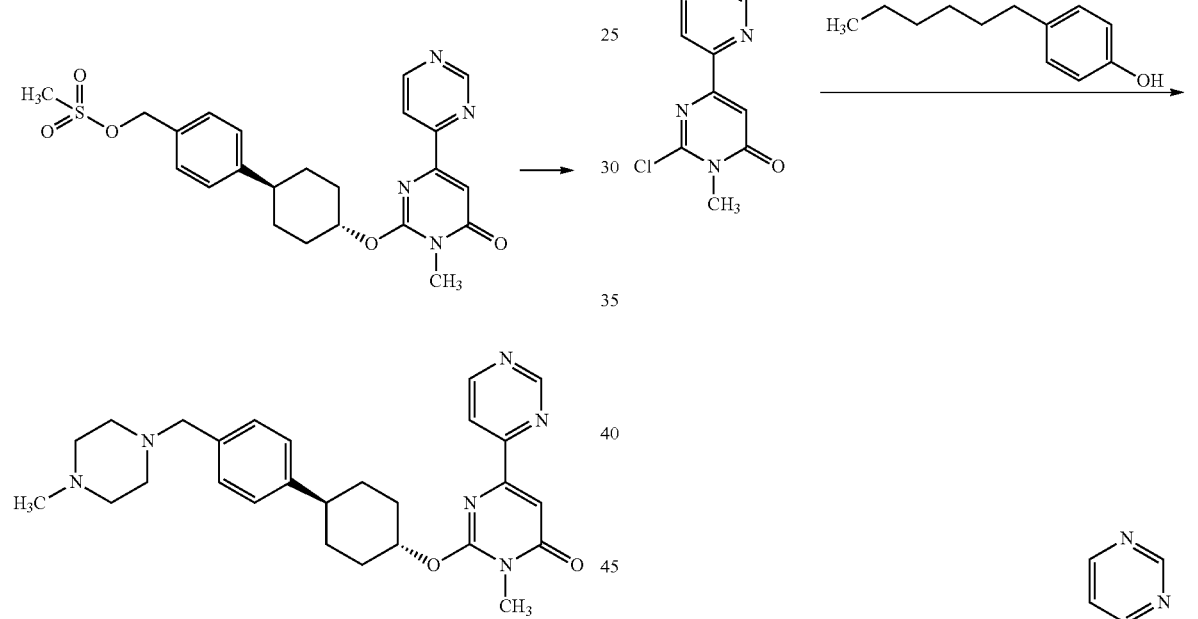

To a mixture of 2-[trans-4-(4-hydroxymethyl-phenyl)cyclohexyloxy]-1-methyl-1H-[4,4']bipyrimidinyl-6-one (100 mg, 0.255 mmol) and triethylamine (51.6 mg, 0.510 mmol) in dichloromethane (1.3 ml) was added methanesulfonyl chloride (32.1 mg, 0.28 mmol) at 0° C. The mixture was warmed to room temperature and stirred overnight. The mixture was partitioned between water and dichloromethane. The organic layer was washed with brine, dried over sodium sulfate, and concentrated in vacuo. The residue was dissolved into tetrahydrofuran (1.3 ml) and N,N-dimethylformamide (0.3 ml). 1-Methylpiperazine (30.6 mg, 0.306 mmol) and potassium carbonate (52.8 mg, 0.382 mmol) was added to the solution. The mixture was stirred at 60° C. for 3 hours. The mixture was poured into water, and extracted with chloroform. The organic layer was washed with water (three times), dried over sodium sulfate, and concentrated in vacuo. The residue was purified by NH-silica gel column chromatography (eluent; ethyl acetate) to afford 1-methyl-2-{trans-4-[4-(4-methyl-piperazin-1-ylmethyl)phenyl]cyclohexyloxy}-1H-[4,4']bipyrimidinyl-6-one as a colorless solid (51.1 mg, 0.108 mmol, 42%).

Example 73

Preparation of Compound No. 1.904

In the same manner as that of the above Example 71 and 72, compound No. 1.904 listed in Table 1 was obtained.

Example 74

Preparation of Compound No. 2.001

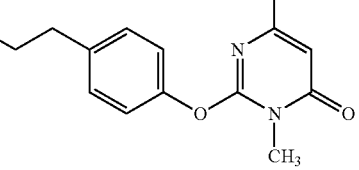

To a solution of sodium hydride (60 wt % in mineral oil, 202 mg, 5.05 mmol) in N,N-dimethylformamide (1.0 ml) was added 4-hexylphenol (899 mg, 5.04 mmol) at room temperature, and stirred for one hour. 2-Chloro-1-methyl-1H-[4,4'] bipyrimidinyl-6-one (935 mg, 4.20 mmol) was added to the solution. The mixture was stirred at room temperature overnight. The mixture was poured into water, and extracted with dichloromethane. The organic layer was washed with water (three times), dried over sodium sulfate, and concentrated in vacuo. The residue was purified by silica gel column chromatography (eluent; hexane/ethyl acetate=50/50) to afford 2-(4- hexylphenoxy)-1-methyl-1H-[4,4']bipyrimidinyl-6-one as a colorless solid (1.14 g, 3.13 mmol, 75%).

Examples 75-76

Preparation of Compounds Nos. 2.002 and 2.003

In the same manner as that of the above Example 74, compounds Nos. 2.002 and 2.003 listed in Table 1 were obtained.

Example 77

Preparation of Compound No. 2.101

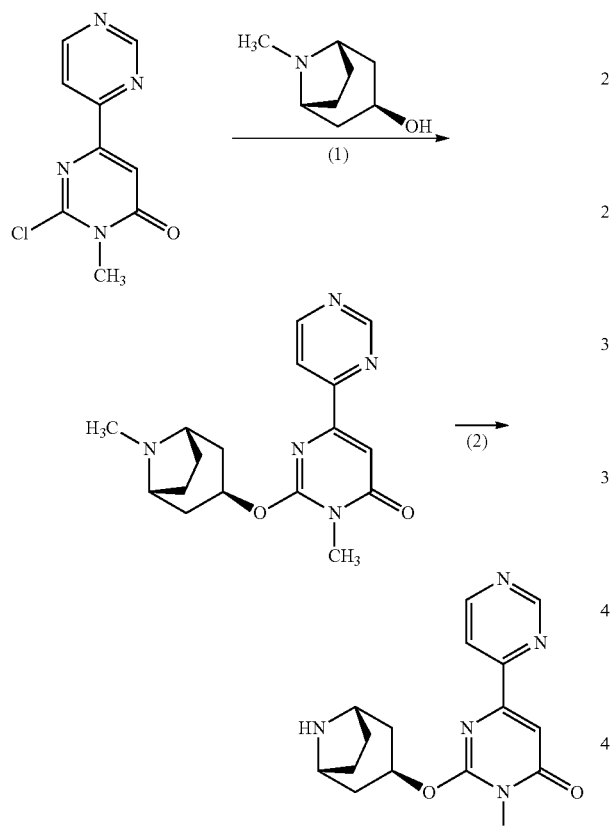

(1) To a solution of sodium hydride (60 wt % in mineral oil, 156 mg, 3.89 mmol) in N,N-dimethylformamide (7.0 ml) was added tropine (purchased from Tokyo Chemical Industry Corporation, 500 mg, 3.54 mmol) at room temperature. The mixture was stirred at 50° C. for one hour. The mixture was cooled to room temperature, and 2-chloro-1-methyl-1H-[4,4']bipyrimidinyl-6-one (867 mg, 3.89 mmol) was added to the mixture. The mixture was stirred at 90° C. for 10 hours. The mixture was partitioned between water and ethyl acetate. The organic layer was washed with water (three times), dried over sodium sulfate, and concentrated in vacuo. The residue was purified by NH-silica gel column chromatography (eluent; ethyl acetate) to afford endo-1-methyl-2-(8-methyl-8-aza-bicyclo[3.2.1]oct-3-yloxy)-1H-[4,4']bipyrimidinyl-6-one as a colorless solid (97.2 mg, 0.297 mmol, 8%).

(2) To a solution of endo-1-methyl-2-(8-methyl-8-aza-bicyclo[3.2.1]oct-3-yloxy)-1H-[4,4']bipyrimidinyl-6-one (90 mg, 0.28 mmol) in 1,2-dichloroethane (0.92 ml) was added 1-chloroethyl chloroformate (98 mg, 0.69 mmol) at room temperature. The mixture was refluxed for 4 hours. The mixture was cooled to room temperature, then methanol (2.0 ml) was added to the mixture. The mixture was refluxed for 3 hours. After concentration under reduced pressure, the residue was dissolved into water. The aqueous solution was basified with potassium carbonate. Extraction with chloroform was performed three times and the organic layer was dried over sodium sulfate, and concentrated in vacuo. The residue was purified by NH-silica gel column chromatography (eluent; ethyl acetate to chloroform) to afford endo-2-(8-aza-bicyclo[3.2.1]oct-3-yloxy)-1-methyl-1H-[4,4']bipyrimidinyl-6-one as a pale yellow solid (37 mg, 0.12 mmol, 43%).

Example 78

Preparation of Compound No. 2.102

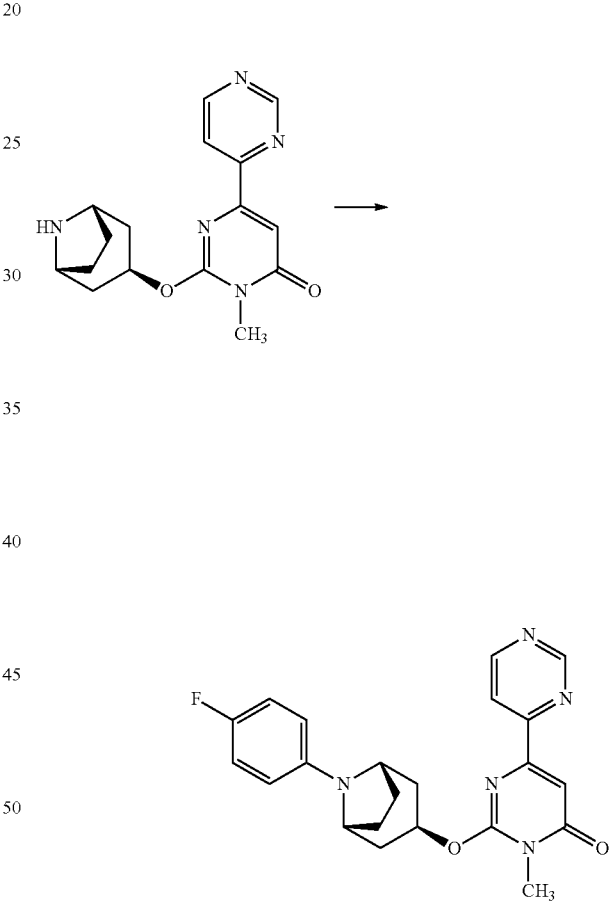

To a mixture of endo-2-(8-aza-bicyclo[3.2.1]oct-3-yloxy)-1-methyl-1H-[4,4']bipyrimidinyl-6-one (30 mg, 96 μmol), 1-bromo-4-fluorobenzene (18 mg, 110 μmol), tris(dibenzylideneacetone)dipalladium(0)-chloroform adduct (4.0 mg, 3.9 μmol), and 2-dicyclohexylphosphino-2',4',6'-triisopropylbiphenyl (7.3 mg, 15 μmol) in toluene (0.45 ml) was added sodium tert-butoxide (14 mg, 140 μmol) under nitrogen atmosphere. The mixture was refluxed for 8 hours. The mixture was filtered through a pad of Celite, and concentrated in vacuo. The residue was purified by NH-silica gel column chromatography (eluent; hexane/ethyl acetate=20/80) to afford endo-2-[8-(4-Fluoro-phenyl)-8-aza-bicyclo[3.2.1]

oct-3-yloxy]-1-methyl-1H-[4,4']bipyrimidinyl-6-one as a pale yellow solid (15 mg, 37 μmol, 38%).

Example 79

Preparation of Compound No. 2.201

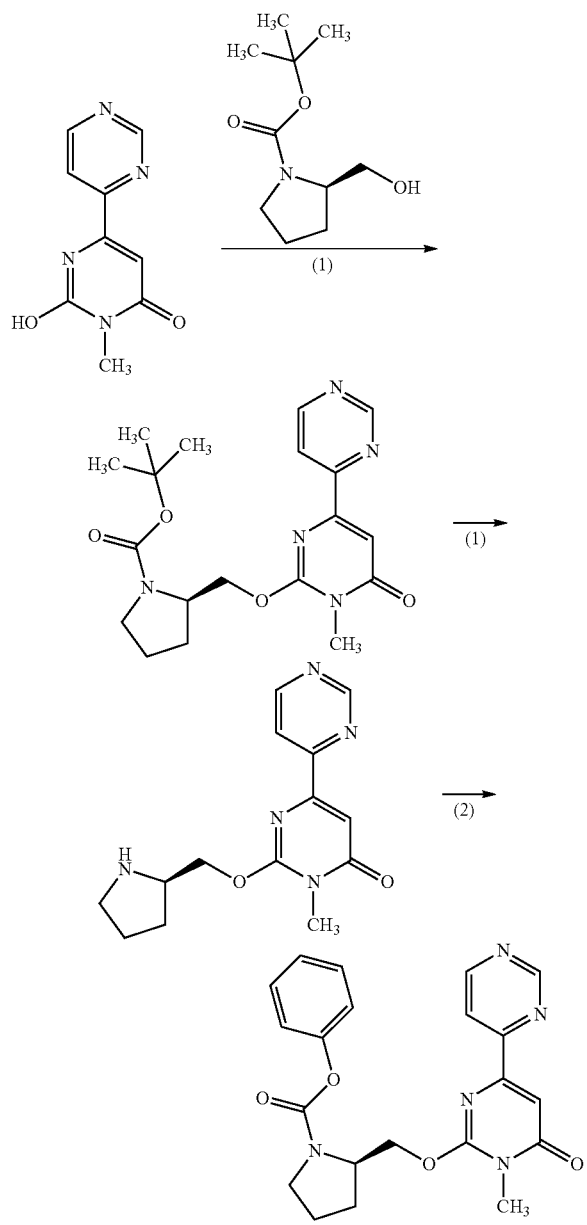

(1) To a solution of (R)-tert-butyl 2-(hydroxymethyl)pyrrolidine-1-carboxylate (5.0 g, 24.8 mmol) in tetrahydrofuran (150 ml) under nitrogen atmosphere were added triphenylphosphine (6.8 g, 25.9 mmol), 40 wt % toluene solution of diethyl azodicarboxylate (11.8 ml), and 2-hydroxy-1-methyl-1H-4,4']bipyrimidinyl-6-one (5.0 g, 24.5 mmol). The brown mixture was stirred overnight and concentrated in vacuo. The residue was passed through short column chromatography (eluent; chloroform/methanol=90/10) to remove phosphine compounds. To the obtained material in chloroform (100 ml) at room temperature was added trifluoroacetic acid (40 ml). The resulting solution was stirred overnight and concentrated in vacuo. The residue was dissolved into water, basified with potassium carbonate, and extracted with chloroform. The organic layer was dried over anhydrous sodium sulfate and concentrated in vacuo. The residue was purified by silica gel column chromatography (eluent; chloroform/methanol=90/10) to afford (R)-1-methyl-2-(pyrrolidin-2-ylmethoxy)-1H-[4,4']bipyrimidinyl-6-one as a white solid (4.0 g, 13.9 mmol, 57%).

(2) Phenyl (2R)-2-(1-methyl-6-oxo-1,6-dihydro-[4,4]bipyrimidinyl-2-yloxymethyl)pyrrolidine-1-carboxylate was prepared by the same manner as that of methyl 3-(1-methyl-6-oxo-1,6-dihydro-[4,4']bipyrimidinyl-2-yloxy)piperidine-1-carboxylate except for utilizing (R)-1-methyl-2-(pyrrolidin-2-ylmethoxy)-1H-[4,4']bipyrimidinyl-6-one (0.20 g, 0.70 mmol) instead of 1-methyl-2-(piperidine-3-yloxy)-1H-[4,4']bipyrimidinyl-6-one and phenyl chloroformate (125 μl, 1.0 mmol) instead of methyl chloroformate. Phenyl (2R)-2-(1-methyl-6-oxo-1,6-dihydro-[4,4']bipyrimidinyl-2-yloxymethyl)pyrrolidine-1-carboxylate was isolated as a white solid (29 mg, 0.07 mmol, 10%).

Examples 80-81

Preparation of the Compounds Nos. 2.202-2.203

In the same manner as that of the above Example 1 or 79, the compounds of Nos. 2.202-2.203 listed in Table 1 were obtained.

Examples 82-83

Preparation of the Compounds Nos. 2.204-2.205

In the same manner as that of the above Example 1 or 79 with the use of (S)-tert-butyl 2-(hydroxymethyl)pyrrolidine-1-carboxylate (purchased from Sigma-Aldrich Corporation) instead of (R)-tert-butyl 2-(hydroxymethyl)pyrrolidine-1-carboxylate, the compounds of Nos. 2.204 (79 mg, 0.21 mmol) and 2.205 (106 mg, 0.27 mmol) listed in Table 1 were obtained respectively.

Example 84

Preparation of Compound No. 2.206

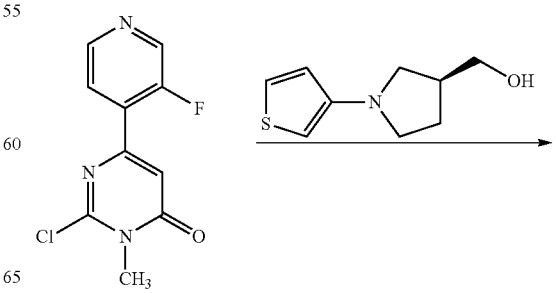

-continued

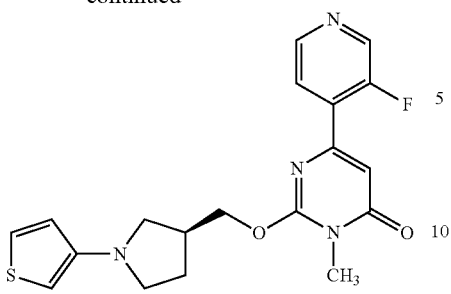

To a slurry of sodium hydride (60 wt % in mineral oil, 0.04 g, 1.0 mmol) in N,N-dimethylformamide (2 ml) under nitrogen atmosphere was added (S)-[1-(thiophen-3-yl)pyrrolidin-3-yl]methanol (0.13 g, 0.70 mmol) in N,N-dimethylformamide (1 ml) at room temperature. The resulting mixture was stirred for 15 minutes. To the mixture was added 2-chloro-6-(3-fluoro-pyridin-4-yl)-3-methyl-3H-pyrimidin-4-one (0.14 g, 0.60 mmol) at room temperature. After the mixture was stirred for 3 hours, the reaction was quenched with water and partitioned between water and ethyl acetate. The organic layer was dried over anhydrous sodium sulfate and concentrated in vacuo. The residue was purified by silica gel column chromatography (eluent; hexane/ethyl acetate=90/10 to 0/100) to afford 6-(3-fluoro-pyridin-4-yl)-3-methyl-2-[(3S)-1-thiophen-3-yl-pyrrolidin-3-ylmethoxy]-3H-pyrimidin-4-one (0.045 g, 0.12 mmol, 19%) as a yellow solid.

Example 85

Preparation of Compound No. 2.207

In the same manner as that of the above Example 84, compound No. 2.207 listed in Table 1 was obtained.

Example 86

Preparation of Compound No. 2.208

In the same manner as that of the above Example 84 with the use of (R)-[1-(thiophen-3-yl)pyrrolidin-3-yl]methanol (60 mg, 0.33 mmol) instead of (S)-[1-(thiophen-3-yl)pyrrolidin-3-yl]methanol, compound No. 2.208 listed in Table 1 was obtained (34 mg, 0.088 mmol, 27%).

Examples 87-88

Preparation of Compounds Nos. 2.209-2.210

In the same manner as that of the above Example 84, compounds Nos. 2.209-2.210 listed in Table 1 were obtained.

Example 89

Preparation of Compound No. 2.211

In the same manner as that of the above Example 86, compound No. 2.211 listed in Table 1 was obtained.

Example 90

Preparation of Compound No. 2.301

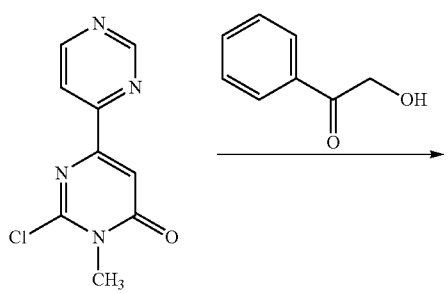

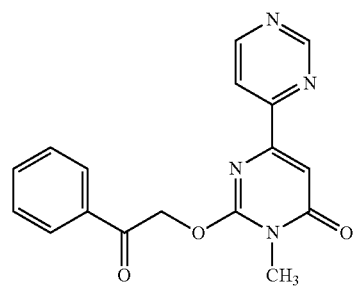

To a suspension of sodium hydride (60 wt % in oil, 0.23 g, 6.3 mmol) in tetrahydrofuran (5 ml) was added 2-hydroxyacetophenone (0.92 g, 6.75 mmol) in tetrahydrofuran (5 ml) and the mixture was stirred at room temperature. After 30 minutes, 2-chloro-1-methyl-1H-[4,4']bipyrimidinyl-6-one (1.0 g, 4.5 mmol) was added. The mixture was stirred under reflux for 8 hours. The mixture was cooled to room temperature and extracted with ethyl acetate. The organic layer was dried over sodium sulfate and concentrated in vacuo. The residue was purified by silica gel column chromatography (eluent; ethyl acetate) to afford 1-methyl-2-(2-oxo-2-phenyl-ethoxy)-1H-[4,4']bipyrimidinyl-6-one (75 mg, 0.23 mmol, 5%) as a colorless solid.

Examples 91-94

Preparation of Compounds Nos. 2.302-2.305

In the same manner as that of the above Example 90, compounds Nos 2.302-2305 listed in Table 1 were obtained.

Example 95

Preparation of Compound No. 2.401

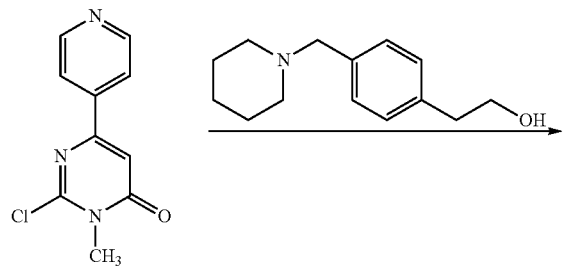

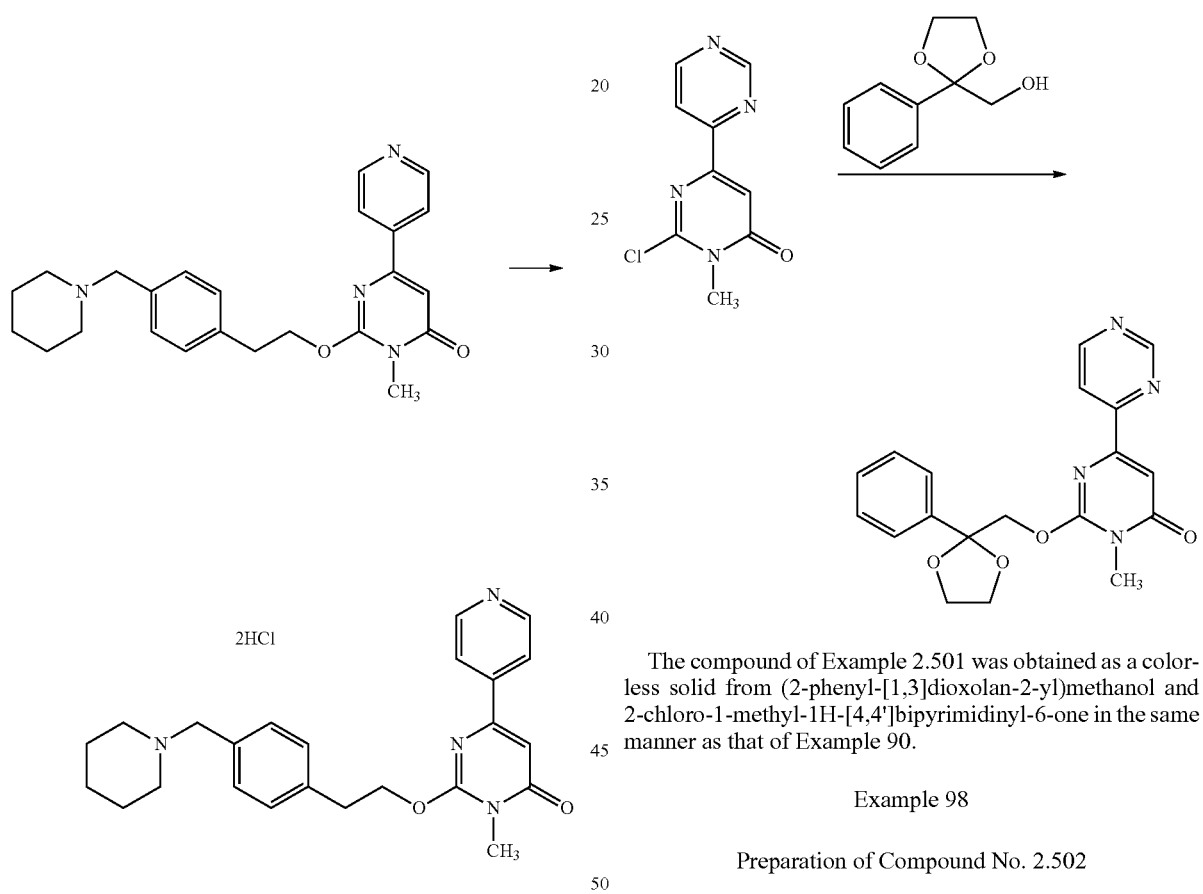

To a mixture of 2-chloro-3-methyl-6-pyridin-4-yl-3H-pyrimidin-4-one (500 mg, 2.26 mmol) and 2-(4-piperidin-1-ylmethyl-phenyl)ethanol (990 mg, 4.51 mmol) in N,N-dimethylformamide (15 ml) was added 1,8-diazabicyclo[5.4.0]undec-7-ene (347 mg, 2.26 mmol) at room temperature. The mixture was stirred at 100° C. for 4 hours. The mixture was poured into water and extracted with ethyl acetate. The organic layer was washed with brine, dried over sodium sulfate, and concentrated in vacuo. The residue was purified by silica gel column chromatography (eluent; ethyl acetate/methanol=90/10 to 67/33) to afford a pale blue powder. This compound was dissolved into ethyl acetate (1.2 ml), and 4N-hydrogen chloride in ethyl acetate (1.2 ml, 4.8 mmol) was added at room temperature. The mixture was stirred for 30 minutes, then the solvent was removed under reduced pressure to afford 3-methyl-2-[2-(4-piperidin-1-ylmethyl-phenyl)ethoxy]-6-pyridin-4-yl-3H-pyrimidin-4-one dihydrochloride as a pale purple solid (455 mg, 0.952 mmol, 42%).

Example 96

Preparation of Compound No. 2.402

In the same manner as that of the above Example 95, compound No. 2.402 listed in Table 1 was obtained.

Example 97

Preparation of Compound No. 2.501

The compound of Example 2.501 was obtained as a colorless solid from (2-phenyl-[1,3]dioxolan-2-yl)methanol and 2-chloro-1-methyl-1H-[4,4']bipyrimidinyl-6-one in the same manner as that of Example 90.

Example 98

Preparation of Compound No. 2.502

-continued

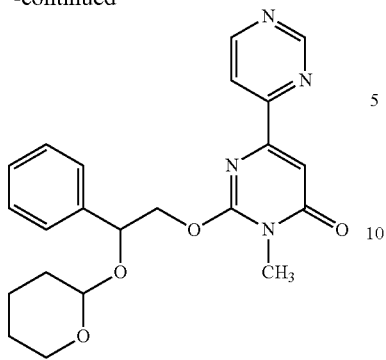

The compound was obtained as a colorless solid from 2-phenyl-2-(tetrahydropyran-2-yl-oxy)ethanol and 2-chloro-1-methyl-1H-[4,4']bipyrimidinyl-6-one in the same manner as that of Example 90.

The compounds in the following table were prepared in the same manner as the methods described above. The compound numbers in the following table correspond to those shown in the above-described table of preferred compounds.

TABLE 2

| COMPOUND NO. | NMR | MS [M + 1] |
|---|---|---|
| 1.101 | 1.65-1.73 (1H, m), 1.88-1.96 (2H, m), 2.10-2.16 (1H, m), 3.16 (3H, s), 3.23-3.31 (2H, m), 3.50 (1H, dd, J = 13.1, 6.8 Hz), 3.69 (1H, dd, J = 12.9, 2.7 Hz), 5.38-5.44 (1H, m), 6.73 (1H, t, J = 7.2 Hz), 6.93 (2H, d, J = 8.2 Hz), 7.04 (1H, s), 7.15-7.19 (2H, m), 8.23 (1H, dd, J = 5.1, 1.2 Hz), 9.04 (1H, d, J = 5.1 Hz), 9.33 (1H, d, J = 1.2 Hz) (DMSO-d6) | 364 |
| 1.102 | 1.56 (1H, td, J = 9.2, 4.3 Hz), 1.74-1.82 (1H, m), 1.98-2.02 (2H, m), 2.54 (3H, s), 3.29 (3H, s), 3.61-3.69 (3H, m), 3.86 (1H, br.), 5.32 (1H, br..), 7.05 (1H, s), 8.27 (1H, br.), 9.04 (1H, d, J = 4.7 Hz), 9.32 (1H, d, J = 1.6 Hz) (DMSO-d6) | 346 |
| 1.103 | 1.72-1.81 (1H, m), 1.87-2.03 (2H, m), 2.08-2.13 (1H, m), 3.04-3.17 (2H, m), 3.28 (1H, d, J = 7.1 Hz), 3.31 (3H, s), 3.47 (1H, dd, J = 12.10, 2.73 Hz), 5.42-5.48 (1H, m), 6.91-6.98 (1H, m), 7.04 (1H, s), 7.06-7.14 (3H, m), 8.23 (1H, dd, J = 5.1, 1.6 Hz), 9.03 (1H, d, J = 5.1 Hz), 9.32 (1H, d, J = 1.2 Hz) (DMSO-d6) | 382 |
| 1.104 | 1.61-1.70 (1H, m), 1.86-1.98 (2H, m), 2.08-2.16 (1H, m), 3.13 (3H, s), 3.35-3.40 (2H, m), 3.61 (1H, dd, J = 13.6, 6.3 Hz), 3.71 (1H, dd, J = 13.3, 2.7 Hz), 5.37-5.43 (1H, m), 6.48 (1H, td, J = 8.2, 2.0 Hz), 6.69-6.76 (2H, m), 7.04 (1H, s), 7.15 (1H, q, J = 8.1 Hz), 8.23 (1H, dd, J = 5.1, 1.2 Hz), 9.02 (1H, d, J = 5.1 Hz), 9.32 (1H, d, J = 1.2 Hz) (DMSO-d6) | 382 |
| 1.105 | 1.66-1.74 (1H, m), 1.84-1.97 (2H, m), 2.07-2.15 (1H, m), 3.14-3.30 (5H, m), 3.40 (1H, dd, J = 12.5, 6.6 Hz), 3.60 (1H, dd, J = 12.7, 2.9 Hz), 5.41-5.46 (1H, m), 6.93-7.05 (5H, m), 8.22 (1H, dd, J = 5.3, 1.4 Hz), 9.04 (1H, d, J = 5.1 Hz), 9.32 (1H, d, J = 1.2 Hz) (DMSO-d6) | 382 |
| 1.106 | 1.64-1.71 (1H, m), 1.87-1.95 (2H, m), 2.09-2.16 (1H, m), 3.15 (3H, s), 3.24-3.31 (1H, m), 3.52 (2H, dd, J = 13.1, 6.8 Hz), 3.64 (3H, s), 3.69 (1H, dd, J = 13.3, 2.7 Hz), 5.36-5.41 (1H, m), 6.31 (1H, dd, J = 8.0, 2.2 Hz), 6.41 (1H, t, J = 2.2 Hz), 6.51 (1H, dd, J = 8.2, 2.0 Hz), 7.04 (1H, s), 7.05-7.09 (1H, m), 8.23 (1H, dd, J = 5.3, 1.4 Hz), 9.02 (1H, d, J = 5.1 Hz), 9.32 (1H, d, J = 1.2 Hz) (DMSO-d6) | 394 |
| 1.107 | 1.69-1.77 (1H, m), 1.79-1.97 (2H, m), 2.08-2.15 (1H, m), 3.05 (1H, ddd, J = 11.9, 8.6, 3.3 Hz), 3.18-3.29 (5H, m), 3.56 (1H, dd, J = 12.5, 3.1 Hz), 3.67 (3H, s), 5.39-5.45 (1H, m), 6.77-6.81 (2H, m), 6.88-6.93 (2H, m), 7.04 (1H, s), 8.22 (1H, dd, J = 5.3, 1.4 Hz), 9.03 (1H, d, J = 5.5 Hz), 9.32 (1H, d, J = 1.6 Hz) (DMSO-d6) | 394 |
| 1.108 | 1.56-1.65 (1H, m), 1.83-1.92 (1H, m), 1.95-2.04 (1H, m), 2.10-2.18 (1H, m), 2.97 (3H, s), 3.49-3.57 (1H, m), 3.75 (1H, ddd, J = 13.6, 5.8, 3.3 Hz), 3.92 (1H, dd, J = 13.7, 2.7 Hz), 4.13 (1H, dd, J = 13.7, 5.5 Hz), 5.35 (1H, tt, J = 5.9, 3.1 Hz), 6.57 (1H, dd, J = 6.6, 5.1 Hz), 6.82 (1H, d, J = 8.6 Hz), 7.04 (1H, s), 7.48 (1H, ddd, J = 8.7, 6.9, 2.0 Hz), 7.97 (1H, dd, J = 4.9, 1.4 Hz), 8.30 (1H, dd, J = 5.1, 1.2 Hz), 9.04 (1H, d, J = 5.1 Hz), 9.33 (1H, d, J = 1.6 Hz) (DMSO-d6) | 365 |
| 1.109 | 1.69 (1H, br.), 1.82-1.93 (3H, m), 2.98-3.06 (1H, m), 3.14-3.23 (1H, m), 3.40-3.47 (2H, m), 5.35 (1H, dt, J = 5.6, 2.9 Hz), 7.06 (1H, s), 7.58-7.65 (2H, m), 7.67-7.73 (1H, m), 7.73-7.77 (2H, m), 8.24 (1H, dd, J = 5.1, 1.2 Hz), 9.05 (1H, d, J = 5.1 Hz), 9.33 (1H, d, J = 1.6 Hz) (DMSO-d6) | 428 |
| 1.110 | 1.86-1.97 (2H, m), 2.05-2.14 (2H, m), 3.48 (3H, s), 3.54-3.60 (2H, m), 3.75-3.82 (2H, m), 5.17 (2H, s), 5.46-5.51 (1H, m), 7.27 (1H, s), 7.32-7.39 (5H, m), 8.05 (1H, dd, | 422 |

TABLE 2-continued

| COMPOUND NO. | NMR | MS [M + 1] |
|---|---|---|
| | J = 1.6, 4.7 Hz), 8.89 (1H, d, J = 5.5 Hz), 9.29 (1H, d, J = 1.6 Hz) CDCl3 | |
| 1.111 | 2.02-2.10 (2H, m), 2.15-2.23 (2H, m), 2.47 (3H, s), 3.13-3.19 (2H, m), 3.21-3.27 (2H, m), 3.32 (3H, s), 5.30-5.35 (1H, m), 7.31 (1H, s), 7.37 (2H, d, J = 7.8 Hz), 7.69 (2H, d, J = 8.6 Hz), 7.99 (1H, dd, J = 1.6, 4.7 Hz), 8.86 (1H, d, J = 4.7 Hz), 9.27 (1H, s) CDCl3 | 442 |
| 1.112 | 1.99-2.07 (2H, m), 2.16-2.23 (2H, m), 3.52 (3H, s), 3.63-3.98 (4H, m), 5.53-5.59 (1H, m), 7.12-7.15 (2H, m), 7.20-7.25 (1H, m), 7.36-7.41 (3H, m), 8.08 (1H, dd, J = 1.6, 5.5 Hz), 8.91 (1H, d, J = 4.7 Hz), 9.30 (1H, d, J = 1.6 Hz) CDCl3 | 408 |
| 1.201 | 1.45 (9H, s), 2.05-2.13 (2H, m), 2.22-2.29 (2H, m), 2.36-2.40 (4H, m), 3.22-3.28 (2H, m), 3.41-3.50 (11H, m), 5.45-5.51 (1H, m), 6.94 (2H, d, J = 8.6 Hz), 7.22 (2H, d, J = 8.6 Hz), 7.34 (1H, s), 8.09-8.10 (1H, m), 8.90 (1H, d, J = 4.7 Hz), 9.29 (1H, d, J = 1.6 Hz) CDCl3 | 562 |
| 1.202 | 2.05-2.13 (2H, m), 2.22-2.29 (2H, m), 2.37-2.45 (4H, brs), 2.87-2.90 (4H, m), 3.21-3.27 (2H, m), 3.43-3.49 (7H, m), 5.45-5.50 (1H, m), 6.94 (2H, d, J = 8.6 Hz), 7.23 (2H, d, J = 8.6 Hz), 7.34 (1H, s), 8.09-8.11 (1H, m), 8.96 (1H, d, J = 4.7 Hz), 9.29 (1H, d, J = 1.6 Hz) CDCl3 | 462 |
| 1.203 | 2.05-2.13 (2H, m), 2.22-2.59 (13H, m), 3.21-3.27 (2H, m), 3.43-3.49 (7H, m), 5.45-5.50 (1H, m), 6.94 (2H, d, J = 8.6 Hz), 7.23 (2H, d, J = 8.6 Hz), 7.34 (1H, s), 8.09-8.11 (1H, m), 8.90 (1H, d, J = 5.5 Hz), 9.29 (1H, d, J = 1.6 Hz), CDCl3 | 476 |
| 1.204 | 1.76-1.85 (2H, m), 2.09-2.16 (2H, m), 2.81-2.88 (2H, m), 3.12-3.18 (2H, m), 3.48 (3H, s), 5.31-5.37 (1H, m), 6.83 (1H, s), 7.87 (1H, dd, J = 4.7, 6.3 Hz), 8.53 (1H, d, J = 5.5 Hz), 8.56 (1H, d, J = 3.1 Hz) CDCl3 | 305 |
| 1.205 | 2.05-2.13 (2H, m), 2.23-2.30 (2H, m), 3.23-3.29 (2H, m), 3.46-3.52 (5H, m), 5.45-5.51 (1H, m), 6.90 (1H, t, J = 7.8 Hz), 7.00 (2H, d, J = 7.8 Hz), 7.30 (2H, dd, J = 7.0, 8.6 Hz), 7.35 (1H, s), 8.09-8.11 (1H, m), 8.90 (1H, d, J = 5.5 Hz), 9.29 (1H, s) CDCl3 | 364 |
| 1.206 | 2.06-2.14 (2H, m), 2.24-2.31 (2H, m), 2.35 (3H, s), 2.92-2.98 (2H, m), 3.13-3.19 (2H, m), 3.52 (3H, s), 5.43-5.49 (1H, m), 7.02 (1H, ddd, J = 1.6, 7.0, 7.0 Hz), 7.06-7.09 (1H, m), 7.17-7.23 (2H, m), 7.34 (1H, s), 8.10-8.12 (1H, m), 8.90 (1H, d, J = 4.7 Hz), 9.29 (1H, d, J = 1.6 Hz) CDCl3 | 378 |
| 1.207 | 2.05-2.13 (2H, m), 2.23-2.30 (2H, m), 3.32-3.38 (2H, m), 3.49 (3H, s), 3.56-3.62 (2H, m), 5.45-5.51 (1H, m), 6.85 (1H, s), 7.06 (2H, d, J = 8.6 Hz), 7.48 (1H, dd, J = 1.6, 4.7 Hz), 7.61 (2H, d, J = 8.6 Hz), 7.88 (1H, dd, J = 4.7, 6.3 Hz), 8.54 (1H, d, J = 4.7 Hz), 8.58 (1H, d, J = 3.1 Hz), 8.61 (2H, dd, J = 1.6, 4.7 Hz) CDCl3 | 458 |
| 1.208 | 2.04-2.14 (2H, m), 2.22-2.29 (2H, m), 3.03-3.09 (8H, m), 3.12-3.18 (2H, m), 3.33-3.39 (2H, m), 3.49 (3H, s), 5.42-5.48 (1H, m), 6.91-6.97 (4H, m), 7.34 (1H, s), 8.10 (1H, dd, J = 1.6, 5.5 Hz), 8.90 (1H, d, J = 5.5 Hz), 9.29 (1H, d, J = 1.6 Hz) CDCl3 | 448 |
| 1.209 | 2.05-2.13 (2H, m), 2.22-2.29 (2H, m), 2.36 (3H, s), 2.58-2.61 (4H, m), 3.12-3.17 (6H, m), 3.33-3.39 (2H, m), 3.49 (3H, s), 5.42-5.48 (1H, m), 6.91-6.97 (4H, m), 7.34 (1H, s), 8.10 (1H, dd, J = 1.6, 5.5 Hz), 8.90 (1H, d, J = 4.7 Hz), 9.29 (1H, s) CDCl3 | 462 |
| 1.210 | 2.05-2.14 (5H, m), 2.22-2.30 (2H, m), 3.05-3.10 (4H, m), 3.13-3.19 (2H, m), 3.34-3.41 (2H, m), 3.49 (3H, s), 3.61-3.63 (2H, m), 3.76-3.79 (2H, m), 5.43-5.48 (1H,, m), 6.91-6.98 (4H, m), 7.34 (1H, s), 8.09-8.10 (1H, m), 8.90 (1H, d, J = 5.5 Hz), 9.29 (1H, s) CDCl3 | 490 |
| 1.211 | 1.49 (9H, s), 2.05-2.14 (2H, m), 2.22-2.29 (2H, m), 3.02-3.06 (4H, m), 3.13-3.19 (2H, m), 3.34-3.40 (2H, m), 3.49 (3H, s), 3.57-3.60 (4H, m), 5.43-5.48 (1H, m), 6.90-6.97 (4H, m), 7.34 (1H, s), 8.10 (1H, dd, J = 1.6, 4.7 Hz), 8.90 (1H, d, J = 5.5 Hz), 9.29 (1H, d, J = 1.6 Hz) CDCl3 | 548 |
| 1.212 | 2.05-2.13 (5H, m), 2.22-2.29 (2H, m), 2.38-2.44 (4H, m), 3.23-3.29 (2H, m), 3.44-3.51 (9H, m), 3.60-3.62 (2H, m), 5.45-5.51 (1H, m), 6.95 (2H, d, J = 8.6 Hz), 7.22 (2H, d, J = 8.6 Hz), 7.34 (1H, s), 8.10 (1H, dd, J = 1.6, 4.7 Hz), 8.90 (1H, d, J = 5.5 Hz), 9.29 (1H, d, J = 1.6 Hz) CDCl3 | 504 |
| 1.213 | 2.05-2.13 (2H, m), 2.22-2.29 (2H, m), 2.37-2.45 (4H, brs), 2.87-2.90 (4H, m), 3.21-3.27 (2H, m), 3.43-3.49 (7H, m), 5.45-5.50 (1H, m), 6.94 (2H, d, J = 8.6 Hz), 7.23 (2H, d, J = 8.6 Hz), 7.34 (1H, s), 8.09-8.11 (1H, m), 8.96 (1H, d, J = 4.7 Hz), 9.29 (1H, d, J = 1.6 Hz) | 463 |
| 1.214 | 1.40-1.46 (2H, m), 1.54-1.60 (4H, m), 2.05-2.13 (2H, m), 2.22-2.29 (2H, m), 2.33-2.39 (4H, m), 3.21-3.27 (2H, m), | 461 |

TABLE 2-continued

| COMPOUND NO. | NMR | MS [M + 1] |
|---|---|---|
| | 3.41 (2H, s), 3.43-3.49 (5H, m), 5.44-5.50 (1H, m), 6.94 (2H, d, J = 8.6 Hz), 7.23 (2H, d, J = 8.6 Hz), 7.34 (1H, s), 8.10 (1H, d, J = 5.5 Hz), 8.90 (1H, d, J = 5.5 Hz), 9.29 (1H, s) CDCl3 | |
| 1.215 | 1.40-1.45 (2H, m), 1.53-1.60 (4H, m), 2.04-2.12 (2H, m), 2.22-2.29 (2H, m), 2.31-2.40 (4H, m), 3.20-3.27 (2H, m), 3.41 (2H, s), 3.43-3.50 (5H, m), 5.46-5.51 (1H, m), 6.68 (1H, s), 6.93 (2H, d, J = 8.6 Hz), 7.22 (2H, d, J = 8.6 Hz), 7.77-7.78 (2H, m), 8.73-8.74 (2H, m) CDCl3 | 460 |
| 1.216 | 1.39-1.45 (2H, m), 1.54-1.59 (4H, m), 2.03-2.11 (2H, m), 2.20-2.27 (2H, m), 2.34-2.39 (4H, m), 3.19-3.25 (2H, m), 3.41 (2H, s), 3.42-3.49 (5H, m), 5.40-5.46 (1H, m), 6.85 (1H, s), 6.93 (2H, d, J = 8.6 Hz), 7.20 (2H, d, J = 8.6 Hz), 7.88 (1H, dd, J = 5.5, 7.0 Hz), 8.53 (1H, d, J = 4.7 Hz), 8.57 (1H, d, J = 3.1 Hz) CDCl3 | 478 |
| 1.217 | 1.77-1.80 (4H, m), 2.05-2.13 (2H, m), 2.22-2.29 (2H, m), 2.47-2.52 (4H, m), 3.21-3.27 (2H, m), 3.44-3.50 (5H, m), 3.55 (2H, s), 5.44-5.50 (1H, m), 6.94 (2H, d, J = 8.6 Hz), 7.25 (2H, d, J = 8.6 Hz), 7.34 (1H, s), 8.10 (1H, dd, J = 1.6, 5.5 Hz), 8.90 (1H, d, J = 5.5 Hz), 9.29 (1H, d, J = 1.6 Hz) CDCl3 | 447 |
| 1.218 | 1.94-2.10 (4H, m), 2.20-2.27 (2H, m), 2.43 (2H, dd, J = 7.8, 7.8 Hz), 3.20-3.28 (4H, m), 3.43-3.49 (5H, m), 4.38 (2H, s), 5.41-5.46 (1H, m), 6.85 (1H, s), 6.93 (2H, d, J = 8.6 Hz), 7.17 (2H, d, J = 8.6 Hz), 7.88 (1H, dd, J = 5.5, 7.0 Hz), 8.53 (1H, d, J = 4.7 Hz), 8.57 (1H, d, J = 3.1 Hz) CDCl3 | 478 |
| 1.219 | 2.06-2.14 (2H, m), 2.23-2.30 (2H, m), 3.23-3.29 (2H, m), 3.46-3.52 (5H, m), 3.86 (2H, brs), 3.93 (4H, brs), 5.46-5.51 (1H, m), 6.98 (2H, d, J = 8.6 Hz), 7.18 (4H, brs), 7.33-7.35 (3H, m), 8.09-8.11 (1H, m), 8.90 (1H, d, J = 5.5 Hz), 9.30 (1H, d, J = 1.6 Hz) CDCl3 | 495 |
| 1.220 | 2.05-2.13 (2H, m), 2.23-2.29 (8H, m), 3.22-3.27 (2H, m), 3.35 (2H, s), 3.44-3.50 (5H, m), 5.44-5.50 (1H, m), 6.95 (2H, d, J = 8.6 Hz), 7.22 (2H, d, J = 8.6 Hz), 7.34 (1H, s), 8.10 (1H, dd, J = 1.6, 5.5 Hz), 8.90 (1H, d, J = 4.7 Hz), 9.29 (1H, s) CDCl3 | 421 |
| 1.221 | 2.05-2.13 (2H, m), 2.23-2.30 (2H, m), 2.43-2.47 (4H, m), 3.23-3.29 (2H, m), 3.47-3.52 (7H, m), 3.70-3.73 (4H, m), 5.45-5.51 (1H, m), 6.85-6.90 (2H, m), 6.98 (1H, brs), 7.24 (1H, dd, J = 7.8, 7.8 Hz), 7.35 (1H, s), 8.10 (1H, dd, J = 1.6, 5.5 Hz), 8.90 (1H, d, J = 4.7 Hz), 9.30 (1H, d, J = 1.6 Hz) CDCl3 | 463 |
| 1.222 | 2.05-2.13 (2H, m), 2.23-2.58 (13H, m), 3.23-3.29 (2H, m), 3.46-3.52 (7H, m), 5.45-5.50 (1H, m), 6.85-6.89 (2H, m), 6.98 (1H, brs), 7.23 (1H, dd, J = 7.8, 7.8 Hz), 7.35 (1H, s), 8.09-8.11 (1H, m), 8.90 (1H, d, J = 4.7 Hz), 9.30 (1H, d, J = 1.6 Hz) CDCl3 | 476 |
| 1.223 | 1.40-1.47 (2H, m), 1.55-1.61 (4H, m), 2.05-2.13 (2H, m), 2.22-2.29 (2H, m), 2.34-2.41 (4H, brs), 3.23-3.29 (2H, m), 3.44 (2H, s), 3.46-3.52 (5H, m), 5.44-5.50 (1H, m), 6.84-6.88 (2H, m), 6.98 (1H, s), 7.22 (1H, dd, J = 7.8, 7.8 Hz), 7.34 (1H, s), 8.10 (1H, dd, J = 1.6, 5.5 Hz), 8.90 (1H, d, J = 4.7 Hz), 9.29 (1H, d, J = 1.6 Hz) CDCl3 | 461 |
| 1.224 | 2.07-2.15 (2H, m), 2.24-2.31 (2H, m), 3.28-3.34 (2H, m), 3.49-3.55 (5H, m), 5.48-5.53 (1H, m), 7.20 (1H, dd, J = 4.7, 8.6 Hz), 7.25-7.28 (1H, m), 7.35 (1H, s), 8.09 (1H, dd, J = 1.6, 4.7 Hz), 8.14 (1H, dd, J = 1.6, 4.7 Hz), 8.38 (1H, d, J = 3.1 Hz), 8.90 (1H, d, J = 4.7 Hz), 9.30 (1H, d, J = 1.6 Hz) CDCl3 | 365 |
| 1.225 | 2.06-2.14 (2H, m), 2.23-2.30 (2H, m), 3.19-3.25 (2H, m), 3.42-3.49 (5H, m), 4.18 (2H, s), 4.21 (2H, s), 5.45-5.50 (1H, m), 6.87 (1H, dd, J = 2.4, 8.6 Hz), 6.91 (1H, d, J = 1.6 Hz), 7.17 (1H, d, J = 7.8 Hz), 7.34 (1H, s), 8.10 (1H, dd, J = 1.6, 5.5 Hz), 8.90 (1H, d, J = 5.5 Hz), 9.29 (1H, d, J = 1.6 Hz) CDCl3 | 405 |
| 1.226 | 2.05-2.13 (2H, m), 2.22-2.29 (2H, m), 2.59 (3H, s), 3.17-3.23 (2H, m), 3.41-3.47 (2H, m), 3.49 (3H, s), 3.85 (2H, s), 3.88 (2H, s), 5.44-5.49 (1H, m), 6.82-6.86 (2H, m), 7.11 (1H, d, J = 7.8 Hz), 7.34 (1H, s), 8.09-8.10 (1H, m), 8.90 (1H, d, J = 4.7 Hz), 9.29 (1H, d, J = 1.6 Hz) CDCl3 | 419 |
| 1.227 | 2.03-2.11 (2H, m), 2.21-2.28 (2H, m), 3.15-3.21 (2H, m), 3.39-3.45 (2H, m), 3.48 (3H, s), 3.88 (2H, s), 3.90-3.91 (4H, m), 5.43-5.48 (1H, m), 6.82-6.84 (2H, m), 7.08-7.10 (1H, m), 7.27-7.30 (1H, m), 7.33-7.38 (3H, m), 7.40-7.43 (2H, m), 8.08-8.10 (1H, m), 8.89 (1H, d, J = 5.5 Hz), 9.29 (1H, d, J = 1.6 Hz) CDCl3 | 495 |
| 1.228 | 2.14-2.22 (2H, m), 2.25-2.32 (2H, m), 3.47-3.54 (5H, m), 3.60-3.67 (2H, m), 5.57-5.62 (1H, m), 6.03 (1H, d, J = 4.7 Hz), 7.36 (1H, s), 7.80 (1H, d, J = 4.7 Hz), 8.05 (1H, dd, J = 1.6, 5.5 Hz), 8.90 (1H, d, J = 5.5 Hz), 9.30 (1H, dd, J = 1.6 Hz) CDCl3 | 415 |
| 1.229 | 2.07-2.15 (2H, m), 2.24-2.31 (2H, m), 3.32-3.38 (2H, m), 3.49 (3H, s), 3.52-3.58 (2H, m), 5.46-5.52 (1H, m), 6.85 (1H, s), 7.85 (1H, dd, J = 4.7, 6.3 Hz), 8.44 (2H, s), 8.54 (1H, d, J = 5.5 Hz), 8.58 (1H, d, J = 3.1 Hz), 8.73 (1H, s) CDCl3 | 383 |

TABLE 2-continued

| COMPOUND NO. | NMR | MS [M + 1] |
|---|---|---|
| 1.230 | 2.06-2.14 (2H, m), 2.17 (3H, s), 2.23-2.31 (2H, m), 3.22-3.29 (2H, m), 3.43-3.50 (5H, m), 4.73-4.78 (4H, m), 5.46-5.51 (1H, m), 6.88 (1H, dd, J = 1.6, 14.1 Hz), 6.95 (1H, ddd, J = 1.6, 8.6, 8.6 Hz), 7.19 (1H, dd, J = 8.6, 16.4 Hz), 7.35 (1H, s), 8.09 (1H, dd, J = 1.6, 4.7 Hz), 8.90 (1H, d, J = 5.5 Hz), 9.29 (1H, s) CDCl3 | 447 |
| 1.231 | 1.39-1.44 (2H, m), 1.53-1.58 (4H, m), 2.33-2.38 (4H, m), 2.43-2.48 (2H, m), 3.40 (2H, s), 3.43 (3H, s), 3.49-3.62 (3H, m), 3.85 (1H, dd, J = 4.7, 11.7 Hz), 5.87-5.91 (1H, m), 6.57 (2H, d, J = 8.6 Hz), 7.20 (2H, d, J = 8.6 Hz), 7.36 (1H, s), 8.14-8.15 (1H, m), 8.92 (1H, d, J = 5.5 Hz), 9.30 (1H, d, J = 1.6 Hz) CDCl3 | 447 |
| 1.232 | 1.39-1.44 (2H, m), 1.53-1.66 (6H, m), 1.91-1.97 (2H, m), 1.98-2.08 (1H, m), 2.32-2.38 (4H, m), 2.76 (2H, ddd, J = 2.4, 11.7, 11.7 Hz), 3.40 (2H, s), 3.49 (3H, s), 3.75 (2H, ddd, J = 2.4, 2.4, 12.5 Hz), 4.45 (2H, d, J = 6.3 Hz), 6.68 (1H, s), 6.91 (2H, d, J = 8.6 Hz), 7.20 (2H, d, J = 8.6 Hz), 7.79 (2H, dd, J = 1.6, 4.7 Hz), 8.73 (2H, dd, J = 1.6, 4.7 Hz) CDCl3 | 474 |
| 1.233 | 1.39-1.45 (2H, m), 1.53-1.66 (6H, m), 1.92-1.97 (2H, m), 2.00-2.09 (1H, m), 2.32-2.39 (4H, m), 2.76 (2H, ddd, J = 2.4, 12.5, 12.5 Hz), 3.40 (2H, s), 3.50 (3H, s), 3.75 (2H, ddd, J = 2.4, 2.4, 12.5 Hz), 4.45 (2H, d, J = 6.3 Hz), 6.91 (2H, d, J = 8.6 Hz), 7.20 (2H, d, J = 8.6 Hz), 7.34 (1H, s), 8.14 (1H, dd, J = 1.6, 5.5 Hz), 8.90 (1H, d, J = 5.5 Hz), 9.29 (1H, d, J = 1.6 Hz) CDCl3 | 475 |
| 1.234 | 1.39-1.45 (2H, m), 1.53-1.66 (6H, m), 1.91-1.97 (2H, m), 1.98-2.07 (1H, m), 2.32-2.38 (4H, m), 2.76 (2H, ddd, J = 2.4, 12.5, 12.5 Hz), 3.40 (2H, s), 3.49 (3H, s), 3.74 (2H, ddd, J = 2.4, 2.4, 12.5 Hz), 4.41 (2H, d, J = 6.3 Hz), 6.86 (1H, s), 6.91 (2H, d, J = 8.6 Hz), 7.20 (2H, d, J = 8.6 Hz), 7.94 (1H, dd, J = 5.5, 7.0 Hz), 8.54 (1H, d, J = 4.7 Hz), 8.57 (1H, d, J = 3.1 Hz) CDCl3 | 492 |
| 1.301 | 2.04-2.12 (2H, m), 2.24-2.30 (2H, m), 2.50-2.53 (4H, m), 2.98-3.04 (2H, m), 3.24-3.29 (2H, m), 3.53 (3H, s), 3.59 (2H, brs), 3.68-3.71 (4H, m), 5.42-5.48 (1H, m), 7.09 (1H, dd, J = 7.0, 8.6 Hz), 7.15 (1H, d, J = 7.8 Hz), 7.27 (1H, ddd, J = 1.6, 7.8, 8.6 Hz), 7.35 (1H, s), 7.43 (1H, dd, J = 1.6, 7.8 Hz), 8.11-8.12 (1H, m), 8.91 (1H, d, J = 4.7 Hz), 9.30 (1H, d, J = 1.6 Hz) CDCl3 | 463 |
| 1.302 | 2.03-2.11 (2H, m), 2.17-2.78 (13H, m), 2.97-3.03 (2H, m), 3.22-3.28 (2H, m), 3.53 (3H, s), 3.60 (2H, brs), 5.42-5.48 (1H, m), 7.09 (1H, dd, J = 7.0, 8.6 Hz), 7.14 (1H, dd, J = 0.8, 7.8 Hz), 7.27 (1H, ddd, J = 1.6, 7.8, 8.6 Hz), 7.34 (1H, s), 7.42 (1H, dd, J = 1.6, 7.0 Hz), 8.12 (1H, dd, J = 1.6, 4.7 Hz), 8.91 (1H, d, J = 4.7 Hz), 9.30 (1H, d, J = 1.6 Hz) CDCl3 | 476 |
| 1.303 | 1.40-1.63 (6H, m), 2.04-2.12 (2H, m), 2.24-2.30 (2H, m), 2.38-2.51 (4H, m), 2.97-3.03 (2H, m), 3.23-3.30 (2H, m), 3.50-3.58 (5H, m), 5.42-5.48 (1H, m), 7.07-7.16 (2H, m), 7.24-7.28 (1H, m), 7.34 (1H, s), 7.41-7.47 (1H, m), 8.11-8.12 (1H, m), 8.91 (1H, d, J = 5.5 Hz), 9.30 (1H, s) CDCl3 | 461 |
| 1.304 | 2.05-2.13 (2H, m), 2.25-2.32 (2H, m), 2.99-3.05 (2H, m), 3.28-3.34 (2H, m), 3.52 (3H, s), 4.01 (6H, brs), 5.39-5.46 (1H, m), 7.11-7.16 (2H, m), 7.20 (4H, brs), 7.26-7.31 (1H, m), 7.34 (1H, s), 7.53-7.57 (1H, m), 8.09-8.11 (1H, m), 8.89-8.11 (1H, m), 8.89 (1H, d, J = 4.7 Hz), 9.29 (1H, d, J = 1.6 Hz) CDCl3 | 495 |
| 1.305 | 2.05-2.13 (2H, m), 2.25-2.31 (8H, m), 2.96-3.02 (2H, m), 3.21-3.27 (2H, m), 3.51-3.53 (5H, m), 5.42-5.48 (1H, m), 7.08-7.14 (2H, m), 7.24-7.28 (1H, m), 7.34 (1H, s), 7.44 (1H, dd, J = 1.6, 7.8 Hz), 8.11 (1H, dd, J = 1.6, 5.5 Hz), 8.90 (1H, d, J = 4.7 Hz), 9.29 (1H, s) CDCl3 | 421 |
| 1.401 | 2.05-2.14 (2H, m), 2.23-2.30 (2H, m), 3.16-3.22 (2H, m), 3.35-3.41 (2H, m), 3.49 (3H, s), 5.29 (2H, s), 5.45-5.50 (1H, m), 6.73-6.76 (2H, m), 6.91 (1H, dd, J = 2.4, 8.6 Hz), 7.34-7.35 (2H, m), 8.09 (1H, dd, J = 1.6, 4.7 Hz), 8.90 (1H, d, J = 5.5 Hz), 9.30 (1H, d, J = 1.6 Hz) CDCl3 | 435 |
| 1.501 | 1.11-1.22 (2H, m), 1.36-1.49 (3H, m), 1.61-1.71 (2H, m), 1.92-2.00 (2H, m), 2.10-2.17 (2H, m), 2.40-2.47 (4H, m), 2.60 (2H, ddd, J = 2.4, 11.7, 11.7 Hz), 2.66-2.74 (2H, m), 3.07 (2H, ddd, J = 2.4, 3.1, 11.7 Hz), 3.48 (3H, s), 5.29-5.35 (1H, m), 7.32 (1H, s), 8.08 (1H, dd, J = 1.6, 4.7 Hz), 8.89 (1H, d, J = 5.5 Hz), 9.28 (1H, d, J = 1.6 Hz) CDCl3 | 399 |
| 1.502 | 1.26-1.36 (3H, m), 1.44-1.50 (2H, m), 1.62-1.70 (2H, m), 1.91-2.00 (4H, m), 2.09-2.17 (2H, m), 2.38-2.46 (4H, m), 2.65-2.73 (2H, m), 2.86-2.92 (2H, m), 3.47-3.51 (5H, m), 5.29-5.34 (1H, m), 7.24-7.32 (6H, m), 8.08 (1H, dd, J = 1.6, 5.5 Hz), 8.88 (1H, d, J = 4.7 Hz), 9.28 (1H, d, J = 1.6 Hz) CDCl3 | 489 |
| 1.503 | 1.26-1.38 (3H, m), 1.46-1.51 (2H, m), 1.63-1.73 (2H, m), 1.90-2.00 (4H, m), 2.10-2.17 (2H, m), 2.28 (3H, s), 2.39-2.47 (4H, m), 2.66-2.73 (2H, m), 2.83-2.88 (2H, m), 3.48 (3H, s), 5.29-5.35 (1H, m), 7.32 (1H, s), 8.08 (1H, dd, J = 1.6, | 413 |

TABLE 2-continued

| COMPOUND NO. | NMR | MS [M + 1] |
|---|---|---|
| | 4.7 Hz), 8.89 (1H, d, J = 4.7 Hz), 9.28 (1H, d, J = 1.6 Hz) CDCl3 | |
| 1.504 | 1.91-1.99 (2H, m), 2.09-2.16 (2H, m), 2.42-2.48 (2H, m), 2.70-2.75 (2H, m), 3.47 (3H, s), 3.57 (2H, s), 5.29-5.35 (1H, m), 7.27-7.35 (6H, m), 8.08 (1H, dd, J = 1.6, 5.5 Hz), 8.89 (1H, d, J = 5.5 Hz), 9.28 (1H, d, J = 1.6 Hz) CDCl3 | 378 |
| 1.505 | 1.61-1.69 (1H, m), 1.79-1.84 (2H, m), 1.91-2.04 (5H, m), 2.11-2.18 (2H, m), 2.28-2.39 (4H, m), 2.55-2.61 (2H, m), 2.80-2.86 (2H, m), 2.92-2.97 (2H, m), 3.48 (3H, s), 5.27-5.34 (1H, m), 7.32 (1H, s), 8.08-8.10 (1H, m), 8.89-8.90 (1H, m), 9.28 (1H, s) CDCl3 | 385 |
| 1.601 | 1.89-2.24 (4H, m), 2.26 (6H, s), 3.45 (2H, s), 3.50 (3H, s), 3.51-4.07 (4H, m), 5.53-5.59 (1H, m), 7.35 (1H, s), 7.37-7.42 (4H, m), 8.05 (1H, dd, J = 1.6, 4.7 Hz), 8.89 (1H, d, J = 5.5 Hz), 9.29 (1H, d, J = 1.6 Hz) CDCl3 | 449 |
| 1.701 | 1.91-2.36 (6H, m), 3.37 (3H, s), 3.52-3.71 (4H, m), 5.48-5.54 (1H, m), 6.72 (2H, d, J = 8.6 Hz), 7.32 (1H, s), 7.51 (2H, d, J = 8.6 Hz), 7.98 (1H, dd, J = 1.6, 5.5 Hz), 8.88 (1H, d, J = 4.7 Hz), 9.28 (1H, d, J = 1.6 Hz) CDCl3 | 403 |
| 1.801 | 1.01 (3H, dd, J = 7.0, 7.0 Hz), 1.16-1.92 (8H, m), 2.14-2.22 (0.45H, m), 2.28-2.33 (0.55H, m), 3.48 (1.7H, s), 3.51 (1.3H, s), 4.85-4.92 (0.55H, m), 5.43-5.45 (0.45H, m), 7.31 (1H, d, J = 1.6 Hz), 8.09-8.12 (1H, m), 8.87-8.90 (1H, m), 9.28 (1H, s) CDCl3 | 301 |
| 1.802 | 1.39-1.56 (3H, m), 1.58-1.65 (1H, m), 1.66-1.75 (2H, m), 1.78-1.86 (2H, m), 2.01-2.08 (2H, m), 3.47 (3H, s), 5.26-5.32 (1H, m), 7.31 (1H, s), 8.10 (1H, dd, J = 1.2, 5.1 Hz), 8.89 (1H, d, J = 5.1 Hz), 9.28 (1H, d, J = 1.6 Hz) CDCl3 | 287 |
| 1.803 | 0.92 (3H, t, J = 7.0 Hz), 1.12-2.00 (10H, m), 2.19-2.30 (1H, m), 3.47 (1.4H, s), 3.50 (1.6H, s), 5.00-5.06 (0.45H, m), 5.57-5.59 (0.55H, m), 7.31-7.32 (1H, brs), 8.09-8.13 (1H, m), 8.87-8.90 (1H, m), 9.28-9.29 (1H, brs) CDCl3 | 315 |
| 1.804 | 1.67-1.77 (2H, m), 1.79-1.89 (2H, m), 1.91-1.99 (2H, m), 2.02-2.11 (2H, m), 3.44 (3H, s), 5.61-5.65 (1H, m), 7.31 (1H, s), 8.15 (1H, dd, J = 1.2, 5.1 Hz), 8.88 (1H, d, J = 5.1 Hz), 9.28 (1H, d, J = 1.6 Hz) CDCl3 | 273 |
| 1.805 | 3.47 (3H, s), 4.39-4.42 (2H, m), 4.90-4.92 (2H, m), 6.70 (1H, s), 6.95 (2H, d, J = 7.8 Hz), 7.00 (1H, dd, J = 7.0, 7.0 Hz), 7.32 (2H, dd, J = 7.0, 8.6 Hz), 7.78 (2H, dd, J = 1.6, 4.7 Hz), 8.73 (2H, dd, J = 1.6, 4.7 Hz) CDCl3 | 324 |
| 1.806 | 3.35-3.38 (5H, m), 4.75 (2H, t, J = 6.3 Hz), 6.66 (1H, s), 7.24-7.32 (3H, m), 7.42-7.45 (2H, m), 7.69 (2H, dd, J = 1.6, 4.7 Hz), 8.70 (2H, dd, J = 1.6, 4.7 Hz) CDCl3 | 340 |
| 1.807 | 3.45 (3H, s), 3.66 (2H, t, J = 5.5 Hz), 4.03 (1H, brs), 4.77 (2H, t, J = 5.5 Hz), 6.67 (2H, d, J = 7.8 Hz), 6.69 (1H, s), 6.76 (1H, dd, J = 7.0, 7.0 Hz), 7.18-7.22 (2H, m), 7.76 (2H, dd, J = 1.6, 4.7 Hz), 8.73 (2H, dd, J = 1.6, 4.7 Hz) CDCl3 | 323 |
| 1.808 | 1.20 (3H, t, J = 7.0 Hz), 2.28 (3H, s), 3.42-3.47 (5H, m), 3.77 (2H, t, J = 6.3 Hz), 4.68 (2H, t, J = 6.3 Hz), 6.54-6.60 (3H, m), 6.84 (1H, s), 7.10 (1H, dd, J = 7.8, 7.8 Hz), 7.83 (1H, dd, J = 4.7, 6.3 Hz), 8.50 (1H, d, J = 4.7 Hz), 8.56 (1H, d, J = 3.1 Hz) CDCl3 | 383 |
| 1.809 | 1.20 (3H, t, J = 7.0 Hz), 2.29 (3H, s), 3.42-3.47 (5H, m), 3.78 (2H, t, J = 6.3 Hz), 4.72 (2H, t, J = 6.3 Hz), 6.55-6.61 (3H, m), 7.12 (1H, dd, J = 7.8, 7.8 Hz), 7.33 (1H, s), 8.01 (1H, dd, J = 1.6, 4.7 Hz), 8.84 (1H, d, J = 5.5 Hz), 9.27 (1H, d, J = 1.6 Hz) CDCl3 | 366 |
| 1.810 | 2.23 (2H, tt, J = 6.3, 7.8 Hz), 2.85 (2H, t, J = 7.8 Hz), 3.45 (3H, s), 4.59 (2H, t, J = 6.3 Hz), 7.25 (1H, dd, J = 4.7, 7.8 Hz), 7.34 (1H, s), 7.55 (1H, ddd, J = 1.6, 2.4, 7.8 Hz), 8.05 (1H, dd, J = 1.6, 5.5 Hz), 8.50 (1H, dd, J = 1.6, 4.7 Hz), 8.53 (1H, d, J = 1.6 Hz), 8.88 (1H, d, J = 5.5 Hz), 9.28 (1H, d, J = 1.6 Hz) CDCl3 | 324 |
| 1.901 | 1.66 (1H, t, J = 6.3 Hz), 1.70-1.75 (4H, m), 2.06-2.10 (2H, m), 2.38-2.43 (2H, m), 2.62-2.69 (1H, m), 3.48 (3H, s), 4.70 (2H, d, J = 5.5 Hz), 5.23-5.30 (1H, m), 7.27 (2H, d, J = 8.6 Hz), 7.32-7.36 (3H, m), 8.12 (1H, dd, J = 1.6, 4.7 Hz), 8.91 (1H, d, J = 5.5 Hz), 9.29 (1H, d, J = 1.6 Hz) CDCl3 | 393 |
| 1.902 | 1.64 (1H, t, J = 6.3 Hz), 1.83-1.90 (6H, m), 2.30-2.35 (2H, m), 2.66-2.74 (1H, m), 3.57 (3H, s), 4.69 (2H, d, J = 6.3 Hz), 5.63-5.66 (1H, m), 7.26 (2H, d, J = 8.6 Hz), 7.34-7.36 (3H, m), 8.12-8.13 (1H, m), 8.89 (1H, d, J = 4.7 Hz), 9.29 (1H, d, J = 1.6 Hz) CDCl3 | 393 |
| 1.903 | 1.66-1.77 (4H, m), 2.04-2.12 (2H, m), 2.27-2.69 (14H, m), 3.48 (3H, s), 3.50 (2H, s), 5.22-5.30 (1H, m), 7.20 (2H, d, J = 8.6 Hz), 7.27 (2H, d, J = 8.6 Hz), 7.33 (1H, s), 8.11-8.13 (1H, m), 8.91 (1H, d, J = 4.7 Hz), 9.29 (1H, d, J = 1.6 Hz) CDCl3 | 475 |
| 1.904 | 1.82-1.89 (6H, m), 2.23-2.75 (14H, m), 3.50 (2H, s), 3.56 (3H, s), 5.62-5.65 (1H, m), 7.19 (2H, d, J = 8.6 Hz), 7.28 (2H, d, J = 8.6 Hz), | 475 |

TABLE 2-continued

| COMPOUND NO. | NMR | MS [M + 1] |
|---|---|---|
| | 7.33 (1H, s), 8.12-8.13 (1H, m), 8.89 (1H, d, J = 5.5 Hz), 9.29 (1H, d, J = 1.6 Hz) CDCl3 | |
| 2.001 | 0.91 (3H, t, J = 6.9 Hz), 1.25-1.42 (6H, m), 1.58-1.72 (2H, m), 2.69 (2H, t, J = 7.5 Hz), 3.67 (3H, s), 7.12-7.17 (2H, m), 7.23-7.30 (2H, m), 7.39 (1H, s), 7.67 (1H, dd, J = 1.5 Hz, 5.4 Hz), 8.73 (1H, d, J = 5.1 Hz), 9.23 (1H, d, J = 1.5 Hz) (CDCl3) | 365 |
| 2.002 | 3.12 (2H, d, J = 6.7 Hz), 3.27 (3H, s), 4.73 (2H, d, J = 6.7 Hz), 6.88 (1H, s), 7.20-7.27 (1H, m), 7.31-7.37 (4H, m), 7.99 (2H, dd, J = 1.1, 4.6 Hz), 8.71 (2H, dd, J = 1.0, 4.7 Hz) (DMSO) | 308 |
| 2.003 | 0.92 (3H, t, J = 6.9 Hz), 1.30-1.40 (4H, m), 1.42-1.55 (2H, m), 1.80-1.91 (2H, m), 3.47 (3H, s), 4.54 (2H, t, J = 6.9 Hz), 6.67 (1H, s), 7.80 (2H, dd, J = 1.5, 4.5 Hz), 8.72 (2H, dd, J = 1.5, 4.8 Hz) (CDCl3) | 288 |
| 2.101 | 1.87-1.92 (2H, m), 2.03-2.12 (4H, m), 2.21 (2H, ddd, J = 3.9, 3.9, 15.7 Hz), 3.51 (3H, s), 3.59-3.63 (2H, m), 5.55 (1H, t, J = 5.5 Hz), 7.32 (1H, s), 8.07 (1H, dd, J = 1.6, 4.7 Hz), 8.88 (1H, d, J = 5.5 Hz), 9.28 (1H, d, J = 1.6 Hz) CDCl3 | 314 |
| 2.102 | 1.93 (2H, d, J = 14.9 Hz), 2.16-2.25 (4H, m), 2.44 (2H, ddd, J = 3.9, 3.9, 15.7 Hz), 3.55 (3H, s), 4.21-4.24 (2H, m), 5.47 (1H, t, J = 4.7 Hz), 6.72-6.77 (2H, m), 6.96-7.03 (2H, m), 7.33 (1H, s), 8.00 (1H, dd, J = 1.6, 5.5 Hz), 8.82 (1H, d, J = 5.5 Hz), 9.27 (1H, d, J = 1.6 Hz) CDCl3 | 408 |
| 2.201 | 1.93-2.17 (4H, m), 3.38-3.62 (5H, m), 4.32-4.90 (3H, m), 7.03-7.25 (4H, m), 7.33-7.41 (1H, m), 8.15-8.31 (1H, m), 8.29 (1H, dd, J = 5.5, 1.2 Hz), 8.59-8.99 (1H, m), 9.26-9.32 (1H, m) (DMSO-d6) | 408 |
| 2.202 | 1.98-2.17 (4H, m), 3.03-3.10 (1H, m), 3.35 (3H, s), 3.42-3.47 (1H, m), 4.12-4.17 (1H, m), 4.40 (1H, dd, J = 10.9, 7.8 Hz), 4.64 (1H, dd, J = 10.7, 4.1 Hz), 6.70-6.74 (2H, m), 6.99 (2H, t, J = 8.8 Hz), 7.03 (1H, s), 8.18 (1H, dd, J = 5.3, 1.4 Hz), 9.01 (1H, d, J = 5.5 Hz), 9.31 (1H, d, J = 1.2 Hz) (DMSO-d6) | 382 |
| 2.203 | 1.97-2.15 (4H, m), 3.01-3.08 (1H, m), 3.40-3.46 (1H, m), 4.08-4.15 (1H, m), 4.27 (1H, dd, J = 10.9, 8.2 Hz), 4.62 (1H, dd, J = 10.9, 3.9 Hz), 6.61 (1H, s), 6.71 (2H, dd, J = 9.2, 4.5 Hz), 6.88 (2H, t, J = 9.0 Hz), 7.92 (1H, dd, J = 6.6, 5.1 Hz), 8.59 (1H, dd, J = 4.9, 1.0 Hz), 8.75 (1H, d, J = 3.1 Hz) (DMSO-d6) | 399 |
| 2.204 | 1.99-2.15 (4H, m), 3.03-3.10 (1H, m), 3.44 (1H, t, J = 8.4 Hz), 4.12-4.17 (1H, m), 4.40 (1H, dd, J = 10.7, 7.6 Hz), 4.64 (1H, dd, J = 10.7, 4.1 Hz), 6.70-6.74 (2H, m), 6.99 (2H, t, J = 8.8 Hz), 7.03 (1H, s), 8.18 (1H, dd, J = 5.1, 1.6 Hz), 9.01 (1H, d, J = 5.1 Hz), 9.31 (1H, d, J = 1.6 Hz) (DMSO-d6) | 382 |
| 2.205 | 1.98-2.15 (4H, m), 3.01-3.07 (1H, m), 3.40-3.45 (1H, m), 4.12 (1H, td, J = 7.0, 2.7 Hz), 4.27 (1H, dd, J = 10.9, 8.2 Hz), 4.62 (1H, dd, J = 10.9, 3.9 Hz), 6.61 (1H, d, J = 1.2 Hz), 6.69-6.73 (2H, m), 6.88 (2H, t, J = 8.8 Hz), 7.92 (1H, dd, J = 6.8, 4.9 Hz), 8.59 (1H, dd, J = 4.9, 1.0 Hz), 8.75 (1H, d, J = 3.1 Hz) (DMSO-d6) | 399 |
| 2.206 | 1.82-1.91 (1H, m), 2.12-2.21 (1H, m), 2.78-2.90 (1H, m), 3.14 (1H, dd, J = 9.4, 6.2 Hz), 3.18-3.25 (1H, m), 3.27-3.31 (1H, m), 3.36 (3H, s), 3.37-3.41 (1H, m), 4.46-4.55 (2H, m), 5.95 (1H, dd, J = 3.1, 1.6 Hz), 6.65 (2H, d, J = 0.8 Hz), 6.76 (1H, dd, J = 5.1, 1.6 Hz), 7.38 (1H, dd, J = 5.5, 3.1 Hz), 8.02 (1H, dd, J = 6.6, 5.1 Hz), 8.58 (1H, dd, J = 4.9, 1.0 Hz), 8.72 (1H, d, J = 3.1 Hz) (DMSO-d6) | 387 |
| 2.207 | 1.84-1.93 (1H, m), 2.14-2.23 (1H, m), 2.81-2.91 (1H, m), 3.15 (1H, dd, J = 9.4, 6.2 Hz), 3.19-3.25 (1H, m), 3.29-3.32 (1H, m), 3.36 (3H, s), 3.40 (1H, dd, J = 9.4, 7.4 Hz), 4.55-4.59 (2H, m), 5.96 (1H, dd, J = 3.1, 1.6 Hz), 6.76 (1H, dd, J = 5.1, 1.6 Hz), 7.05 (1H, s), 7.38 (1H, dd, J = 5.1, 3.1 Hz), 8.27 (1H, dd, J = 5.3, 1.4 Hz), 9.01 (1H, d, J = 5.1 Hz), 9.31 (1H, d, J = 1.6 Hz) (DMOS-d6) | 370 |
| 2.208 | 2.12-2.21 (1H, m), 2.84 (1H, dt, J = 14.0, 6.9 Hz), 3.14 (1H, dd, J = 9.6, 6.0 Hz), 3.17-3.25 (1H, m), 3.28-3.31 (1H, m), 3.36 (3H, s), 3.37-3.41 (2H, m), 4.47-4.55 (2H, m), 5.95 (1H, dd, J = 2.9, 1.4 Hz), 6.65 (1H, d, J = 0.8 Hz), 6.76 (1H, dd, J = 5.1, 1.6 Hz), 7.38 (1H, dd, J = 5.5, 3.1 Hz), 8.02 (1H, dd, J = 6.6, 5.1 Hz), 8.58 (1H, dd, J = 4.9, 1.0 Hz), 8.72 (1H, d, J = 3.5 Hz) (DMSO-d6) | 387 |
| 2.209 | 1.95 (1H, dq, J = 12.3, 7.5 Hz), 2.18-2.27 (1H, m), 2.83-2.94 (1H, m), 3.21 (1H, dd, J = 9.6, 6.4 Hz), 3.25-3.32 (1H, m), 3.37 (3H, s), 3.38-3.42 (1H, m), 3.48 (1H, dd, J = 9.4, 7.4 Hz), 4.56-4.64 (2H, m), 6.54-6.61 (3H, m), 7.05 (1H, s), 7.16 (2H, dd, J = 8.6, 7.4 Hz), 8.26 (1H, dd, J = 5.1, 1.2 Hz), 9.00 (1H, d, J = 5.1 Hz), 9.31 (1H, d, J = 1.2 Hz) (DMSO-d6) | 364 |
| 2.210 | 1.88-1.98 (1H, m), 2.16-2.25 (1H, m), 2.87 (1H, ddd, J = 13.9, 7.2, 7.0 Hz), 3.19 (1H, dd, J = 9.6, 6.4 Hz), 3.24-3.31 (1H, m), 3.36 (3H, s), 3.37-3.40 (1H, m), 3.47 (1H, dd, J = 9.4, 7.4 Hz), 4.50-4.59 (2H, m), 6.55 (2H, d, J = 7.8 Hz), 6.59 (1H, t, J = 7.2 Hz), 6.65 (1H, d, J = 0.8 Hz), 7.16 (2H, dd, J = 8.6, 7.0 Hz), | 381 |

TABLE 2-continued

| COMPOUND NO. | NMR | MS [M + 1] |
|---|---|---|
| | 8.01 (1H, dd, J = 7.0, 5.1 Hz), 8.57 (1H, dd, J = 5.1, 0.8 Hz), 8.72 (1H, d, J = 3.1 Hz) (DMSO-d6) | |
| 2.211 | 1.93 (1H, dq, J = 12.5, 7.5 Hz), 2.17-2.25 (1H, m), 2.87 (1H, dt, J = 14.0, 7.0 Hz), 3.16-3.21 (1H, m), 3.24-3.31 (1H, m), 3.36 (3H, s), 3.37-3.41 (1H, m), 3.47 (1H, dd, J = 9.6, 7.6 Hz), 4.50-4.59 (2H, m), 6.54-6.62 (3H, m), 6.65 (1H, s), 7.16 (2H, dd, J = 8.6, 7.4 Hz), 8.01 (1H, dd, J = 7.0, 5.1 Hz), 8.57 (1H, dd, J = 4.9, 1.0 Hz), 8.72 (1H, d, J = 3.1 Hz) (DMSO-d6) | 381 |
| 2.301 | 3.60 (3H, s), 5.70 (2H, s), 7.33 (1H, s), 7.54-7.72 (4H, m), 7.99 (2H, d, J = 8.4 Hz), 8.68 (1H, d, J = 5.2 Hz), 9.22 (1H, s) CDCl3 | 309 |
| 2.302 | 3.17 (2H, t, J = 6.8 Hz), 3.42 (3H, s), 4.73 (2H, t, J = 6.8 Hz), 7.28 (6H, m), 8.12 (1H, d, J = 5.2 Hz), 8.88 (1H, d, J = 5.2 Hz), 9.27 (1H, s) CDCl3 | 309 |
| 2.303 | 3.50 (3H, s), 5.68 (2H, s), 6.83 (1H, s), 7.51 (1H, dd, J = 5.4, 6.0 Hz), 7.70 (2H, t, J = 8.4 Hz), 7.83 (2H, d, J = 8.4 Hz), 8.34 (1H, d, J = 4.7 Hz), 8.50 (1H, d, J = 3.1 Hz) CDCl3 | 419 |
| 2.304 | 3.59 (3H, s), 5.71 (2H, s), 6.66 (1H, s), 7.53 (2H, d, J = 6.6 Hz), 7.70 (2H, d, J = 10.2 Hz), 7.84 (2H, d, J = 10.2 Hz), 8.61 (2H, d, J = 6.3 Hz) CDCl3 | 401 |
| 2.305 | 3.59 (3H, s), 5.70 (2H, s), 7.33 (1H, s), 7.70 (2H, d, J = 8.4 Hz), 7.70 (1H, d, J = 5.4 Hz), 7.85 (2H, d, J = 8.4 Hz), 8.72 (1H, d, J = 4.8 Hz), 9.22 (1H, s) CDCl3 | 402 |
| 2.401 | 1.27-1.37 (1H, m), 1.65-1.83 (5H, m), 2.73-2.83 (2H, m), 3.15-3.23 (4H, m), 3.28 (3H, s), 4.20 (2H, d, J = 4.7 Hz), 4.79 (2H, t, J = 6.3 Hz), 7.11 (1H, s), 7.44 (2H, d, J = 7.8 Hz), 7.58 (2H, d, J = 7.8 Hz), 8.44 (2H, d, J = 7.0 Hz), 8.95 (2H, d, J = 7.0 Hz), 10.79 (1H, brs) DMSO-d6 | 405 |
| 2.402 | 2.64 (6H, d, J = 5.5 Hz), 3.17 (2H, t, J = 7.0 Hz), 3.28 (3H, s), 4.23 (2H, d, J = 5.5 Hz), 4.79 (2H, t, J = 5.5 Hz), 7.11 (1H, s), 7.45 (2H, d, J = 7.8 Hz), 7.54 (2H, d, J = 7.8 Hz), 8.45 (2H, d, J = 6.3 Hz), 8.95 (2H, d, J = 6.3 Hz), 10.94 (1H, brs) DMSO-d6 | 365 |
| 2.501 | 3.41 (3H, s), 3.97 (2H, t, J = 6.6 Hz), 4.16 (2H, t, J = 6.9 Hz), 4.69 (2H, s), 7.26-7.43 (4H, m), 7.57-7.60 (2H, m), 8.09 (1H, d, J = 5.1 Hz), 8.88 (1H, s), 9.27 (1H, s) CDCl3 | 367 |
| 2.502 | 1.50-1.74 (6H, m), 3.46-4.04 (4H, m), 3.59 (3H, s), 4.69 (1H, s), 6.37 (1H, m), 7.28 (1H, s), 7.29-7.47 (6H, m), 7.98 (2H, d, J = 8.4 Hz), 8.68 (1H, d, J = 5.2 Hz), 9.29 (1H, s) CDCl3 | 409 |

Experiment 1: Inhibitory Activity of the Medicament of the Present Invention Against P-GS1 Phosphorylation by Bovine Cerebral TPK1

A mixture containing 100 mM MES-sodium hydroxide (pH 6.5), 1 mM magnesium acetate, 0.5 mM EGTA, 5 mM, β-mercaptoethanol, 0.02% Tween 20, 10% glycerol, 12 μg/ml P-GS1, 41.7 μM [γ-$^{32}$P] ATP (68 kBq/ml), bovine cerebral TPK1 and a compound shown in Table (a final mixture contained 1.7% DMSO deriving from a solution of a test compound prepared in the presence of 10% DMSO) was used as a reaction system. The phosphorylation was started by adding ATP, and the reaction was conducted at 25° C. for 2 hours, and then stopped by adding 21% perchloric acid on ice cooling. The reaction mixture was centrifuged at 12,000 rpm for 5 minutes and adsorbed on P81 paper (Whatmann), and then the paper was washed four times with 75 mM phosphoric acid, three times with water and once with acetone. The paper was dried, and the residual radioactivity was measured using a liquid scintillation counter. The results are shown in the table below. The test compound markedly inhibited the P-GS1 phosphorylation by TPK1. The results strongly suggest that the medicaments of the present invention inhibit the TPK1 activity, thereby suppress the Aβ neurotoxicity and the PHF formation, and that the medicaments of the present invention are effective for preventive and/or therapeutic treatment of Alzheimer disease and the above-mentioned diseases.

TABLE 3

| COMPOUND NO. | IC50/nM |
|---|---|
| 1.101 | 9.4 |
| 1.102 | 28.2 |
| 1.103 | 49 |
| 1.104 | 8.9 |
| 1.105 | 61.4 |
| 1.106 | 1.5 |
| 1.107 | 98.2 |
| 1.108 | 11.7 |
| 1.109 | 76.1 |
| 1.110 | 139.9 |
| 1.111 | 193.7 |
| 1.112 | 108.3 |
| 1.201 | 19.1 |
| 1.202 | 13 |
| 1.203 | 6.4 |
| 1.204 | 245.2 |
| 1.205 | 37.6 |
| 1.206 | 59.9 |
| 1.207 | 32.6 |
| 1.208 | 10.65 |
| 1.209 | 17.85 |
| 1.210 | 27.4 |
| 1.211 | 976.9 |
| 1.212 | 64.9 |
| 1.213 | 19.4 |
| 1.214 | 16.1 |
| 1.215 | 50.1 |
| 1.216 | 10.9 |
| 1.217 | 12 |
| 1.218 | 153.2 |
| 1.219 | 8.4 |
| 1.220 | 21.2 |

TABLE 3-continued

| COMPOUND NO. | IC50/nM |
|---|---|
| 1.221 | 31.5 |
| 1.222 | 21.5 |
| 1.223 | 9.4 |
| 1.224 | 29.8 |
| 1.225 | 9.4 |
| 1.226 | 23.7 |
| 1.227 | 16 |
| 1.228 | 555.1 |
| 1.229 | 215.8 |
| 1.230 | 154.5 |
| 1.231 | 12.8 |
| 1.232 | 162.4 |
| 1.233 | 41.6 |
| 1.234 | 15.6 |
| 1.301 | 61.1 |
| 1.302 | 14.9 |
| 1.303 | 51.2 |
| 1.304 | 25.2 |
| 1.305 | 58.6 |
| 1.401 | 43.7 |
| 1.501 | 69 |
| 1.502 | 33.9 |
| 1.503 | 149.5 |
| 1.504 | 955 |
| 1.505 | 394.5 |
| 1.601 | 39.8 |
| 1.701 | 30.3 |
| 1.801 | 58.1 |
| 1.802 | 22.6 |
| 1.803 | 947.5 |
| 1.804 | 100.1 |
| 1.805 | 0.37 uM |
| 1.806 | 55 |
| 1.807 | 99 |
| 1.808 | 67 |
| 1.809 | 431.4 |
| 1.810 | 201 |
| 1.901 | 115.3 |
| 1.902 | 123.8 |
| 1.903 | 7.8 |
| 1.904 | 30.3 |
| 2.001 | 428.6 |
| 2.002 | 0.20 uM |
| 2.003 | 0.26 uM |
| 2.101 | 115.2-342.2 |
| 2.102 | 236.5 |
| 2.201 | 56.4 |
| 2.202 | 157.9 |
| 2.203 | 43.1 |
| 2.204 | 37.6 |
| 2.205 | 18.4 |
| 2.206 | 73.2 |
| 2.207 | 307.2 |
| 2.208 | 107.7 |
| 2.209 | 941.3 |
| 2.210 | 134.1 |
| 2.211 | 658.5 |
| 2.301 | 20 |
| 2.302 | 160 |
| 2.303 | 27 |
| 2.304 | 167 |
| 2.305 | 108 |
| 2.401 | 0.11 uM |
| 2.402 | 0.15 uM |
| 2.501 | 386 |
| 2.502 | 349 |

Experiment 2: Inhibitory Activity on Tau Phosphorylation In Vivo

Test compound was administered to male CD-1 mice of 5-6 weeks weighing 25-35 g (Charles River Japan, inc.) at 1, 3, 10, 30 mg/kg p.o. (0.5% Tween/H$_2$O suspension) and after 1 h, mice were decapitated and cortex was promptly removed, followed by being frozen in liquid N$_2$. Cortex was directly homogenized with 2.3% SDS homogenization buffer (62.5 mM Tris-HCl, 2.3% SDS, 1 mM each of EDTA, EGTA and DTT, protease inhibitor cocktail (sigma P2714) containing 0.2 μM 4-(2-aminoethyl)benzenesulfonyl fluoride (AEBSF), 13 μM bestatin, 1.4 μM E-64, 0.1 mM leupeptin, 30 nM aprotinin, pH 6.8) and centrifuged at 15000×g for 15 min at 4° C. Protein concentrations were determined using DC protein assay kit (BIO-RAD). Supernatants were diluted with sample buffer (62.5 mM Tris-HCl, 25% glycerol, 2% SDS, 0.01% Bromophenol Blue, pH6.8) to adjust the protein concentrations around 0.5-2 mg/mg and then boiled for 5 min. 10 μg of samples were applied on 10% SDS-PAGE mini slab gels and transferred onto PVDF membranes. Membranes were incubated with PBS containing 5% non-fat milk for 1 h at r.t. and then probed with pS396 anti-body (BIOSOURCE) overnight at 4° C. Anti-rabbit IgG HRP-conjugated anti-body (Promega) was used as secondary anti-body. Membranes were visualized by ECL kit (Amerasham Bioscience) and detected by LAS1000 (Fuji Photo Film).

INDUSTRIAL APPLICABILITY

The compounds of the present invention have TPK1 inhibitory activity and are useful as an active ingredient of a medicament for preventive and/or therapeutic treatment of diseases caused by abnormal advance of TPK1 such as neurodegenerative diseases (e.g. Alzheimer disease) and the above-mentioned diseases.

The invention claimed is:

1. A compound represented by general formula (I):

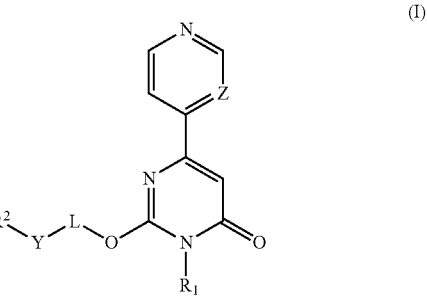

wherein:
Z represents a nitrogen atom or C—X;
X represents a hydrogen atom or a fluorine atom;
$R^1$ is a $C_1$-$C_3$ alkyl group; and
L, Y and $R^2$ are groups as represented by (1) or (2):
  (1) L is a single bond or a $C_1$-$C_6$ alkylene group which may have 1 to 4 substituents which are the same or different and selected from the group consisting of a halogen atom, amino group, nitro group, cyano group, oxo group, hydroxyl group, carboxyl group, and a $C_1$-$C_6$ alkyl group;
Y represents a single bond or an oxygen atom; and
$R^2$ is a cyclic group selected from the group consisting of a piperidyl group, a pyrrolidinyl group, a perhydroazepinyl group, an 8-aza-bicyclo[3.2.1]octanyl group, a dioxolanyl group, an oxanyl group, and a pyridyl group, wherein said cyclic group may have 1 to 3 substituents which are the same or different and selected from the group consisting of a halogen atom, nitro group, cyano group, a $C_1$-$C_6$ alkyl group which may be substituted, a $C_6$-$C_{10}$ aryl group which may be substituted, a 5- to 10-membered heterocyclic group which may be substituted, a $C_1$-$C_6$ alkyl-CO— group which may be substituted, a $C_1$-$C_6$ alkyl-O— group which may be substituted, a $C_6$-$C_{10}$ aryl-CO— group which may be substituted, a $C_1$-$C_6$ alkyl-O—CO— group which may be substituted, a $C_6$-$C_{10}$ aryl-O—CO— group which may be substituted, and a $C_6$-$C_{10}$ aryl-$SO_2$-group which may be substituted;

(2) L is a single bond;

Y is a single bond; and $R^2$ is a cyclic group represented by the following formula (III):

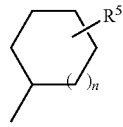

(III)

wherein $R^5$ represents a group selected from the group consisting of a $C_1$-$C_6$ alkyl group; and a $C_6$-$C_{10}$ aryl group which may have a substituent selected from the group consisting of a $C_1$-$C_6$ alkyl group which may be substituted by a hydroxyl group, and a 5- or 6-membered aliphatic monocyclic-heterocyclic-$C_1$-$C_6$ alkyl group which may be substituted by a $C_1$-$C_6$ alkyl group on the heterocyclic moiety; and n represents an integer of 0 or 1;

provided that when Y represents an oxygen atom, L is not a single bond, or a pharmaceutically acceptable salt thereof.

2. The compound or a pharmaceutically acceptable salt thereof according to claim 1, wherein $R^2$ is a cyclic group and selected from the group consisting of a piperidyl group, a pyrrolidinyl group, a perhydroazepinyl group, an 8-aza-bicyclo[3.2.1]octanyl group, a dioxolanyl group, an oxanyl group, and a pyridyl group, wherein said cyclic group may have 1 to 3 substituents which are the same or different and selected from the group consisting of a halogen atom, nitro group, cyano group, a $C_1$-$C_6$ alkyl group which may be substituted, a $C_6$-$C_{10}$ aryl group which may be substituted, a 5- to 10-membered heterocyclic group which may be substituted, a $C_1$-$C_6$ alkyl-CO— group which may be substituted, a $C_1$-$C_6$ alkyl-O— group which may be substituted, a $C_6$-$C_{10}$ aryl-CO— group which may be substituted, a $C_1$-$C_6$ alkyl-O—CO— group which may be substituted, a $C_6$-$C_{10}$ aryl group which may be substituted, and a $C_6$-$C_{10}$ aryl-$SO_2$-group which may be substituted;

L is a single bond or a $C_1$-$C_6$ alkylene group which may have 1 to 4 substituents which are the same or different and selected from the group consisting of a halogen atom, amino group, nitro group, cyano group, oxo group, hydroxyl group, carboxyl group, and a $C_1$-$C_6$ alkyl group; and Y represents a single bond or an oxygen atom.

3. The compound or a pharmaceutically acceptable salt thereof according to claim 1, wherein Y is single bond;

$R^2$ is a cyclic group which may be substituted, which is represented by the following formula (II):

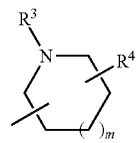

(II)

wherein $R^3$ represents a group selected from the group consisting of (1) to (11):
(1) a $C_6$-$C_{10}$ aryl group which may be substituted,
(2) a $C_6$-$C_{10}$ aryl-$SO_2$— group which may be substituted on the aryl moiety,
(3) a $C_6$-$C_{10}$ aryl-$C_1$-$C_6$ alkyl group which may be substituted on the aryl moiety,
(4) a $C_6$-$C_{10}$ aryl-CO— group which may be substituted on the aryl moiety,
(5) a $C_6$-$C_{10}$ aryl-O—CO— group which may be substituted on the aryl moiety,
(6) a $C_6$-$C_{10}$ aryl-$C_1$-$C_6$ alkyl-O—CO— group which may be substituted on the aryl moiety,
(7) a hydrogen atom,
(8) a $C_1$-$C_6$ alkyl-O—CO— group,
(9) a 5- to 10-membered heterocyclic group which may be substituted,
(10) a 5- or 6-membered aliphatic mono-heterocyclic group which may be substituted,
(11) a 5- or 6-membered aliphatic monocyclic-heterocyclic —$C_1$-$C_6$ alkyl group which may be substituted on the heterocyclic moiety;

$R^4$ represents a group selected from the group consisting of a hydrogen atom, a halogen atom, nitro group, cyano group, a $C_1$-$C_6$ alkyl group, and a $C_1$-$C_6$ alkyl-O— group; and m represents an integer of 0 to 2;

provided that when L represents a single bond, the binding position of Y to the group represented by formula (II) is a carbon atom that is not adjacent to the nitrogen atom.

4. The compound or a pharmaceutically acceptable salt thereof according to claim 3, wherein $R^3$ is selected from the group consisting of (1) to (11):
(1) a phenyl group which may be substituted;
(2) a phenyl-$SO_2$— which may be substituted on the phenyl moiety;
(3) a phenyl-$C_1$-$C_6$ alkyl group which may be substituted on the phenyl moiety;
(4) a phenyl-CO— group which may be substituted on the phenyl moiety;
(5) a phenyl-O—CO— group which may be substituted on the phenyl moiety;
(6) a phenyl-$C_1$-$C_6$ alkyl-O—CO— group which may be substituted on the phenyl moiety;

provided that when the phenyl moiety in each of the above (1) to (6) is substituted, the phenyl moiety is substituted by one or two groups independently selected from the group consisting of the following (i) to (viii):
(i) a 5- or 6-membered aliphatic monocyclic-heterocyclic-$C_1$-$C_6$ alkyl group, wherein the heterocyclic moiety may be substituted by a $C_1$-$C_6$ alkyl group, a $C_1$-$C_6$ alkyl-CO— group, a $C_1$-$C_6$ alkyl-O—CO— group or an oxo group,
(ii) a 5- or 6-membered aliphatic monocyclic-heterocyclic group, wherein the hetetocyclic moiety may be substituted by a $C_1$-$C_6$ alkyl group, a $C_1$-$C_6$ alkyl-CO— group or a $C_1$-$C_6$ alkyl-O—CO— group, (iii) a halogen atom,
(iv) a cyano group,
(v) a $C_1$-$C_6$ alkyl group which may be substituted by a 5- to 10-membered heterocyclic group,
(vi) a $C_1$-$C_6$ alkyl-O— group,
(vii) a di($C_1$-$C_6$ alkyl)amino-$C_1$-$C_6$ alkyl group,
(viii) a 5- or 6-membered heteroaryl group;
(7) a hydrogen atom;
(8) a $C_1$-$C_6$ alkyl-O—CO— group;
(9) a 5- to 10-membered heterocyclic group which may be substituted by the following (i) to (vi):
(i) a $C_1$-$C_6$ alkyl group, (ii) a $C_1$-$C_6$ alkyl-CO— group,
(iii) a phenyl-$C_1$-$C_6$ alkyl group,
(iv) a nitro group,
(v) an oxo group and
(vi) a $C_1$-$C_6$ alkyl-O— group;
(10) a 5- or 6-membered aliphatic monocyclic-heterocyclic group, which may be substituted by a $C_1$-$C_6$ alkyl group on the heterocyclic moiety;
(11) a 5- or 6-membered aliphatic monocyclic-heterocyclic-$C_1$-$C_6$ alkyl group, which may be substituted by a $C_1$-$C_6$ alkyl group or a phenyl-$C_1$-$C_6$ alkyl group on the heterocyclic moiety; and
$R^4$ is a hydrogen atom.

5. The compound or a pharmaceutically acceptable salt thereof according to claim 3, wherein L is a single bond or a methylene which may have a substituent selected from the group consisting of a halogen atom, amino group, nitro group, cyano group, oxo group, hydroxyl group, carboxyl group, and a $C_1$-$C_6$ alkyl group.

6. The compound or a pharmaceutically acceptable salt thereof according to claim 1, wherein
$R^2$ is a cyclic group represented by the following formula (III):

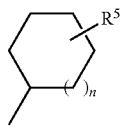

wherein
$R^5$ represents a group selected from the group consisting of a $C_1$-$C_6$ alkyl group, and a $C_6$-$C_{10}$ aryl group which may have a substituent selected from the group consisting of a $C_1$-$C_6$ alkyl group which may be substituted by a hydroxyl group, and a 5- or 6-membered aliphatic monocyclic-heterocyclic-$C_1$-$C_6$ alkyl group which may be substituted by a $C_1$-$C_6$ alkyl group on the heterocyclic moiety;
n represents an integer of 0 or
L is a single bond; and
Y is a single bond.

7. The compound or a pharmaceutically acceptable salt thereof according to claim 6, wherein $R^5$ represents a phenyl group which has a substituent selected from the group consisting of a $C_1$-$C_6$ alkyl group which may be substituted by a hydroxyl group, and a piperidyl-$C_1$-$C_6$ alkyl group which may be substituted by a $C_1$-$C_6$ alkyl group on the piperidyl moiety; and
n represents an integer of 1
L is single bond.

8. The compound according to claim 1 which is selected from the group consisting of:

1-Methyl-2-(1-phenyl-piperidin-3-yloxy)-1H-[4,4']bipyrimidinyl-6-one,
2-[1-(3-Fluoro-phenyl)-piperidin-3-yloxy]-1-methyl-1H-[4,4']bipyrimidinyl-6-one,
2-[1-(3-Methoxy-phenyl)-piperidin-3-yloxy]-1-methyl-1H-[4,4']bipyrimidinyl-6-one,
1-Methyl-2-(3,4,5,6-tetrahydro-2H-[1,2]bipyridinyl-3-yloxy)-1H-[4,4']bipyrimidinyl-6-one,
(S)-2-[1-(4-Fluoro-phenyl)-pyrrolidin-2-ylmethoxy]-6-(3-fluoro-pyridin-4-yl)-3-methyl-3H-pyrimidin-4-one,
tert-butyl 4-{4-[4-(1-Methyl-6-oxo-1,6-dihydro-[4,4']bipyrimidinyl-2-yloxy)-piperidin-1-yl]-benzyl}-piperazine-1-carboxylate,
1-Methyl-2-[1-(4-piperazin-1-ylmethyl-phenyl)-piperidin-4-yloxy]-1H-[4,4']bipyrimidinyl-6-one,
1-Methyl-2-[1-(4-morpholin-4-ylmethyl-phenyl)-piperidin-4-yloxy]-1H-[4,4']bipyrimidinyl-6-one,
1-Methyl-2-{1-[4-(4-methyl-piperazin-1-ylmethyl)-phenyl]-piperidin-4-yloxy}-1H-[4,4']bipyrimidinyl-6-one,
1-Methyl-2-[1-(4-piperazin-1-yl-phenyl)-piperidin-4-yloxy]-1H-[4,4']bipyrimidinyl-6-one,
1-Methyl-2-{1-[4-(4-methyl-piperazin-1-yl)-phenyl]-piperidin-4-yloxy}-1H-[4,4']bipyrimidinyl-6-one,
1-Methyl-2-[1-(4-piperidin-1-ylmethyl-phenyl)-piperidin-4-yloxy]-1H-[4,4']bipyrimidinyl-6-one,
1-Methyl-2-[1-(4-pyrrolidin-1-ylmethyl-phenyl)-piperidin-4-yloxy]-1H-[4,4']bipyrimidinyl-6-one,
2-{1-[4-(1,3-Dihydro-isoindol-2-ylmethyl)-phenyl]-piperidin-4-yloxy}-1-methyl-1H-[4,4']bipyrimidinyl-6-one,
1-Methyl-2-[1-(3-piperidin-1-ylmethyl-phenyl)-piperidin-4-yloxy]-1H-[4,4']bipyrimidinyl-6-one,
1-Methyl-2-{1-[2-(4-methyl-piperazin-1-ylmethyl)-phenyl]-piperidin-4-yloxy}-1H-[4,4']bipyrimidinyl-6-one,
6-(3-Fluoro-pyridin-4-yl)-3-methyl-2-[1-(4-piperidin-1-ylmethyl-phenyl)-piperidin-4-ylmethoxy]-3H-pyrimidin-4-one,
6-(3-Fluoro-pyridin-4-yl)-3-methyl-2-[1-(4-piperidin-1-ylmethyl-phenyl)-piperidin-4-yloxy]-3H-pyrimidin-4-one,
1-Methyl-2-[1-(4-piperidin-1-ylmethyl-phenyl)-pyrrolidin-3-yloxy]-1H-[4,4']bipyrimidinyl-6-one,
cis-1-Methyl-2-{4-[4-(4-methyl-piperazin-1-ylmethyl)-phenyl]-cyclohexyloxy}-1H-[4,4']bipyrimidinyl-6-one,
trans-1-Methyl-2-{4-[4-(4-methyl-piperazin-1-ylmethyl)-phenyl]-cyclohexyloxy}-1H-[4,4']bipyrimidinyl-6-one,
2-[1-(2,3-Dihydro-1H-isoindol-5-yl)-piperidin-4-yloxy]-1-methyl-1H-[4,4']bipyrimidinyl-6-one, and
2-[1-(2-Benzyl-2,3-dihydro-1H-isoindol-5-yl)-piperidin-4-yloxy]-1-methyl-1H-[4,4']bipyrimidinyl-6-one
or a pharmaceutically acceptable salt thereof.

9. A method for therapeutic treatment of a disease or condition selected from the group consisting of non-insulin dependent diabetes, Alzheimer's disease, ischemic cerebrovascular accidents, progressive supranuclear palsy, Pick's disease, corticobasal degeneration, and frontotemporal dementia, comprising administering to the patient in need thereof an effective amount of the compound or a pharmaceutically acceptable salt thereof according to claim 1.

10. The method according to claim 9, wherein the disease or condition which is Alzheimer's disease.

11. A pharmaceutical composition for inhibiting tau protein kinase 1 activity, comprising the compound or a pharmaceutically acceptable salt thereof according to claim 1 as an active ingredient.

* * * * *

UNITED STATES PATENT AND TRADEMARK OFFICE
CERTIFICATE OF CORRECTION

PATENT NO. : 9,006,232 B2
APPLICATION NO. : 13/389512
DATED : April 14, 2015
INVENTOR(S) : K. Nakayama et al.

Page 1 of 1

It is certified that error appears in the above-identified patent and that said Letters Patent is hereby corrected as shown below:

IN THE CLAIMS

At column 107, line 65 (claim 7, line 9), please delete "L is single bond".

Signed and Sealed this
Twenty-third Day of February, 2016

Michelle K. Lee
*Director of the United States Patent and Trademark Office*